(12) United States Patent
Reid et al.

(10) Patent No.: US 9,073,980 B2
(45) Date of Patent: Jul. 7, 2015

(54) TUMOR SELECTIVE E1A AND E1B MUTANTS

(75) Inventors: Tony Reid, San Diego, CA (US); Farah Hedjran, San Diego, CA (US); Shantanu Kumar, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 768 days.

(21) Appl. No.: 13/254,825

(22) PCT Filed: Mar. 2, 2010

(86) PCT No.: PCT/US2010/025926
§ 371 (c)(1),
(2), (4) Date: Sep. 2, 2011

(87) PCT Pub. No.: WO2010/101921
PCT Pub. Date: Sep. 10, 2010

(65) Prior Publication Data
US 2011/0318311 A1   Dec. 29, 2011

Related U.S. Application Data

(60) Provisional application No. 61/156,822, filed on Mar. 2, 2009.

(51) Int. Cl.
| C07K 14/005 | (2006.01) |
| C12N 7/00 | (2006.01) |
| C12N 15/86 | (2006.01) |
| A61K 48/00 | (2006.01) |

(52) U.S. Cl.
CPC ............... *C07K 14/005* (2013.01); *A61K 48/00* (2013.01); *C12N 7/00* (2013.01); *C12N 15/86* (2013.01); *C12N 2710/10321* (2013.01); *C12N 2710/10322* (2013.01); *C12N 2710/10332* (2013.01); *C12N 2710/10343* (2013.01); *C12N 2830/00* (2013.01)

(58) Field of Classification Search
CPC ..... A61K 48/00; A61K 38/00; A61K 35/761; A61K 2039/5256; A61K 2039/55511; A01K 2217/05; C07K 14/005; C07K 14/4702; C12Q 1/6886; C12N 2740/16322; C12N 2799/021; C12N 2799/022; C12N 2830/002; C12N 2830/008; G01N 2500/10; G01N 33/574
USPC ..................................................... 435/320.1
See application file for complete search history.

(56) References Cited

U.S. PATENT DOCUMENTS

| 5,601,818 A | 2/1997 | Freeman et al. |
| 5,631,236 A | 5/1997 | Woo et al. |
| 5,643,567 A | 7/1997 | Hung et al. |
| 5,783,666 A | 7/1998 | Albertsen et al. |
| 2006/0270016 A1 | 11/2006 | Holm |
| 2009/0232800 A1* | 9/2009 | Holm ........................ 424/133.1 |

FOREIGN PATENT DOCUMENTS

| EP | 1347042 A1 | 9/2003 |
| WO | WO 97/06826 A1 | 2/1997 |
| WO | WO 98/27216 A1 | 6/1998 |

OTHER PUBLICATIONS

Edbauer et al. J. Virol. 1988, vol. 62, No. 9, pp. 3265-3273.*
Hedjran et al., "Deletion analysis of Ad5 E1a transcriptional control region: impact on tumor-selective expression of E1a and E1b", Cancer Gene Therapy, vol. 18, No. 10, Oct. 2011, pp. 717-723, XP002679460.
Johnson Leisa et al., "Selectively replicating adenoviruses targeting deregulated E2F activity are potent, systemic antitumor agents", Cancer Cell, Cell Press, US, vol. 1, No. 4, May 1, 2002, pp. 325-337, XP002461313, ISSN: 1535-6108, DOI: 10.1016/S1535-6108(02)00060-0.
Search Report mailed Jul. 20, 2012 in related European Patent Application No. 10749205.0, filed Mar. 2, 2010, 4 pages.
Written Opinion mailed Nov. 19, 2010 in related PCT Application No. PCT/US2010/025926, filed Mar. 2, 2010, 7 pages.
Bruder, J. T. et al., Cooperative binding of EF-1A to the E1A enhancer region mediates synergistic effects on E1A transcription during adenovirus infection, Journal of Virology 65(9):5084-5087, Sep. 1991.
Bruder, J.T. And Hearing, P., Nuclear factor EF-1A binds to the adenovirus E1A core enhancer element and to other transcriptional control regions, Molecular and Cellular Biology 9:5143-5153, Nov. 1989.
de Launoit, Y. et al., The PEA3 group of ETS-related transcription factors, Advances in Experimental Medicine and Biology 480:107-116, 2000.
Falck-Pedersen, E. et al., Transcription termination within the E1A gene of adenovirus induced by insertion of the mouse β-major globin terminator element, Cell 40(4):897-905, Apr. 1985.
Hanahan, D. et al., The hallmarks of cancer, Cell 100(1):57-70, Jan. 7, 2000.
Hearing, P. et al., The adenovirus type 5 E1A transcriptional control region contains a duplicated enhancer element, Cell 33(3):695-703, Jul. 1983.

(Continued)

*Primary Examiner* — Bao Li
(74) *Attorney, Agent, or Firm* — Mintz, Levin, Cohn, Ferris, Glovsky and Popeo, P.C.

(57) ABSTRACT

Modified E1a regulatory sequences are provided, wherein at least one Pea3 binding site, or a functional portion thereof, is deleted. Also provided are modified E1a sequences that selectively express particular isoforms. Also provided is an E1b-19K clone insertion site. These modified sequences can be used individually, or in combination with one another, to provide tumor-selective expression of proteins.

13 Claims, 50 Drawing Sheets

(56) References Cited

OTHER PUBLICATIONS

Hiroumi et al., Expression of E1AF/PEA3, an ETS-related transcription factor in human non-small-cell lung cancers: its relevance in cell motility and invasion, Int. J. Cancer, 93(6):786-791, 2001.
International Search Report for International Application No. PCT/US2010/025926 dated Nov. 19, 2010, 3 pages.
Maxfield, L. F. et al., Readthrough activation of early adenovirus E1b gene transcription, Journal of Virology 71(11):8321-8329, Nov. 1997.
Montell, C. et al., Control of adenovirus E1B Mrna synthesis by a shift in the activities of RNA splice sites, Molecular and Cellular Biology 4(5):966-972, May 1984.
Weintraub, S.J. et al., Retinoblastoma protein switches the E2F site from positive to negative element, Nature 358:259-261, Jul. 16, 1992.
Wu, L. et al., A TATA box implicated in E1A transcriptional activation of a simple adenovirus 2 promoter, Nature 326:512-515, Apr. 2, 1987.

* cited by examiner

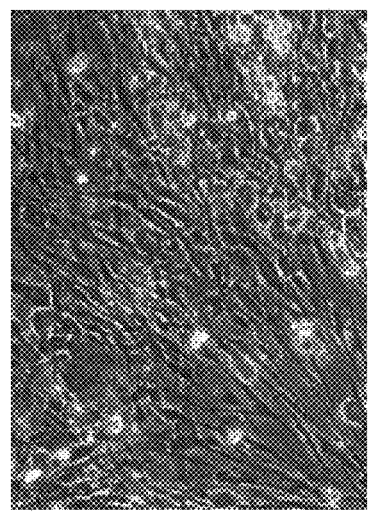
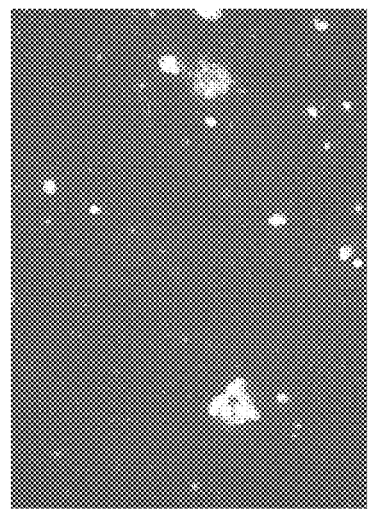
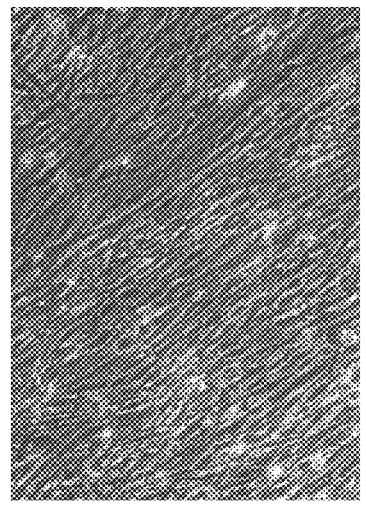
Figure 7c

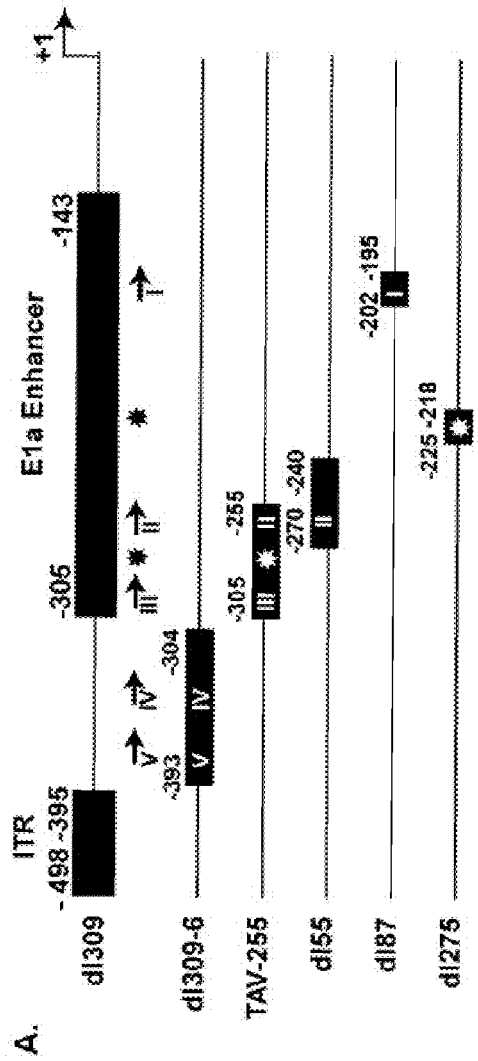
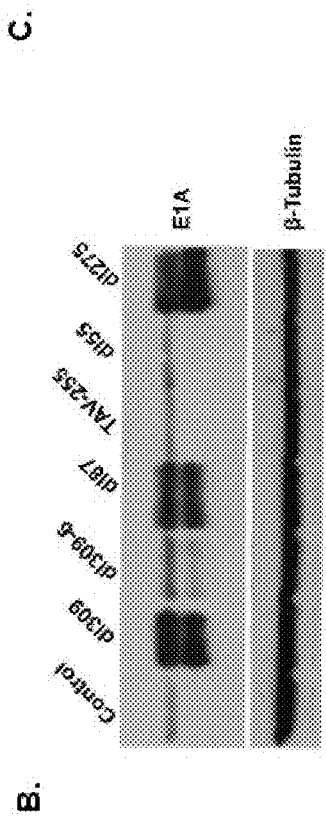
Figure 8

Figure 21: Cell Viability

Figure 27

TUMOR SELECTIVE E1A AND E1B MUTANTS

CROSS-REFERENCES TO RELATED APPLICATIONS

This application is a National Stage filing of International Application No. PCT/US2010/025926, filed Mar. 2, 2010, and claims the benefit of U.S. Provisional Application No. 61/156,822, filed Mar. 2, 2009, each of which is incorporated herein by reference in its entirety and for all purposes.

BACKGROUND OF THE INVENTION

Despite extensive knowledge of the underlying molecular mechanisms that cause cancer, most advanced cancers remain incurable with current chemotherapy and radiation protocols. Oncolytic viruses have emerged as a platform technology that has the potential to significantly augment current standard treatment for a variety of malignancies (Kumar, S. et al., *Current opinion in molecular therapeutics* 10(4):371-379 (2008); Kim, D. *Expert opinion on biological therapy* 1(3): 525-538 (2001); Kim D. *Oncogene* 19(56):6660-6669 (2000)). ONYX-015, which has a deletion of the viral E1b-55k gene, was postulated to confer tumor-selective replication in tumors with defects in the p53 pathway (Heise, C. et al., *Nat Med* 3(6):639-645 (1997); McCormick, F. *Oncogene* 19(56):6670-6672 (2000); Bischoff, J. R. et al., *Science* 274 (5286):373-376 (1996)). E1b-55k binds and inactivates p53, permitting unscheduled DNA synthesis and viral replication. Inactivation of p53 by E1b-55k, while critical for efficient replication of adenovirus in normal cells, was hypothesized to be irrelevant in tumors having inactivating mutations in the p53 pathway. Preclinical studies demonstrated that a wide range of human tumor cells with mutant or normal p53 gene sequences supported the replication of ONYX-015 in cell culture, demonstrating that permissive viral replication in tumors cells was not strictly dependent on the p53 binding effects of E1b-55k (Heise, C. et al., *Nat Med* 3(6):639-645 (1997); Heise, C. et al., *Clin Cancer Res* 6(12):4908-4914 (2000); Rogulski, K. R. et al. *Cancer Res* 60(5):1193-1196 (2000); Harada, J. N. et al., *J Virol* 73(7):5333-5344 (1999); Goodrum, F. D. et al., *Journal of virology* 72(12):9479-9490 (1998)). Previous studies had demonstrated that E1b-55k is a multifunctional protein that, in addition to binding and inactivating p53 during the early phase of infection, facilitates mRNA transport across the nuclear membrane during later phases of infection (Babiss, L. E. et al., *Mol Cell Biol* 5(10): 2552-2558 (1985); Leppard, K. N. et al., *Embo J* 8(8):2329-2336 (1989)). The lack of efficient mRNA transport due to the deletion of E1b-55k resulted in lower viral replication even in tumor cells when compared to wild-type Ad5. Detailed analysis demonstrated that the loss of the mRNA transport function provided by E1b-55k could be complemented in tumor cell lines, suggesting a novel mechanism of tumor-selective viral replication (O'Shea, C. C. et al., *Cancer Cell* 8(1):61-74 (2005)). However, complementation of lost functions due to viral gene deletion was incomplete in most tumor cells since the titer of ONYX-015 in tumor cells was often one to two logs lower than wild-type Ad5 in the same tumor cells (Heise, C. et al., *Clin Cancer Res* 6(12):4908-4914 (2000); Goodrum, F. D. et al., *Journal of virology* 72(12):9479-9490 (1998)).

Clinical trials using ONYX-015 in a variety of malignancies, including head and neck, colorectal, pancreatic, lung, breast and brain cancer have demonstrated that this oncolytic virus was well tolerated when administered alone or with chemotherapy (Heise, C. et al., *Nat Med* 3(6):639-645 (1997); Galanis, E. et al., *Gene Ther* 12(5):437-445 (2005); Chiocca, E. A. et al., *Mol Ther* 10(5):958-966 (2004); Hecht, J. R. et al., *Clin Cancer Res* 9(2):555-561 (2003); Reid, T. et al., *Cancer Res* 62(21):6070-6079 (2002); Vasey, P. A. et al., *J Clin Oncol* 20(6):1562-1569 (2002); Reid, T. et al., *Gene Ther* 8(21):1618-1626 (2001); Nemunaitis, J. et al., *J Clin Oncol* 19(2):289-298 (2001); Kim, D. *Gene Ther* 8(2):89-98 (2001); Nemunaitis, J. et al., *Gene Ther* 8(10):746-759 (2001)). However, objective clinical responses following ONYX-015 administration were uncommon raising concerns that this virus, while well tolerated by intratumoral, intravenous and even intraarterial administration, lacked sufficient potency to be broadly applicable as a therapeutic agent (Kim, D. *Gene Ther* 8(2):89-98 (2001)). The low viral titer for ONYX-015 in various tumor cell lines when compared to wild-type Ad5 raised concerns that the potency of ONYX-015 was not sufficient to be clinically active as an anticancer agent. In addition, E1a, the first protein produced by the virus, was not under tumor-selective control, permitting expression of this potent viral protein in normal cells as well as tumor cells. Since the function of E1a is to facilitate entry of cells into cell division, an oncolytic virus would optimally have both E1a and E1b under tumor-selective control.

Extensive work has been directed at developing a tumor-selective virus with improved anti-tumor potency when compared to ONYX-015. One approach that we and others have taken for making oncolytic viruses has been to insert tumor-selective promoter elements upstream of critical transcription units including E1a, E1b and E4 (Li, Y. et al., *Clin Cancer Res* 11(24 Pt 1):8845-8855 (2005); Huang, T. G. et al., *Gene Ther* 10(15):1241-1247 (2003); Wirth, T. et al., *Cancer Res* 63(12): 3181-3188 (2003); Gu, J. et al., *Gene Ther* 9(1):30-37 (2002); Johnson, L. et al., *Cancer Cell* 1(4):325-337 (2002); Li, X. et al., *Cancer Res* 65(5):1941-1951 (2005); Li, Y. et al., *Mol Cancer Ther* 2(10):1003-1009 (2003)). Incorporation of heterologous promoter elements, such as the promoter for prostate specific antigen (PSA), carcinogenic-embryonic antigen (CEA), E2F1 and telomerase, has achieved variable levels of tumor-selective replication. The potential clinical utility of viruses using heterologous promoters to provide tumor-selective replication has been limited by non-selective and leaky gene expression, diminished capacity of these vectors to replicate when compared to the wild-type virus and recombination events due to the heterologous promoter sequence. For example, ONYX-411 was developed to improve on the potency of ONYX-015 by insertion of the E2F1 promoter region upstream of E1a and E4 (Johnson, L. et al., *Cancer Cell* 1(4):325-337 (2002)). However, this virus has not been developed for clinical use. In an effort to overcome some of the limitations of heterologous enhancer sequences, we have evaluated the native viral transcriptional control region for E1a to determine if tumor-selective viral replication could be achieved by directed engineering of the native E1a enhancer.

BRIEF SUMMARY OF THE INVENTION

Provided herein are modified sequences that can be used individually, or in combination with one another, to provide tumor-selective expression of proteins.

In one aspect, a recombinant virus comprises a modified E1a regulatory sequence, wherein at least one Pea3 binding site, or a functional portion thereof, is deleted. In one aspect, at least one nucleotide in the range of −305 to −141 is retained.

In one aspect, at least one of Pea3 II, Pea3 III, Pea3 IV, and Pea3 V, or a functional portion thereof, is deleted. In another aspect, at least one of Pea3 II and Pea3 III, or a functional portion thereof, is deleted. In one aspect, Pea3 II or a functional portion thereof, and Pea3 III or a functional portion thereof, is deleted. In another aspect, at least one of Pea3 IV and Pea3 V, or a functional portion thereof, is deleted. In another aspect, Pea3 I, or a functional portion thereof, is retained.

In one aspect, at least one E2F binding site, or a functional portion thereof, is retained.

In one aspect, the vector is dl309-6, TAV-255, dl55, dl200, dl230, or dl200+230. In another aspect, the vector is TAV-255.

In one aspect, a recombinant virus selectively expresses at least one E1a isoform, e.g., E1a-12S or E1a-13S. In another aspect, the recombinant virus substantially excludes expression of an E1a isoform, e.g., the other of E1a-12S or E1a-13S that is not selectively expressed. In one aspect, the sequence encoding the E1a isoform is operably linked to a modified E1a regulatory sequence, wherein at least one Pea3 binding site, or a functional portion thereof, is deleted.

In one aspect, a recombinant virus comprises a DNA sequence, e.g., a transgene, inserted into an E1b-19K insertion site. In one aspect, the insertion site is located between the start site of E1b-19K and the start site of E1b 55K. In another aspect, the insertion site comprises a deletion of 202 base pairs following the start site of E1b-19K.

In one aspect, the transgene is a sequence encoding tumor necrosis factor, or a functional portion thereof. In another aspect, the transgene is a sequence encoding kras, or a functional portion thereof. In another aspect, the transgene is operably linked to a modified E1a regulatory sequence, wherein at least one Pea3 binding site, or a functional portion thereof, is deleted.

In any of these aspects, the recombinant virus can be an adenovirus. In another aspect, a cell is transformed with any one of these recombinant viruses.

In another aspect, a method of selectively expressing a peptide in a target cell comprises contacting the target cell with any one of these recombinant viruses. In one aspect, the recombinant virus comprises a deletion mutant E1a regulatory sequence operably linked to a nucleotide sequence encoding a peptide, e.g., a peptide associated with viral replication or with cancer.

In one aspect, the target cell is a neoplastic cell. In another aspect, the target cell is a normal cell.

The method can be practiced in vivo or in vitro. In one aspect, the virus is administered by intramuscular, intravenous, intraarterial, or intratumoral injection.

BRIEF DESCRIPTION OF THE FIGURES

E1a Transcriptional Control Region Deletions

FIG. 8. Deletion mutants of dl309 and E1a expression in MRC-5 cells. (a) Schematic presentation of upstream control region of HAd-5 E1a transcriptional unit. Transcription start site (+1), enhancer region (−305 to −141) and ITR region (−498 to −395) are indicated at the top. Five Pea3 binding sites in dl309 genome are indicated by arrow, and two E2F binding sites are indicated by star. Deletion mutant viruses and their encompassing nucleotides are indicated by solid bar and nucleotides are indicated on their top. Name of the mutant virus is indicated left to the schematic diagram. (b) Western blot analysis of E1a proteins extracted from MRC-5 cells infected with mutant viruses after 24 h.p.i.; β-tubulin (loading control) is shown below the E1a blot. (c) Relative quantification of E1a mRNA produced by mutant adenoviruses in MRC-5 cells at 24 h.p.i.

Figure 26A:
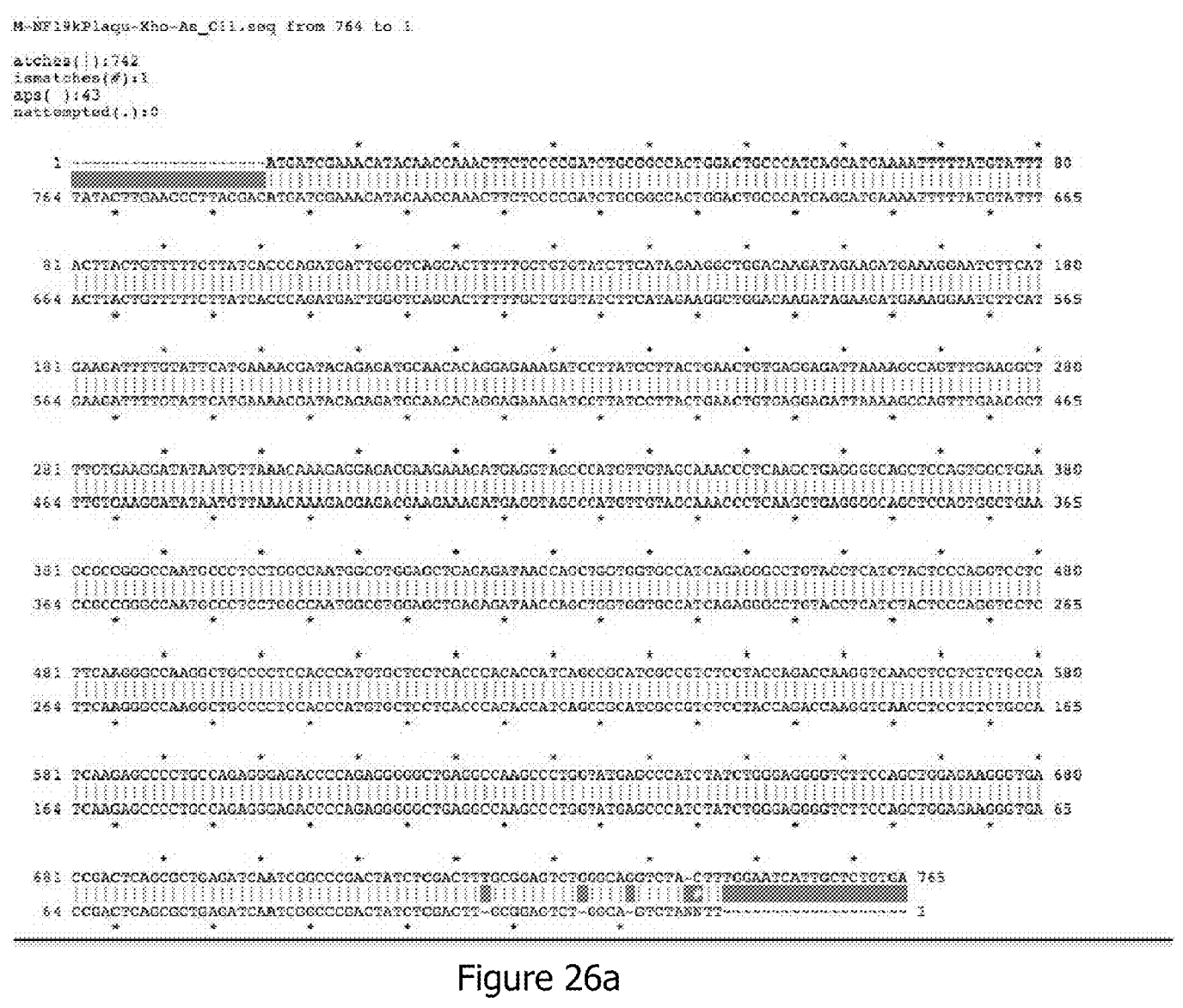
Figure 26B:
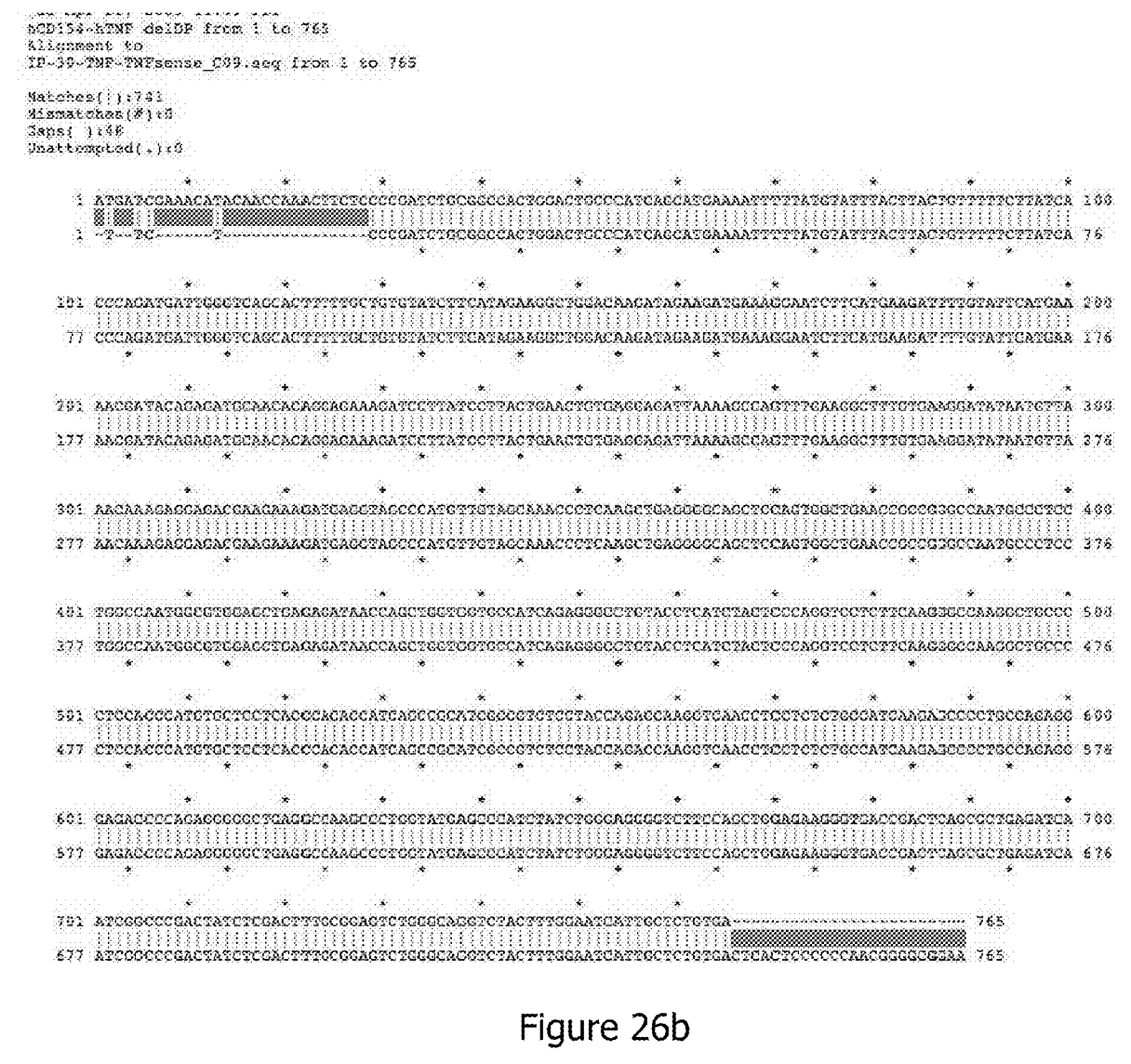

FIGS. 26a and 26b. Demonstrate the sequence of membrane-stabilized TNF inserted selectively into the E1b-19k region of Ad5. Sequences: FIG. 26a: SEQ ID NOS:15-16; FIG. 26b: SEQ ID NOS:17-18.

Figure 27:
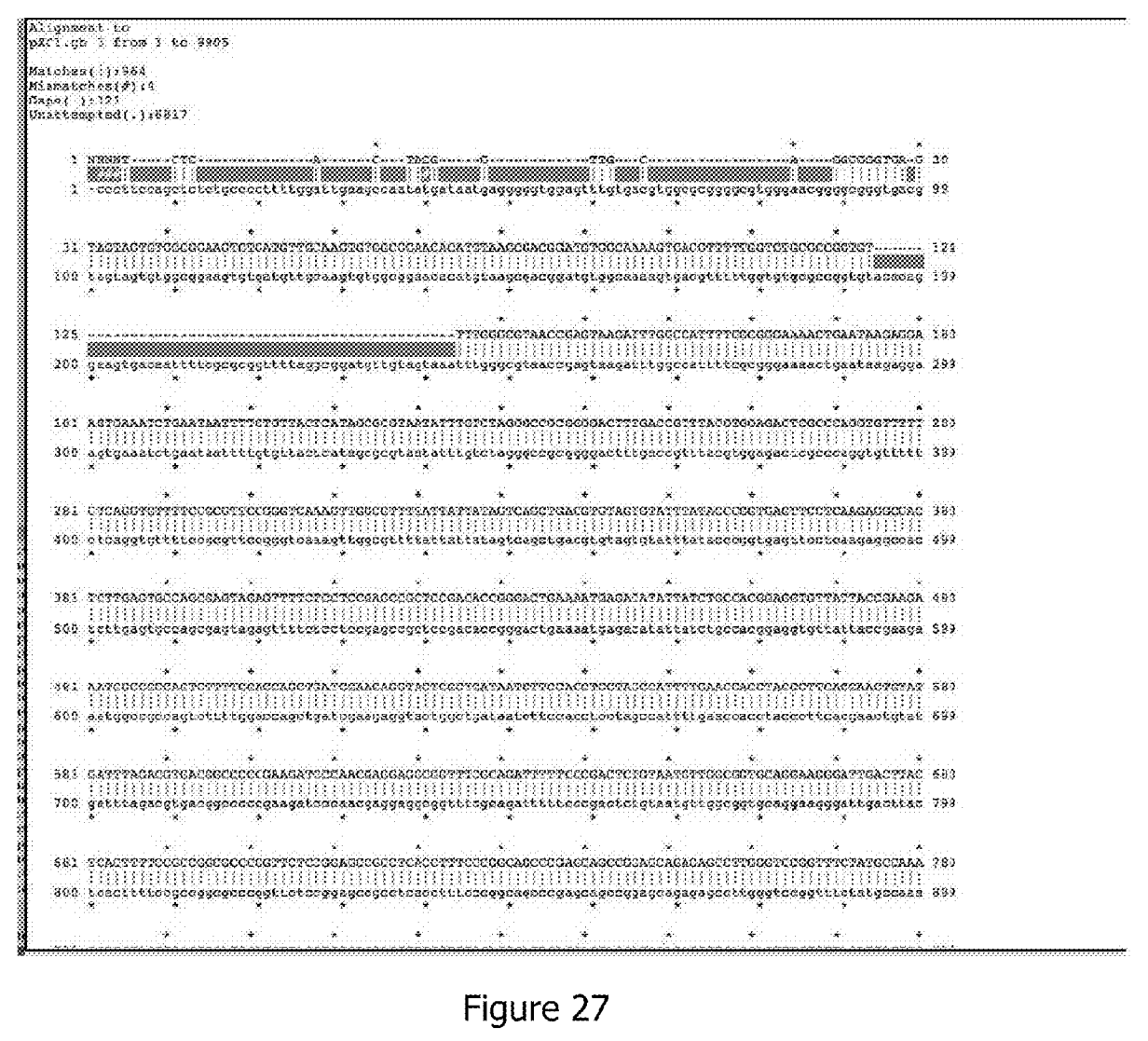

FIG. 27. Demonstrates the sequence of the 50 base-pair deletion in the promoter of E1a yielding a vector with a deletion in E1b-19k and the TAV-255 promoter deletion. Sequences: FIG. 27: SEQ ID NOS:19-20.

DETAILED DESCRIPTION OF THE INVENTION

I. Abbreviations and Definitions

Figure 1A:
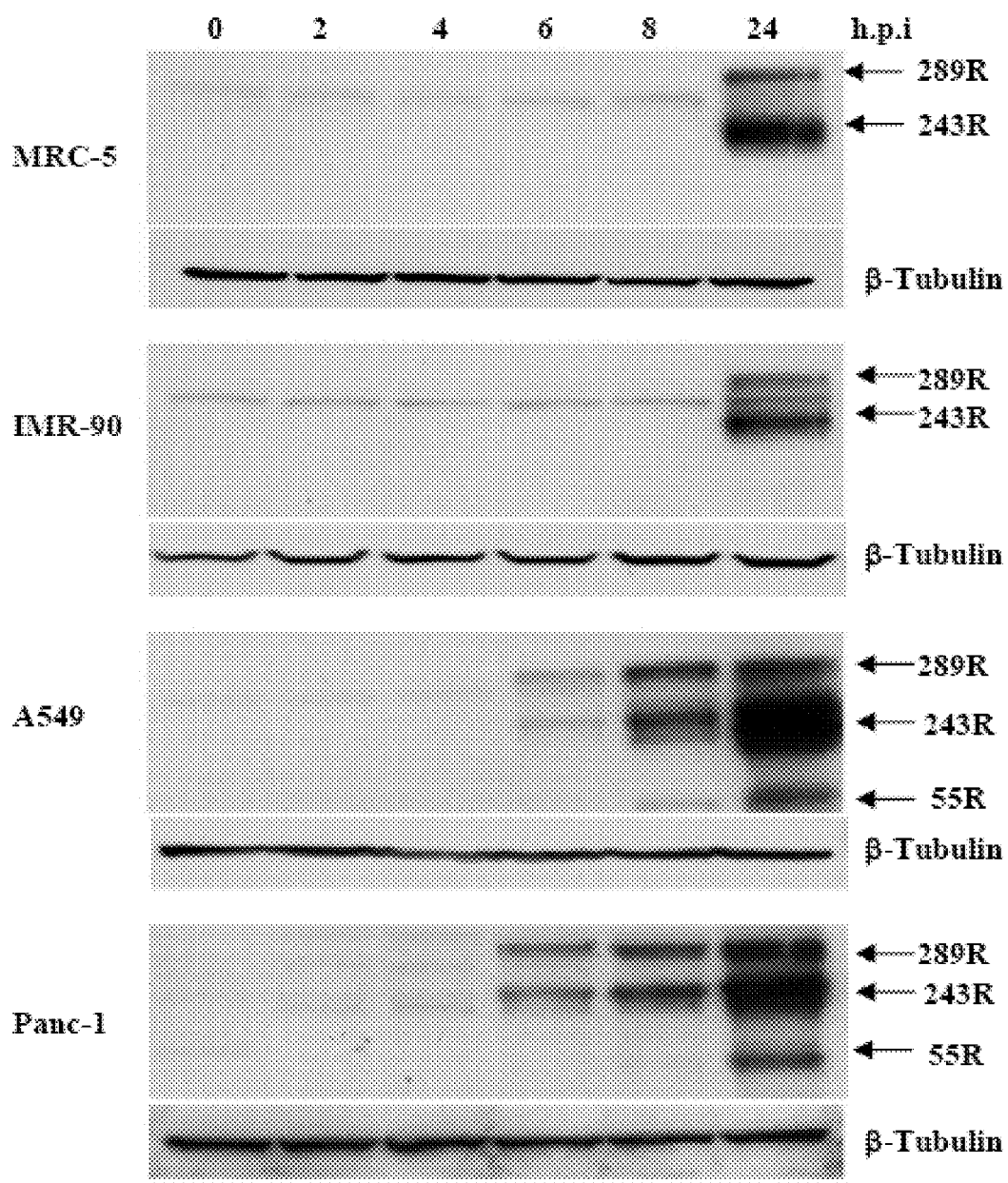
FIG. 1. Expression of adenoviral E1A protein in lung fibroblasts and cancer cells infected with Wt Ad5. Quiescent primary lung fibroblasts and cancer cell lines were infected with Wt Ad5 at multiplicity of infection (MOI) of 5 and proteins were extracted at various hours post infections (h.p.i.) and analyzed for E1A expression. (a) Expression of E1A protein in quiescent cell lines (MRC-5 and IMR-90) and cancer cell lines (A549 and PANC-1). (b) Expression of E1A in various tumor cell lines, AsPC-1, LNCaP, HeLa, and Calu-6. Various splice variant of E1A protein with amino acids residues (R): 289R, 243R, and 55R are shown by arrow. β-tubulin (loading control) are indicated next to the western blots. Time courses are indicated at the top of panel, and cell lines are indicated left of each blot.

The abbreviations used herein have their conventional meaning within the chemical and biological arts. For ease of reference, the abbreviations used herein are as defined as follows:
Wt Ad5: wild type adenovirus type 5
MOI: multiplicity of infection
hpi: hours post infection
The neoplastic cell lines referenced herein include:
A549: lung cancer
PANC-1: pancreatic cancer
AsPC-1: pancreatic cancer
LNCaP: prostate cancer
HeLa: cervical cancer
Calu-6: lung cancer
SK-Mel-28: melanoma
The non-neoplastic cell lines referenced herein include respiratory lung fibroblast cell lines MRC-5, WI-38, and IMR-90. Cell line HEK-293A is adenovirus E1-transformed human embryonic kidney cells.

The deletion mutants used herein are characterized by the deletion of the nucleotides indicated below. Binding sites affected by the deletion are shown in parentheses.
dl309: −498 to −395, −305 to −141
dl309-6: −393 to −304 (Pea3 V and Pea3 IV)
dl340-12: −145 to −44
TAV-255: −305 to −255 (Pea3 III, E2F II, Pea3 II)
dl87: −201 to −195 (Pea3 I)
dl55: −270 to −240 (Pea3 II)
dl275: −225 to −218 (E2F I)
dl200: −299 to −293 (Pea3 III)
dl212: −287 to −281 (E2F II)
dl220: −280 to −275
dl230: −270 to −265 (Pea3 II)
dl200+230: −299 to −293 (Pea3 III), −270 to −265 (Pea3 II)
dl212+275: −287 to −281 (E2F II), −225 to −218 (E2F I)
The terms "a" or "an," as used in herein means one or more, unless specifically noted as singular.

II. Investigation of Deletions in the E1a Transcriptional Control Region

E1a is the first gene expressed after HAd-5 infection and is essentially required for a successful virus replication (Gaynor, R. B., and Berk, A. J. (1983). Cis-acting induction of adenovirus transcription. Cell 33: 683-693). The adenoviral E1a transcriptional control region has multiple regulatory elements including two binding sites for E2F1 and five binding sites for Pea3 (Bruder, J. T. et al., *J Virol* 65(9):5084-5087 (1991)). These transcription factors are commonly aberrantly expressed in tumor cells (de Launoit, Y. et al., *Adv Exp Med Biol* 480:107-116 (2000); Hanahan, D. et al., *Cell* 100(1):57-70 (2000)). Since there are multiple binding sites for these transcription factors, we sought to determine if some of these binding sites were critical for efficient E1a expression in normal cells but not in tumor cells. We observed that E1a mRNA and protein is expressed at earlier times and at higher levels in tumor cells compared to non-transformed cells infected with human Adenovirus 5 (Ad5). To understand the mechanism of this effect, we evaluated the impact of a series of small deletions throughout the E1a transcriptional control region on the expression of E1a in tumor cells and non-transformed respiratory epithelial cells. Various deletions in the region upstream of the E1a initiation site reduced expression of E1a in non-transformed respiratory epithelial cells while having minimal impact on the expression of E1a in tumor cells. In particular, the TAV-255 which has a deletion of a 50 base pair region located from −305 to −255 upstream of the E1a initiation site resulted in marked reduction of E1a mRNA and protein expression in non-transformed cells, while retaining E1a expression similar to Wt Ad5 in tumor cells. In addition, this 50 bp deletion resulted in markedly diminished expression of E1b in non-transformed cells while retaining near normal levels of E1b in tumor cells. Although it is highly attenuated in non-transformed cells, TAV-255 is similar to wild-type Ad5 in expression of E1a and E1b and cytolytic activity in tumor cell lines.

Figure 1B:
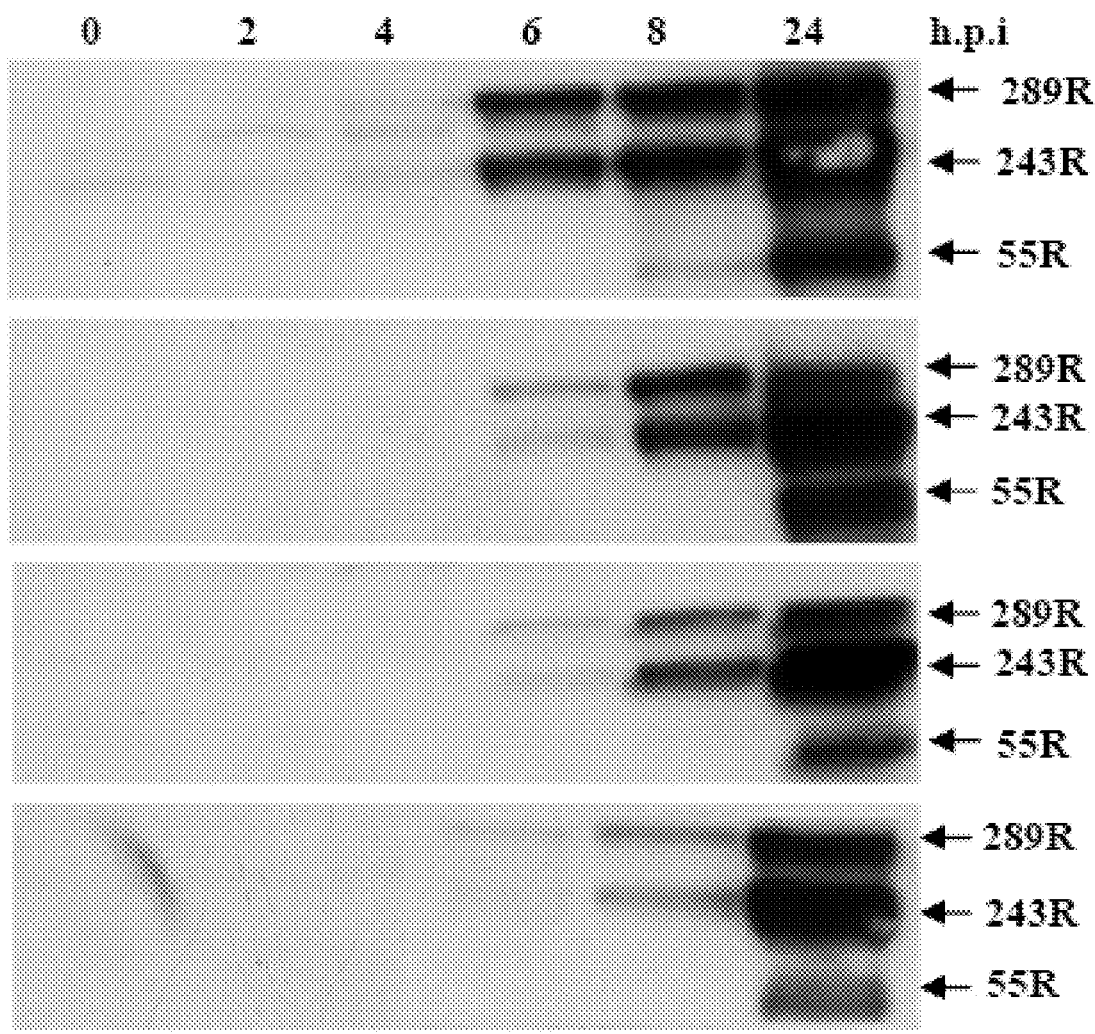

E1a mRNA and protein is induced earlier and in greater abundance in tumor cells than in non-transformed cells. The native transcriptional control region of Ad5 has binding sites for transcription factors commonly over expressed in tumor cells including binding sites for E2F1, Sp1 and Pea3. Consequently, the regulation of E1a expression may be different in tumor cells than in non-transformed cells. To evaluate this possibility, wild-type Ad5 was used to infect tumor cells and non-transformed cells (MOI=5) and the expression of E1a protein was evaluated at several time points after infection of the cells. The results (FIG. 1a) demonstrate that E1a expression is detected earlier and in greater abundance in tumor cell lines (A549 and PANC-1) compared to non-transformed respiratory epithelial cells (MRC-5 and IMR-90). Abundant expression of E1a protein is observed at 6 to 8 hours post infection (h.p.i.) in the tumor cell lines while no detectable expression of E1a is observed at these times in the non-transformed respiratory epithelial cell lines MRC-5 and IMR-90. At 24 hours post infection expression of E1a (289R and 243R, corresponding to the 13s and 12s mRNA species respectively) is observed in both MRC-5 and IMR-90 at comparable levels. However, the amount of E1a (55R, 243R and 289R) detected in the tumor cells by western blot greatly exceeds the amount seen in the non-transformed cells. The abundance of E1a observed in the tumor cells at 8 hours post-infection is comparable to the abundance of E1a observed in the non-transformed cells at 24 hours post-infection. To further evaluate this effect, the onset and abundance of E1a expression was evaluated in a panel of tumor cell lines (FIG. 1b) including AsPc-1 and PANC-1 (pancreatic), Calu-6 (lung), LNCaP (prostate) and HeLa (cervical) cells. In each of these cell lines, expression of E1a is detected by 6 to 8 hours post infection in the transformed cells and the amount of E1a observed in the transformed cells at 6 to 8 hours post-infection is comparable to that of E1a observed in the non-transformed cells at 24 hours post-infection (FIG. 1a).

Figure 2:
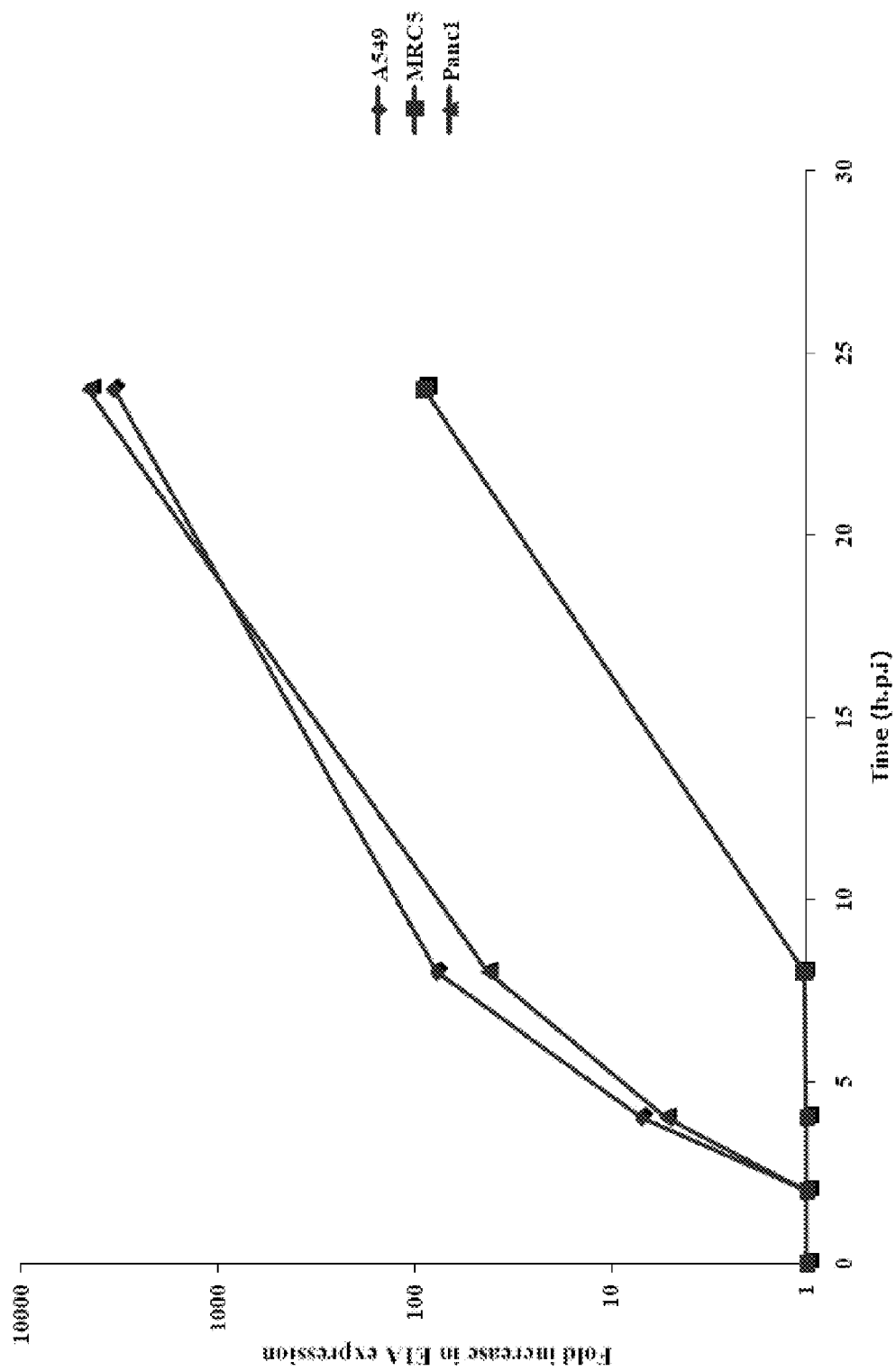
FIG. 2. Induction of E1A mRNA in infected (a) MRC-5, (b) A549, and (c) PANC-1 cells (MOI 5) at various hour post infection. E1A expression fold increase was calculated relative to Wt Ad5 E1A expression in MRC5 cell lines at 6 h.p.i.

E1a mRNA expression occurs earlier and is more abundant in tumor cells compared to non-transformed cells by quantitative PCR. Detectable increases in E1a mRNA occurred in A549 and PANC-1 cells within 2 to 4 hours of infection and exceed the expression in MRC-5 cells by nearly 6-fold (FIG. 2). By 8 to 24 hours expression of E1a in the transformed cells greatly exceeds the expression of E1a in MRC-5 cells by (40-fold to 70-fold). These results further demonstrate that the transcription of E1a is more efficient in tumor cells than non-transformed cells resulting in early and abundant expression of E1a in tumor cells after infection with Ad5.

Figure 3:
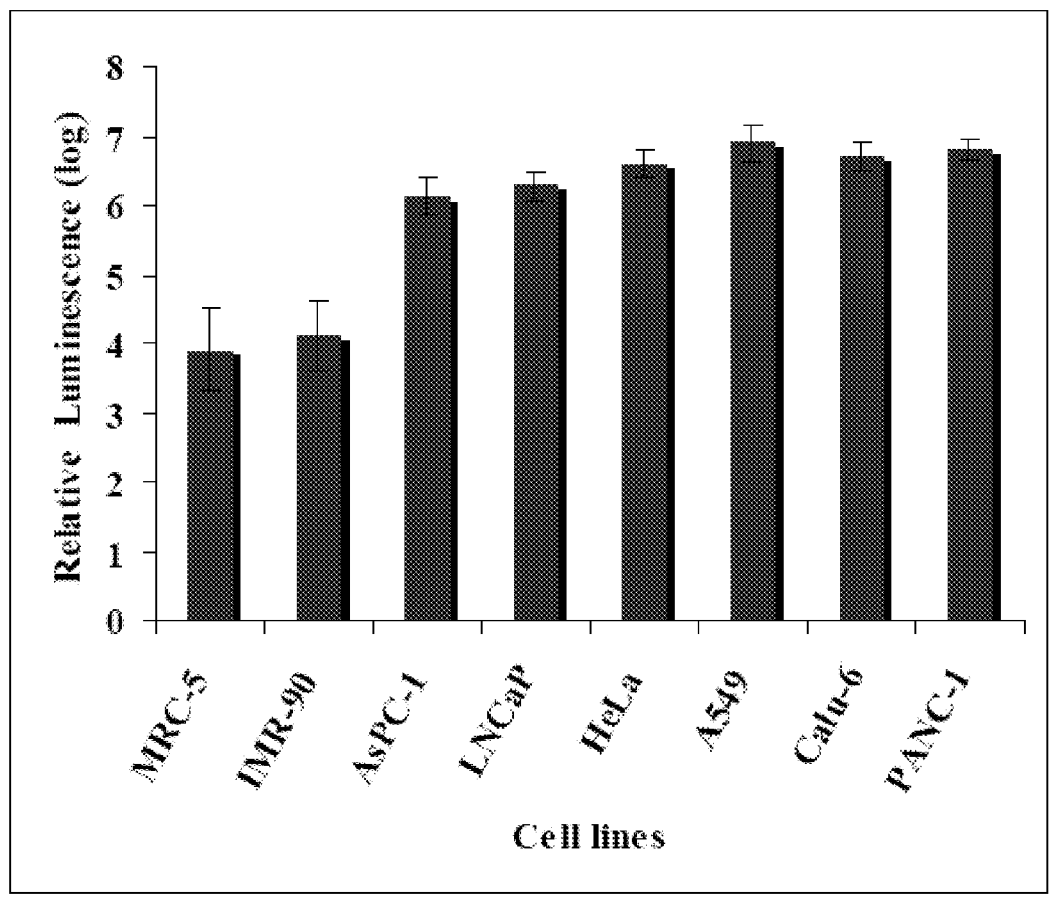
FIG. 3. Expression of luciferase from a reporter plasmid (pE1P/EGL3), driving by adenovirus E1A promoter/enhancer (+143 to +552). Cells were transfected with reporter plasmid, and luminescence values from each cell lines were obtained. Results are an average of duplicate samples and are representative of three independent experiments. Luminescence values (log) are indicated on the Y-axis, and cell lines are indicated on the X-axis.

To further evaluate the transcription from the E1a enhancer/promoter, a plasmid reporter with luciferase in place of E1a was transfected into transformed and non-transformed cells. Luminescence was quantified at 24 and 48 hours after transfection. Assays performed after 24 h of transfection resulted in no detectable luciferase expression in MRC5 cell lines while cancer cell lines showed 1000-fold enhancement of luciferase expression when compared to control values (data not shown). Detectable luciferase expression was observed in MRC-5 and IMR-90 (lung fibroblast) cells by 48 hours after transfection but remained approximately 100-1000 fold less than the luciferase expression in the cancer cell lines (FIG. 3). Renilla expression was also measured and served as a control to determine the transfection efficiency between cell lines.

Figure 4A:
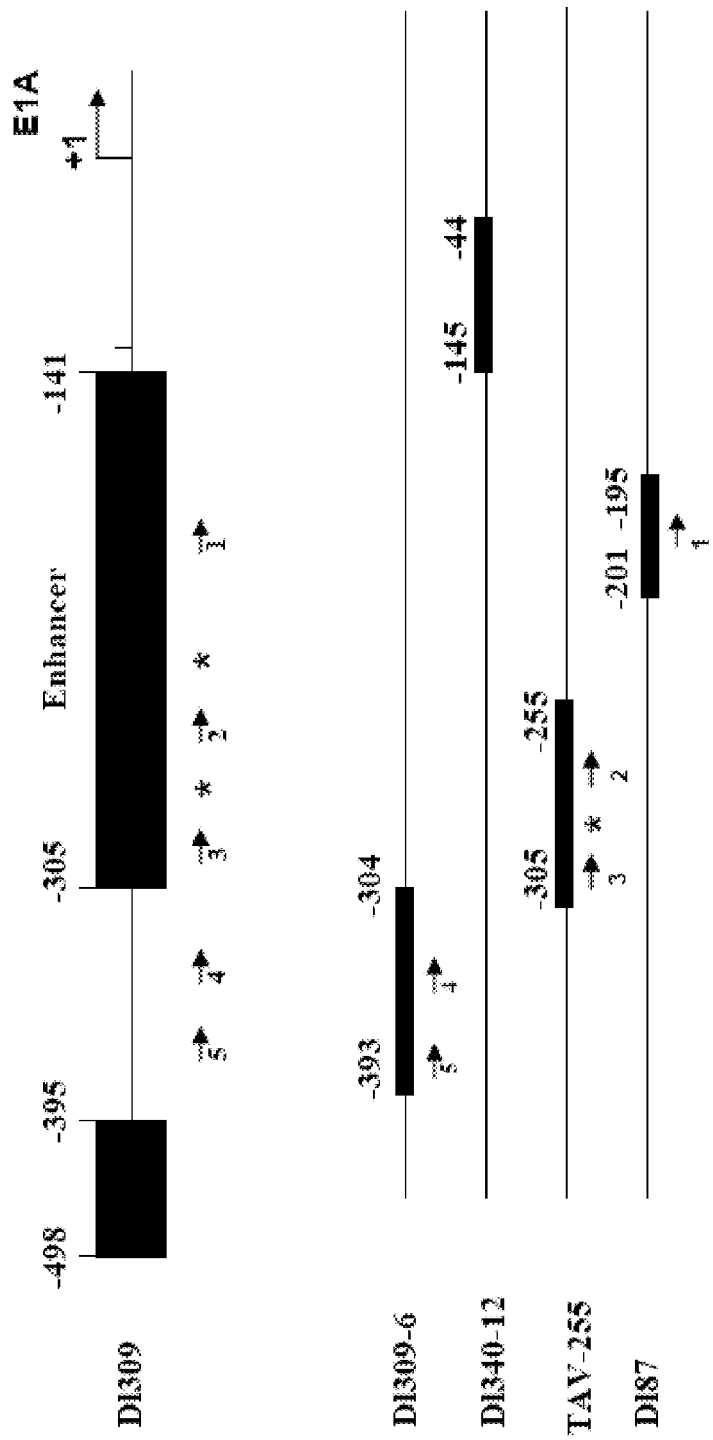
FIG. 4. (a) Schematic presentation of upstream control region of Ad5 E1A transcription units. Transcription start site (+1), enhancer region (−305 to −141), and ITR region (−498 to −395) are indicated at the top. Transcription factors binding sites for Pea3 and E2F1 are indicated by small arrow and star, respectively. Deletion mutant viruses and their encompassing nucleotides deletion are indicated by solid bar and region is indicated on their top. The name of each mutant virus is indicated to the left of their schematic diagram. (b) Expression of E1A protein in MRC-5 and A549 cells infected with Wt Ad5 and mutant viruses. Cells were infected with individual virus with an MOI of 5 and proteins were harvested 24 h.p.i. Various splice variant of E1A with amino acids residues (R); 289R, 243R, and 55R are shown by arrow. β-tubulin (loading control) are indicated next to the western blots. Cell lines are indicated left to each blot. (c) Time course assay for E1A expression by Wt Ad5 and TAV-255 in MRC-5 and A549 cells. Cells were infected with MOI of 5 and proteins were harvested at indicated hours post infection. Viruses are indicated on the top of solid line, and the various splice variant of E1A protein with amino acids residues (R): 289R, 243R, and 55R are shown by arrow. β-tubulin (loading control) are indicated next to the western blot.
Figure 4B:
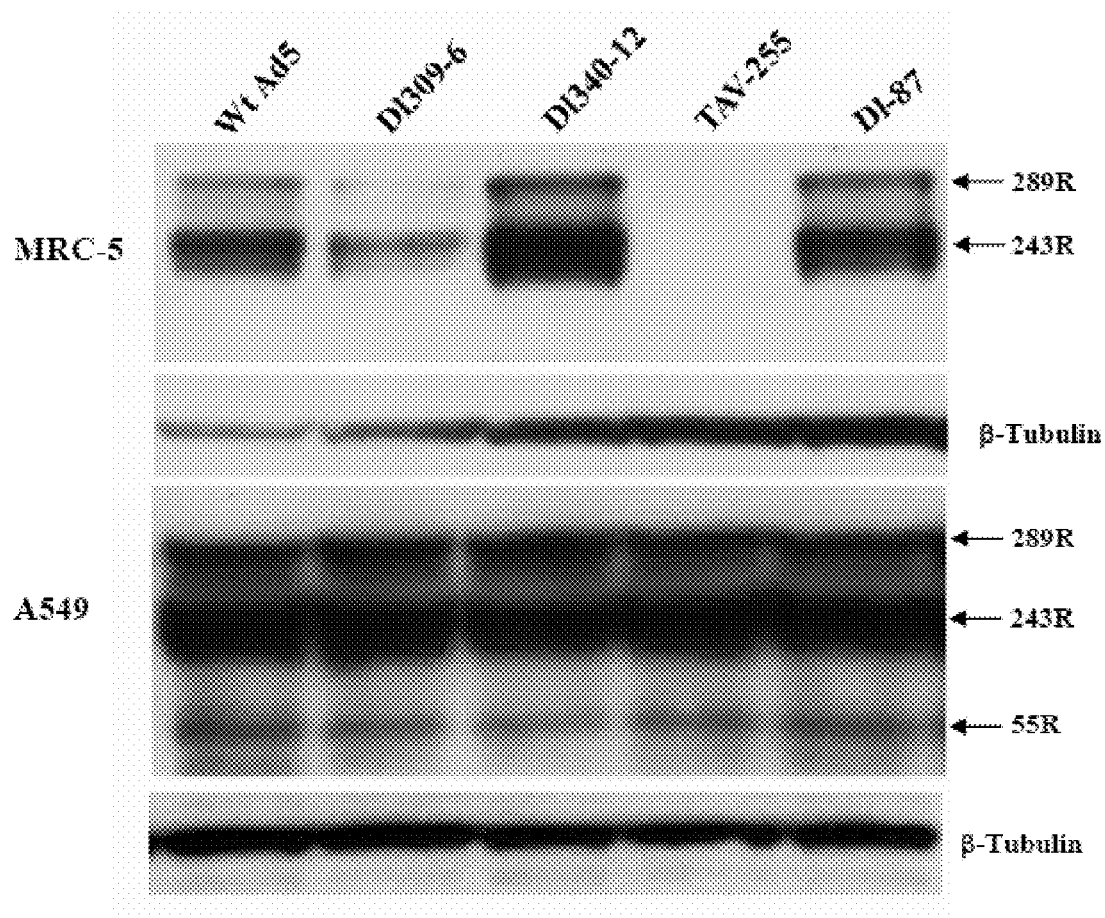
Figure 4C:
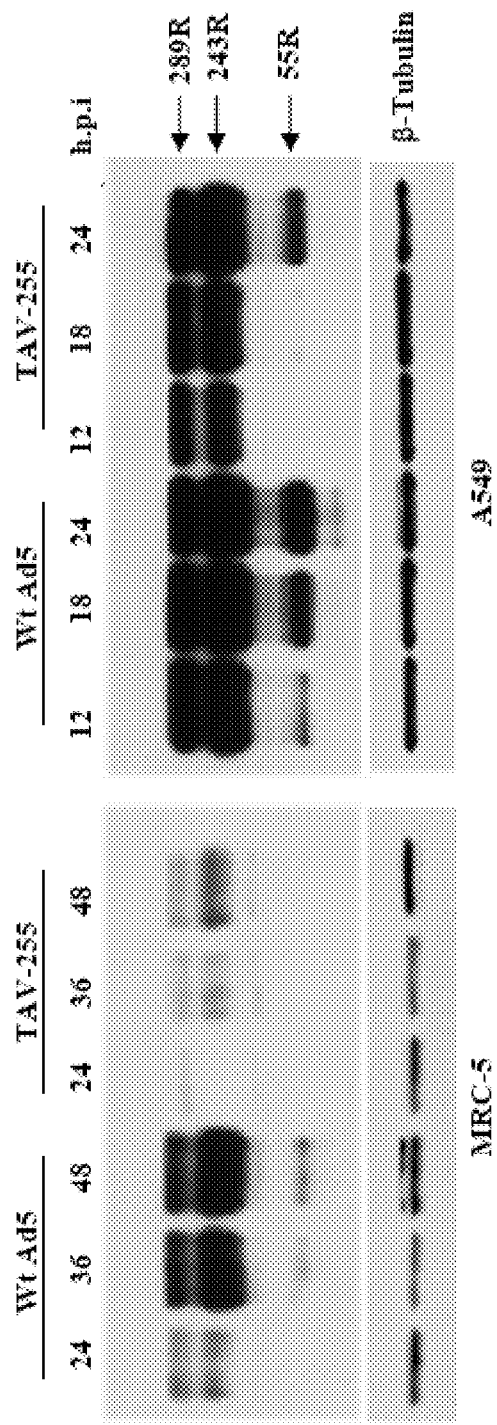

Deletion mutants of E1A transcription control region were prepared, and E1A expression in tumor and non-transformed cells was analyzed. To determine if there were differences between the transcriptional control of E1a between tumor and non-transformed cells, we evaluated E1a expression in tumor and non-transformed cells using adenoviral constructs with various deletions in the upstream control region for E1a, FIG. 4a. The results of E1a expression in non-transformed cells (MRC-5) and transformed cells (A549) from each of these deletion vectors is shown in FIG. 4b. The results demonstrate that none of the deletions had a significantly impact on E1a expression in A549 cells. However, deletion mutant viruses, dl309-6 and TAV-255, resulted in reductions in E1a expression in MRC-5 cells. Notably, the deletion spanning the region from −305 to −255, resulted in almost complete loss of E1a expression from MRC-5 cells but had no measurable impact on E1a expression from A549 cells. This deletion provided the greatest differential expression of E1a between the non-transformed and transformed cells. To further evaluate this effect, we compared the expression of E1a protein over time following infection of MRC-5 and A549 cells with wild-type Ad5 and TAV-255, FIG. 4c. These results demonstrate abundant E1a expression in A549 cell lines following infection with both vectors. However, expression of E1a was dramatically reduced in the non-transformed MRC-5 cells following infection with TAV-255.

Figure 5:
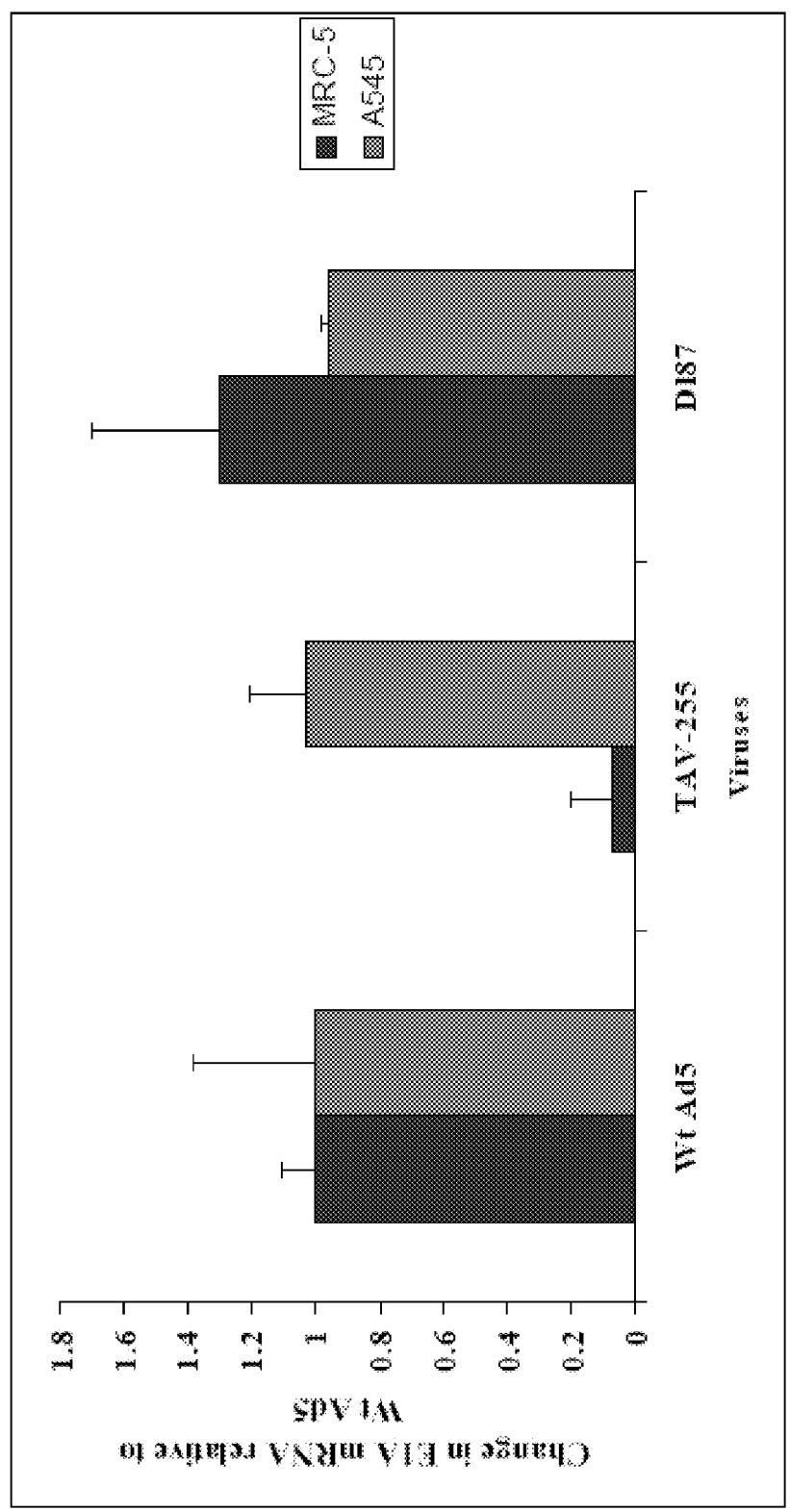
FIG. 5. Induction of E1A mRNA in infected (a) MRC-5 and (b) A549 cell (MOI 5) at 24 h post infection was determined by real time Q-PCR. E1A expression, fold increase or decrease, was calculated relative to Wt Ad5.

E1A mRNA expression from enhancer mutants was analyzed by Quantitative-PCR. We further characterized the expression of E1a mRNA following infection of MRC-5 and A549 cells with wild-type Ad5, TAV-255, and dl87, which has a deletion that removes the single Pea3 site located most proximal to the E1a start site. E1a mRNA expression was 20-30 fold reduced in MRC-5 cells infected with TAV-255 compared to Ad5 wild-type and dl87. However, E1a mRNA expression is approximately equivalent in A549 cells infected with each of these viruses (FIG. 5).

Figure 6A:
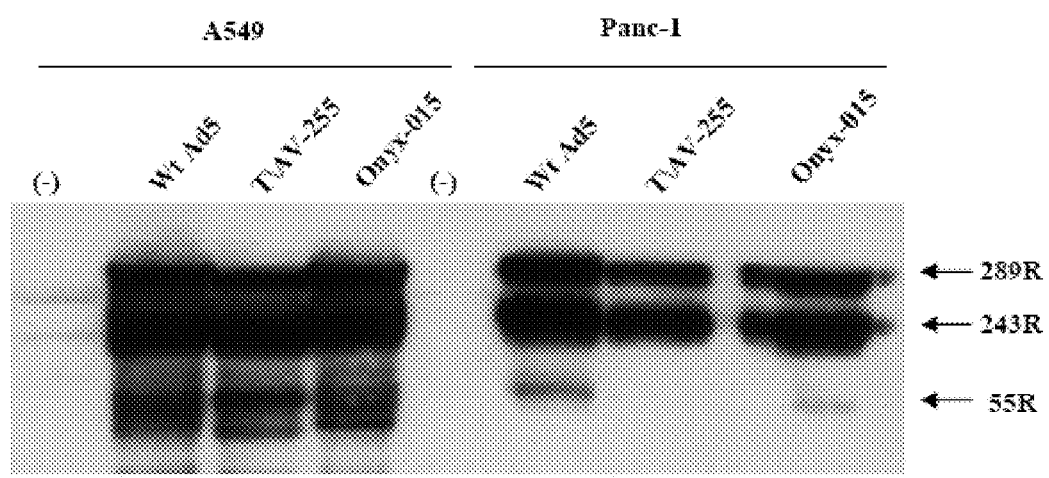
FIG. 6. Western blot analysis of Adenoviral E1A and E1b proteins in cell lines infected with various adenoviruses. (a) Cancer cell lines (A549 and Panc-1) were infected with viruses with a MOI of 5 and proteins were collected 24 h.p.i. Small arrows indicate expression of splice variants of E1A, viruses are indicated on the top of blot, and cell lines are indicated on the top of solid bar. (b) Western blot analysis of Adenoviral E1B-55 kDa protein in MRC-5 and A549 cells infected (MOI 5) with Wt Ad5, Onyx-015 and TAV-255. Protein samples were collected 24 h.p.i. and probed with E1B monoclonal antibody. Small arrow indicates the correct size of E1B 55 kDa protein; other bands are non-specific. Viruses are indicated on the top of the blot.
Figure 6B:
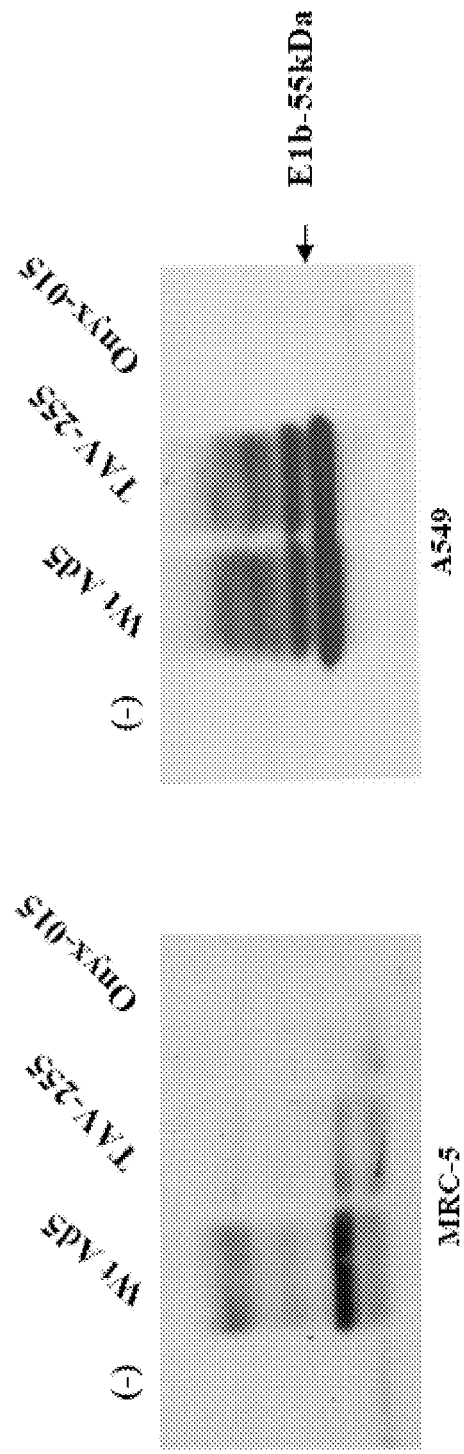

Onyx-015 and TAV-255 were compared with regards to expression of E1a and E1b. Onyx-015 has a deletion of the E1b-55k viral gene but has no modification to restrict E1a expression in non-transformed cells. FIG. 6a demonstrates comparable levels of E1a expression in A549 and Panc-1 cells infected with Ad5, TAV-255 and Onyx-015. To determine the impact of TAV-255 on the expression of E1b, we evaluated protein expression in MRC-5 and A549 cells. The results, shown in FIG. 6b demonstrate that the expression of E1b from TAV-255 was diminished in MRC-5 cells compared to Ad5. Onyx-015, which has a deletion of E1b-55k, has no detectable E1b expression. In contrast, E1b-55k is expressed at similar levels in tumor cells from both Ad5 and TAV-255 and is absent in the tumor cell lines infected with Onyx-015. These results demonstrate functional attenuation of E1b expression in non-transformed cells while expression of E1b is retained at approximately wild-type levels in tumor cells.

Figure 7A:
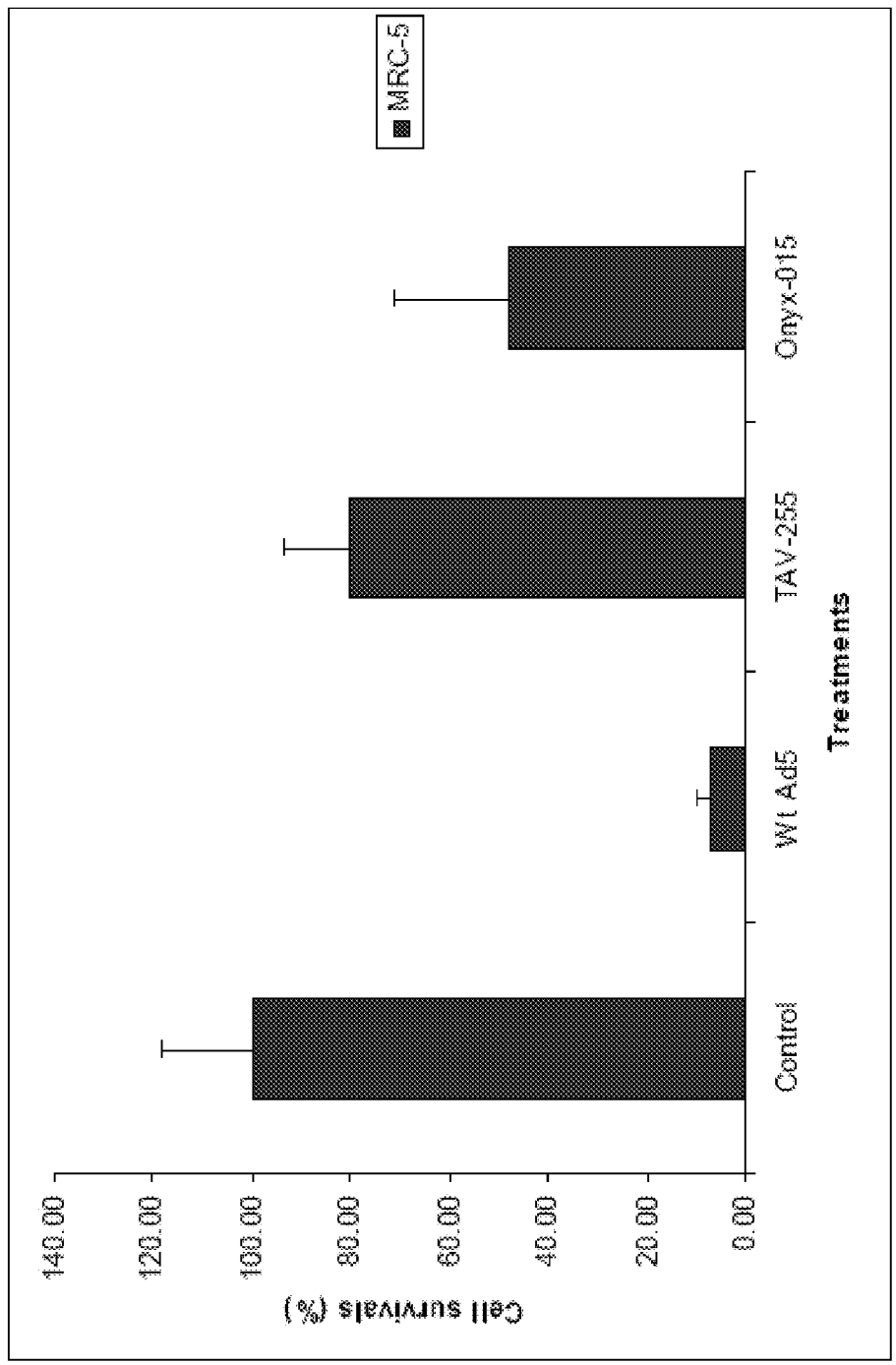
FIG. 7. Growth inhibition of normal cells and tumor cells by Ad 5 mutants. (a) Normal cell line MRC-5 and (b) tumor cell lines (A549, HeLa and Calu-6) were infected with Wt Ad5/TAV-255/Onyx-015 at a MOI of 5, and cell viability assay was performed using CCK-8 after 6 days post-infection. Results represents mean+/−SD (error bar) of triplicates experiments and expressed as PBS treated control cells. (c) MRC-5 cells were infected with Wt Ad5 or TAV-255 with a MOI of 5, and PBS treated cells served as control. Virus treated and untreated (control) cells were photographed 6 days post infection.
Figure 7B:
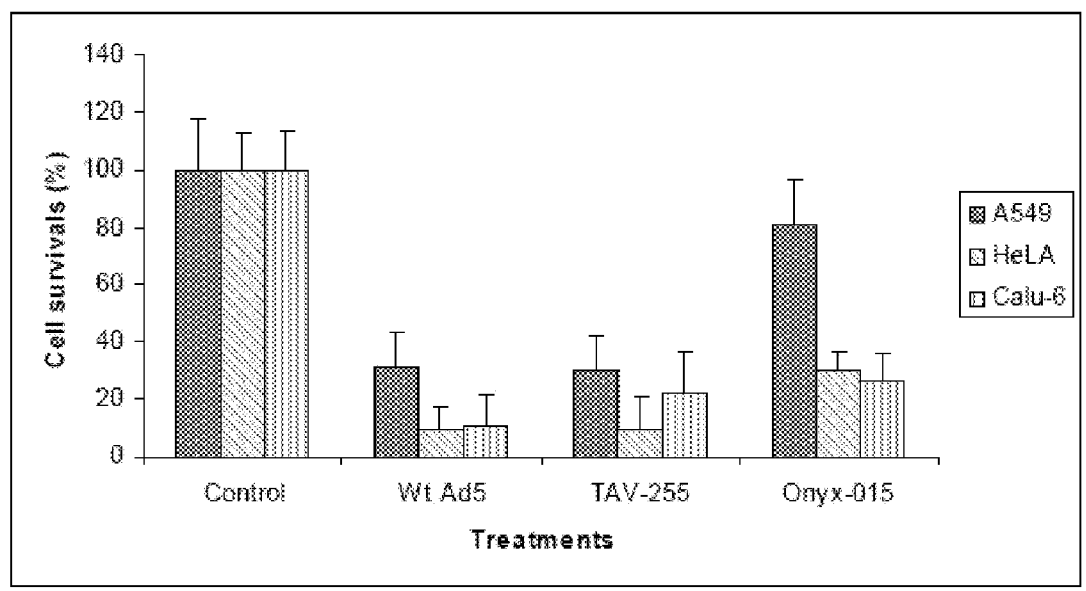

We evaluated the effect of TAV-255 on cell viability. MRC-5, A549, HeLa and CaLu-6 cells were infected with wild-type Ad5, Onyx-015, and TAV-255. Wild-type Ad5 effectively killed MRC-5 cells in this assay; where as both Onyx-015 and TAV-255 demonstrated minimal cytotoxicity towards MRC-5 cells (FIG. 7a). In contrast, cytotoxicity of TAV-255 was comparable to wild-type Ad5 in three tumor cell lines (A549, HeLa and CaLu-6) and was significantly better than the Onyx-015 in both A549 and HeLa cells (FIG. 7b). A photomicrograph of MRC-5 cells infected with wild-type and TAV-255 viruses (FIG. 7c) demonstrates essentially complete cell killing of MRC-5 cells with wild-type Ad5 while minimal cytotoxicity is observed with TAV-255, 6 days post-infection. Complete cytotoxicity was observed for A549 cells infected with either Wt Ad5 or TAV-255 (data not shown).

ONYX-015 is the prototype of an oncolytic virus and has undergone clinical testing in a variety of malignancies including head and neck, lung, colorectal, ovarian, pancreatic and brain cancers. Over 1000 intratumoral injections of ONYX-015 were administered to patients with head and neck tumors and over 200 infusions were administered into the hepatic artery of patients with metastatic colorectal cancer without serious treatment related adverse events (Reid, T. et al., Cancer Res 62(21):6070-6079 (2002); Nemunaitis, J. et al., Gene Ther 8(10):746-759 (2001); Khuri, F. R. et al., Nat Med 6(8):879-885 (2000); Nemunaitis, J. et al., Cancer Gene Ther 10(5):341-352 (2003); Nemunaitis, J. et al., Cancer Gene Ther 14(11):885-893 (2007) Reid, T. R. et al., Cancer Gene Ther 12(8):673-681 (2005)). The primary side-effects were grade I/II flu-like symptoms including fevers and chills. While well tolerated, objective response rates to ONYX-015 were restricted to a minority of patients. Since the objective response rates to ONYX-015 were modest, efforts have been directed at developing an oncolytic vector with improved potency (Kim D. Oncogene 19(56):6660-6669 (2000); Li, Y. et al., Clin Cancer Res 11(24 Pt 1):8845-8855 (2005); Johnson, L. et al., Cancer Cell 1(4):325-337 (2002); Hermiston, T. Current opinion in molecular therapeutics 8(4): 322-330 (2006)). Various approaches have been used to improve the tumor-selectivity and potency of oncolytic viruses, including efforts to place E1a and E1b under the control of distinct tumor-specific heterologous promoters. However, these vectors have suffered from leaky transcription of E1a and E1b in non-transformed cells, recombination and low replicative potential compared to wild-type Ad5.

To overcome some of the limitations inherent in the use of heterologous promoters to control the expression of E1a and E1b, we focused our attention on analysis of the endogenous adenoviral promoter and enhancer for E1a. We found that the onset of E1a mRNA and protein expression occurred earlier and was more abundant in tumor cell lines than in respiratory epithelial cells. Early and abundant expression of E1a was observed in a variety of tumor cell lines including cell lines from lung, pancreas, cervical and prostate cancer. E1a protein could be detected by western blot 6 to 8 hours post infection in the panel of tumor cells tested. The abundance of E1a expression at 6 to 8 hours post infection was similar to the E1a expression observed in two non-transformed respiratory epithelial cell lines by 24 hours post infection.

To further evaluate the early and abundant expression of E1a in tumor cells, we studied the expression of E1a from viruses with various deletions in DNA sequence upstream of the E1a start site. Enhancer sequences potentiate transcription independent of position or orientation and have been described in a variety of systems including adenovirus (Hearing, P. et al., *Cell* 33(3):695-703 (1983)). Core sequences were identified 200 to 300 nucleotides upstream of the E1a start site that could potentiate the expression of E1a independently of position or orientation (Hearing, P. et al., *Cell* 33(3): 695-703 (1983)). Previous studies have demonstrated that deletions of this core enhancer sequence resulted in a 2 to 5-fold decrease in mRNA expression in HeLa cells 5 hours post infection; however, these deletions had little impact on mRNA expression by 24 hours post-infection and had no impact on viral replication (Hearing, P. et al., *Cell* 33(3):695-703 (1983)). However, the previous analysis of the E1a enhancer was performed in tumor cells, primarily HeLa cells, rather than in respiratory epithelial cells, the natural host cells for adenoviral type 5 infections. Specific transcription factor binding sites within the Ad5 enhancer region include 2 binding sites for E2F1 and 5 binding sites for Pea3. Since these transcription factors commonly over expressed in tumor cells important functions of the E1a enhancer may have been obscured by analysis of the enhancer in the context of tumors cells rather than respiratory epithelial cells.

We have extended the analysis of the enhancer region of adenovirus by comparing the impact of deletions within the region upstream of the E1a start site on the expression of E1a in tumor cells and in non-transformed respiratory epithelial cells. Consistent with the previous publications, we find that deletions of large regions of the E1a enhancer region have little impact on E1a expression and viral replication in tumor cell lines (Hearing, P. et al., *Cell* 33(3):695-703 (1983)). However, we now demonstrate that various deletions, including deletions outside the previously defined enhancer region, have a significant impact on E1a expression and viral replication in non-transformed respiratory epithelial cells. In particular, we found that deletion of a 50 base-pair sequence of the native Ad5 enhancer that removes one E2f1 site and two Pea3 sites resulted in marked suppression of E1a and E1b mRNA and protein expression in respiratory epithelial cells; however, this deletion had little impact on the expression of E1a in a panel of tumor cell lines. We further demonstrate that deletion of a 99 nucleotide sequence upstream of the proposed E1a enhancer substantially reduces the expression of E1a in non-transformed respiratory epithelial cells while having a minimal impact on the expression of E1a from the tumor cell lines tested. This region encompasses the two Pea3 sites furthest upstream of the E1a start site. In contrast, a small deletion that removes the Pea-3 site most proximal to the E1a start site, had no significant impact on E1a expression in the tumor cells or in the respiratory epithelial cells. Furthermore, a 101 nucleotide deletion from the regions between the enhancer and the E1a start-site results in a 22 to 30% increase in E1a expression in respiratory epithelial cells without significantly impacting E1a expression from tumor cells. These results demonstrate that deletions involving the enhancer region have profound effects on E1a expression in respiratory epithelial cells that are not observed in tumor cells. Thus, the adenoviral E1a enhancer region is more complex and spans a larger region when analyzed in respiratory epithelial cells instead of tumor cells.

The 50 nucleotide deletion of the spanning the region from −255 to −305 encompasses two binding sites for Pea3 and one binding site for E2f1 (Bruder, J. T. et al., *J Virol* 65(9):5084-5087 (1991)). These transcriptions factors are commonly over-expressed in a wide variety of tumors. E2f is a sequence specific transcription factor that forms a complex with Rb and plays critical roles in regulating cell cycle progression and cellular differentiation. Phosphorylation of RB by cyclin-dependent kinases results in release of E2F1 and transcriptional activation of genes involved in DNA replication, repair and recombination (Johnson, D. G. et al., *Front Biosci* 3:d447-448 (1998); Muller, H. et al., *Biochimica et biophysica acta* 1470(1):M1-12 (2000)). Deregulation of the RB pathway occurs commonly in malignancies and approaches 100% in various tumors including lung cancer (Hanahan, D. et al., *Cell* 100(1):57-70 (2000)). Two binding sites for E2F1 occur in the control region for E1a. The deletion encompassing the two Pea3 sites furthest from the E1a start site had only a moderate impact on E1a expression. However, deletion of the distal E2F site along with the two Pea3 sites immediately flanking the E2F1 site results in significant reduction in expression of E1a, E1b and viral replication in the non-transformed cells. These results suggest that the E2F1 and/or the Pea3 sites located within this 50 base pair fragment are the dominant sites for E1a control in respiratory cells or that additional factors impacted by this deletion determine E1a expression.

Pea3 is a member of the highly conserved Ets transcription factor family (de Launoit, Y. et al., *Biochimica et biophysica acta* 1766(1):79-87 (2006)). Pea3 is normally expressed during embryogenesis and is involved in tissue remodeling events, cell differentiation and proliferation. Pea3 transcriptionally activates a variety of genes including matrix metalloproteases (MMPs), which function to degrade the extracellular matrix during normal remodeling events. Pea3 is commonly over-expressed in a variety of cancers including breast, lung, colon, ovarian and liver cancer where over-expression of MMPs are thought to promote metastasis (de Launoit, Y. et al., *Adv Exp Med Biol* 480:107-116 (2000); Hakuma, N. et al., *Cancer Res* 65(23):10776-10782 (2005); Boedefeld, W. M., $2^{nd}$ et al., *Mol Carcinog* 43(1):13-17 (2005); Cowden, D. et al., *Mol Cancer Res* 5(5):413-421 (2007)). Previous studies have demonstrated that cooperative binding between the Pea3 sites increases E1a expression (Bruder, J. T. et al., *J Virol* 65(9):5084-5087 (1991)). Consequently, the impact of specific transcription factor binding sites and cooperativity between these binding sites may be more evident in non-transformed cells where the transcription factors are limiting than in tumor cells where abundant expression of transcription factors may override the need for cooperative binding to enhance transcription of E1a. The relative importance of the various transcription factor binding sites, alone and as a complex, is under further investigation.

Our results further demonstrate that tumor-selective expression of the E1b transcription unit can be achieved by modification of the E1a enhancer. The E1b promoter is relatively simple promoter comprised of at TATA box and a GC box, which binds the sequence specific transcription factor SP-1. Both domains are necessary for efficient expression of E1b (Wu, L. et al., *Nature* 326(6112):512-515 (1987)). Previous studies have demonstrated that E1b is expressed as a read-through transcript from E1a (Montell, C. et al., *Mol Cell Biol* 4(5):966-972 (1984)). Termination of read-through transcription of E1b from E1a by insertion of the beta-globin termination sequence resulted in markedly diminished expression of E1b (Maxfield, L. F. et al., *J Virol* 71(11):8321-8329 (1997); Falck-Pedersen, E. et al., *Cell* 40(4):897-905

(1985)) while insertion of a strong promoter such as the CMV promoter obviates the need for read-through transcription. Our findings demonstrate that expression of E1b can be coordinately attenuated in the non-transformed respiratory epithelial cells along with E1a due to the small deletion in the E1a enhancer. These results are consistent with inefficient read-through transcription of E1b in non-transformed cells. In contrast, both E1a and E1b are expressed at near wild-type levels in A549 cells, indicating efficient read-through transcription from E1a in the tumor cells.

Since E1b 55k is a multifunctional protein critical for viral replication, tumor-selective attenuation of the expression of this protein rather than deletion of this gene may improve the potency of this virus in tumor cells while retaining a high-degree of attenuation in non-transformed cells due to decreased expression of both E1a and E1b. We compared the oncolytic activity of TAV-255 to ONYX-015 in tumor and normal cells and found that TAV-255 is more potent in inducing cell lysis in tumor cells than ONYX-015 while retaining a similar level of attenuation as ONYX-015 in non-transformed cells.

Deletion of E2F sites present at −225 and −287, relative to E1a transcription start site designated as +1, had no impact on E1a expression in transformed cells (Bruder, J. T., and Hearing, P. (1989). Nuclear factor EF-1A binds to the adenovirus E1A core enhancer element and to other transcriptional control regions. Mol Cell Biol 9: 5143-5153). The binding sites for Pea3 are located at −200, −270, −300, −344, −386 and deletion of Pea3 binding sites I, II, and III alone had minimal impact on E1a expression in HeLa cells (Hearing, P., and Shenk, T. (1983). The adenovirus type 5 E1A transcriptional control region contains a duplicated enhancer element. *Cell* 33: 695-703). Previous studies defined the importance of E1a transcriptional control region in transformed cell lines. However, tumor cells differ significantly from non-transformed cells, the natural host for the virus. Tumor cells are actively proliferating and have abnormal expression of many signal transduction, cell regulatory and apoptotic pathways. Various transcription factors including E2F and Pea3, which bind to the E1a transcription control region, are aberrantly expressed in tumor cells (de Launoit, Y., et al. (2000). The PEA3 group of ETS-related transcription factors. Role in breast cancer metastasis. Adv Exp Med Biol 480: 107-116; Hanahan, D., and Weinberg, R. A. (2000). The hallmarks of cancer. Cell 100: 57-70). E1a expression Therefore, control of E1a transcription study could be affected in tumor cells by the altered expression of these transcription factors.

Understanding of the function of the E1a enhancer in vitro in tumor cells may be more revealing when the regulation of E1a in tumor cells is compared to the regulation of E1a in non-transformed human cells. Human diploid fibroblasts (MRC-5, WI-38 and IMR-90) have been used extensively for several decades as standard laboratory cell lines in vaccine development, diagnostic virology, and research laboratories to culture and study a wide range of viruses including adenovirus, herpes virus, cytomegalovirus, and many others (Friedman, H. M., and Koropchak, C. (1978). Comparison of WI-38, MRC-5, and IMR-90 cell strains for isolation of viruses from clinical specimens. J Clin Microbiol 7: 368-371). We made a series of deletion in Had-5 E1a transcriptional control region to determine the role of the DNA element which binds Pea3 and E2F, and compared the expression of E1a in a panel of transformed and non-transformed cell lines. We propose that the E1a enhancer sequence, when evaluated in the context of non-transformed cells, is larger and more complex than what was previously reported. We discuss the potential of HAd-5 mutant virus as a potent oncolytic agent.

III. Investigation of Binding Site Deletions

Deletion mutants of HAd-5 E1a transcriptional control region were prepared, and expression of E1a in non-transformed and transformed cells was investigated. The HAd-5 transcription control region contains binding sites for multiple transcription factors, many of which are over expressed in cancer cells. Consequently, the use of transformed cells to study E1a transcription will be affected by aberrant expression of various transcription factors that influence these critical regulatory sequences. To overcome this limitation, we have utilized growth arrested human lung epithelial cell lines to study E1a gene expression and compared these results to E1a expression in a panel of tumor cell lines. Various deletion mutants were generated targeting specifically Pea3 and E2F binding sites. FIG. 8a demonstrates the binding sites for Pea3 and E2F and deletion mutants spanning these transcription factors sites. These deletion mutants were made in the plasmids and introduced into the HAd-5 genome through homologous recombination. HAd-5 mutant viruses carrying these mutations were used to infect MRC-5 (non-transformed pulmonary) and A549 (transformed pulmonary) cells and were then analyzed for E1a gene expression by western blot (FIG. 8b) and Q-PCR (FIG. 8c). In non-transformed cells, dl309-6, which removes the Pea3 sites number IV and V, demonstrated reduced E1a protein expression compared to Wt HAd-5 (dl309). Deletion mutant, dl87, which removes Pea3 site number I and dl275 which removes the E2F binding site showed no difference in E1a expression compared to Wt HAd-5. TAV-255, which removes Pea3 site number II and III along with the E2F located between the two Pea3 sites, and dl55, which removes the Pea3 site number II, did not demonstrate detectable expression of E1a protein by 24 hours post infection (h.p.i.). A minor band present in lanes corresponding to TAV-255 and dl55 is similar to band present in control lane, suggesting non-specific reaction with E1a antisera. Relative Q-PCR performed from mRNA extracted at 24 h.p.i. suggested that dl309-6 expressed 2.5 fold less E1a mRNA in compared to Wt HAd5 whereas dl87 deletion had no significant effect on E1a gene expression. Mutant dl275 showed 20 percent reduction in E1a mRNA in compared to Wt HAd-5. Deletion mutant, dl55, showed 10-fold reduction in E1a mRNA expression whereas TAV-255 showed 33-fold reduction in E1a mRNA expression compared to Wt HAd-5.

Figure 9:
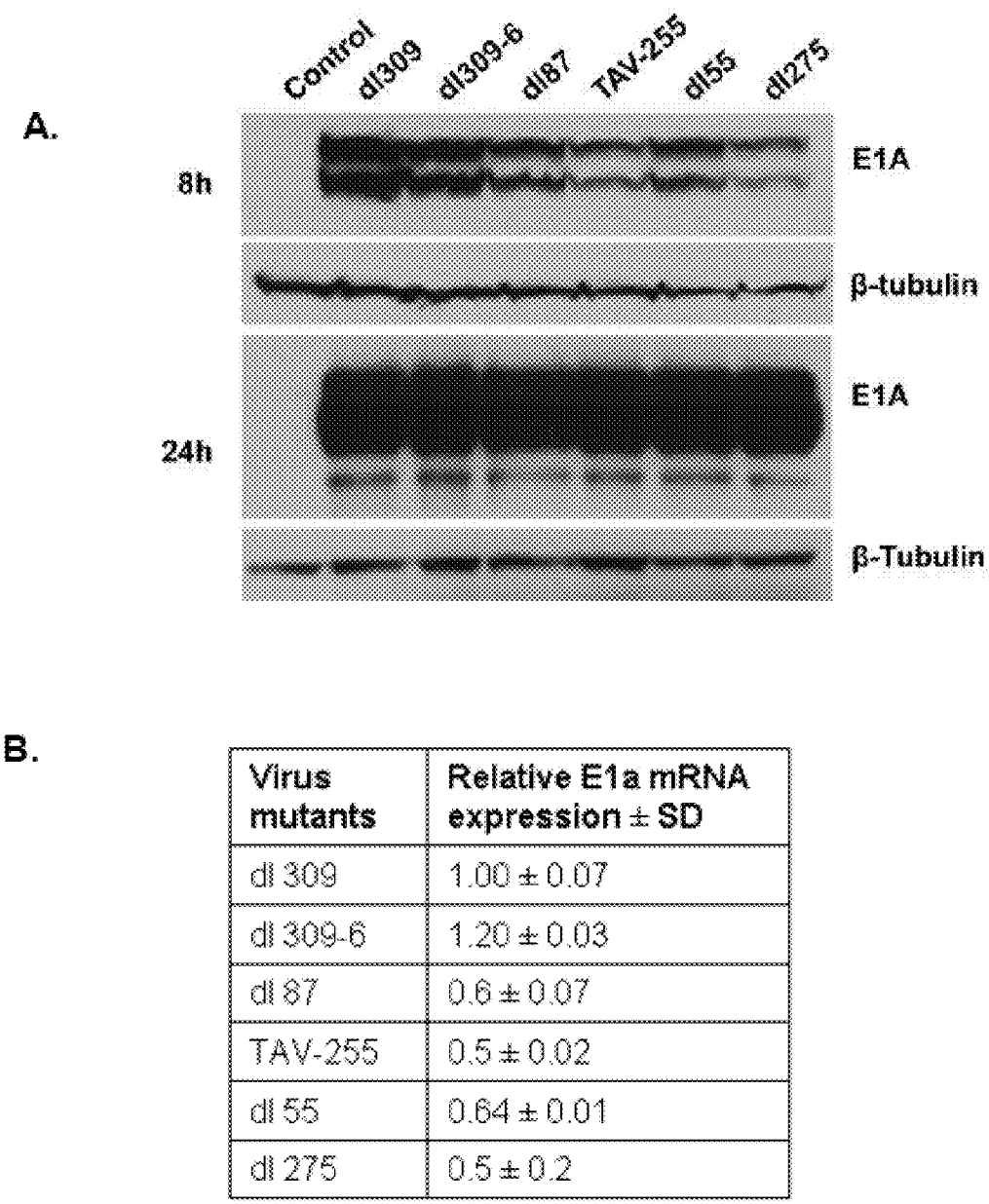
FIG. 9. Expression of E1a in A549 cells infected with mutant adenoviruses. (a) Cells were infected with mutant adenoviruses and protein was collected 8 and 24 h.p.i. and probed with E1a specific antisera; β-tubulin (loading control) is also shown. (b) Relative Q-PCR analysis of E1A mRNA produced in A549 cells infected with HAd-5 mutants at 8 h.p.i.

We compared the expression of the E1a mRNA and protein in A549 cells infected with these mutant viruses (as described in FIG. 8a) at 8 and 24 h.p.i. These results, shown in FIG. 9a, demonstrate a small decrease in E1a protein expression at 8 h.p.i. whereas these viruses did not show any significant difference in E1a expression after 24 h.p.i. Using Q-PCR analysis dl87, TAV-255, dl55, and dl275 showed approximately 2 fold reduction in E1a gene expression whereas mutant virus dl309-6 showed 20 percent increase in E1a expression in comparison with Wt HAd-5 after 8 h.p.i. (FIG. 9b).

Q-PCR performed after 24 h.p.i. showed no difference in E1a gene expression compared with Wt HAd-5 (data not shown). From these results it is evident that deletion mutant of E1a enhancer had greater impact on the E1a gene expression when studied in the context of MRC-5 cells compared to A549 cells. To further understand the role of nucleotides present within TAV-255, we made several 6 bp deletions within TAV-255 and reconstructed these mutations in HAd-5 genome and studied the E1a expression in non-transformed cell lines.

Figure 10:
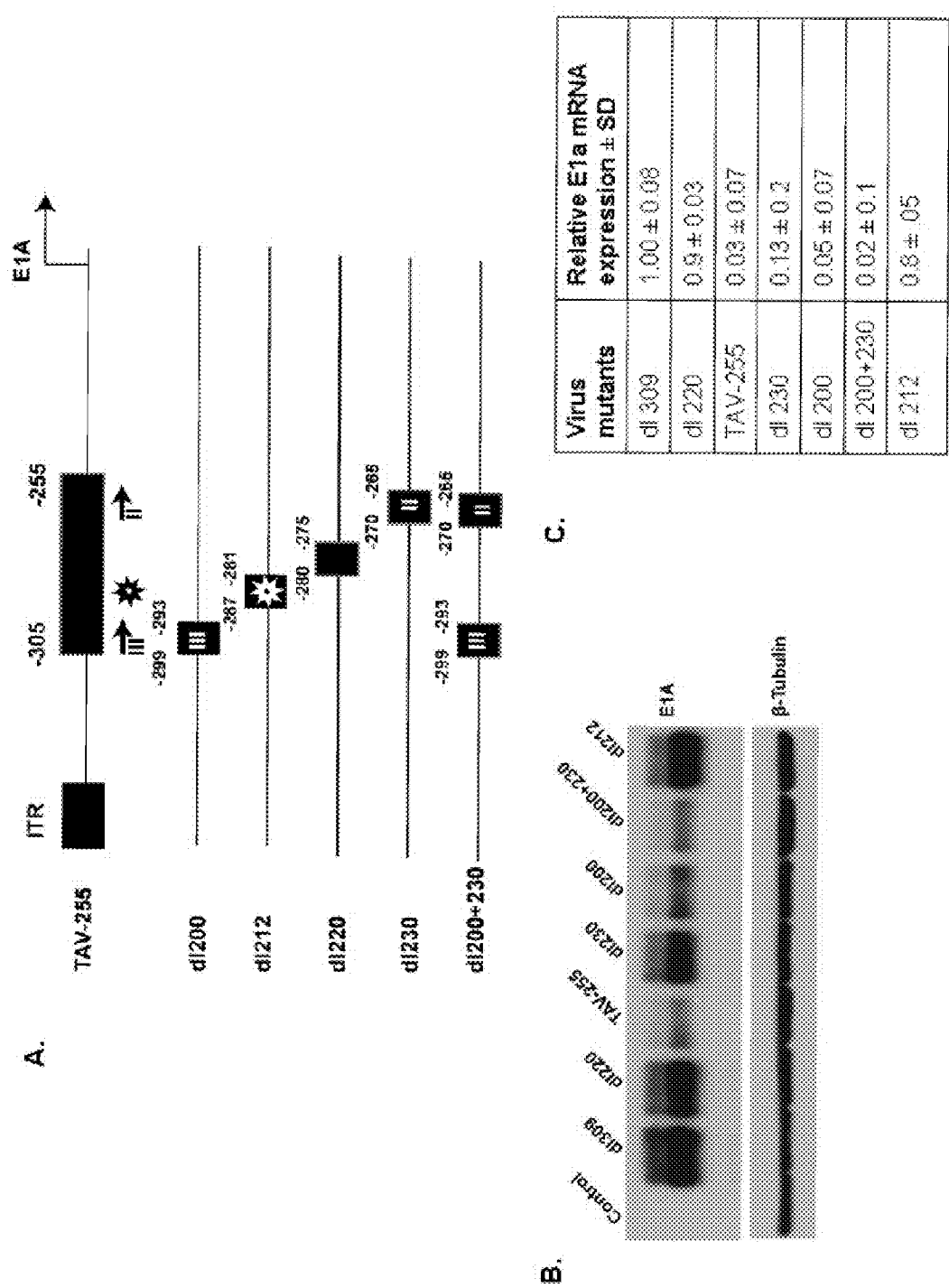
FIG. 10. Deletion mutant adenoviruses within TAV-255 and expression of E1a in MRC-5 cells. (a) Schematic presentation of TAV-255 encompassing one E2F1 site and two Pea3 site II and III. Six base pair deletion within TAV-255 is shown by solid black color and their encompassing nucleotides are indicated on the top. Each virus name is indicated left to the schematic diagram; dl200 removes Pea3 binding site III, dl212 removes E2F binding site, dl220 removes 6 bp nucleotide (as control), dl230 removes Pea3 binding site II, and dl200+230 removes Pea3 site II+III. (b) Western blot analysis of E1a protein expressed by various mutant viruses 48 h.p.i.; β-tubulin (loading control) is shown below E1a blot. (c) Relative Q-PCR analysis of E1a mRNA in cells infected with various adenovirus mutants at 24 h.p.i.

Deletion mutant, TAV-255, encompasses two Pea3 and one E2F transcription factor binding sites. To characterize the role of each regulatory element, we made deletion of the individual Pea3 and E2F elements and reconstructed these mutations in HAd-5 genome (FIG. 10a). A random 6 bp deletion (dl220) between two Pea3 sites was also generated as a control. E1a protein expression was determined for the mutant viruses and Wt HAd-5 at 48 h.p.i. in MRC-5 cells (FIG. 10b). Similar expression profiles of E1a were observed for TAV-255 and dl200+230, which have deletion of Pea3 binding sites number II and III. E2F deletion mutant (dl212) and control deletion mutant (dl220) had no significant effect on E1a expression compared to Wt HAd-5. Cells infected with mutant virus dl200+230, showed 50-fold reduction in E1a mRNA in comparison with Wt HAd-5 24 h.p.i. in Q-PCR analysis (FIG. 10c). TAV-255, which has deletion of Pea3 site number II+III along with E2F site had a 33-fold reduction in E1a expression. Deletion mutant, dl212, which removed the E2F site, had a 20 percent decrease in E1a gene expression. dl220 had no significant difference in expression of E1a compared to Wt HAd-5.

Figure 11:
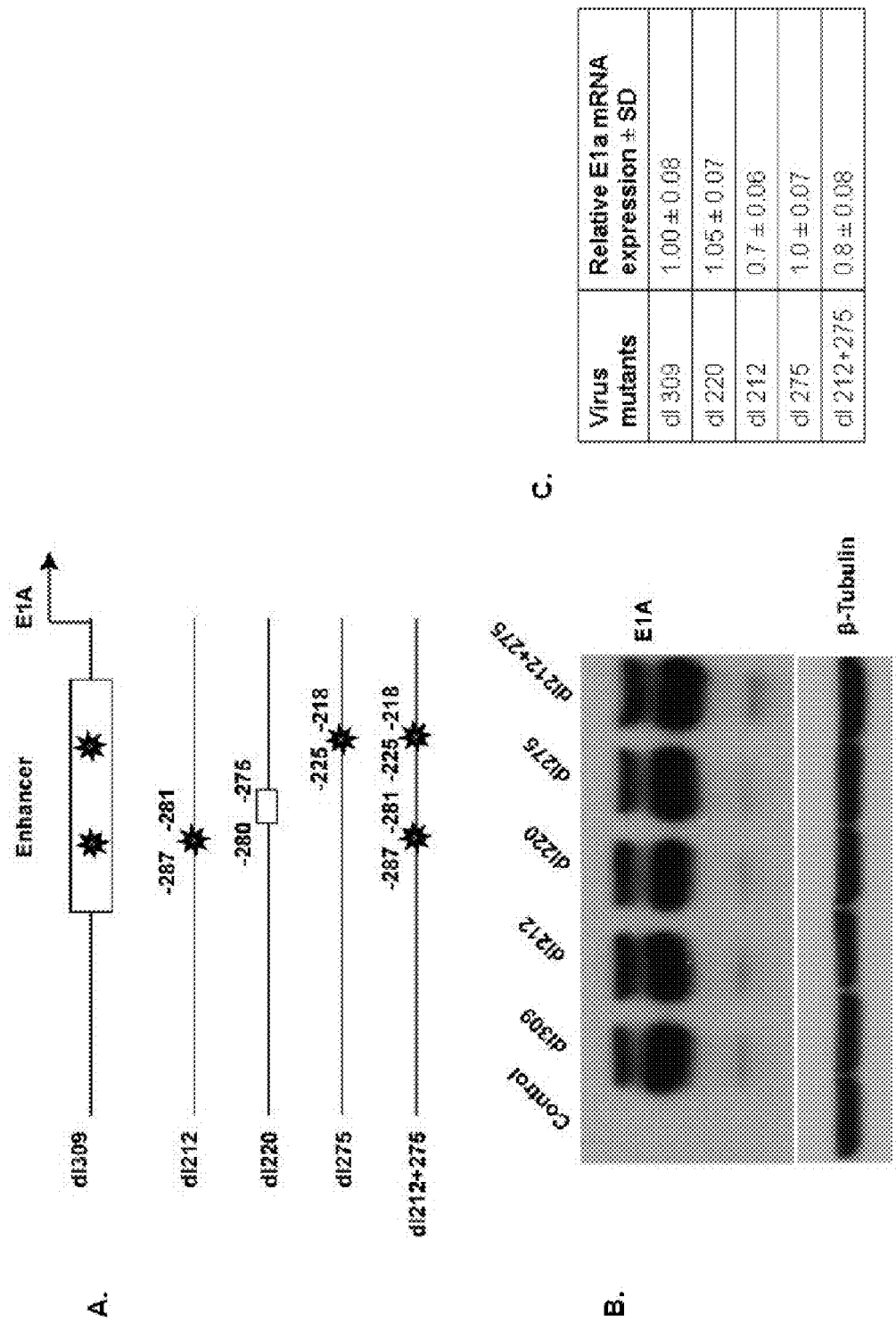
FIG. 11. Deletion mutant viruses of E2F and expression of E1a in MRC-5 cells (a) Schematic presentation of E2F sites shown as star in the E1a enhancer region and their encompassing nucleotides are shown on the top. Mutant virus names are indicated left to the schematic; dl212 and dl275 has single E2F site deletion, dl212+275 has both E2F sites deletion and dl220 is made as a control. (b) Western blot analysis of E1a protein expressed in cells infected with various adenovirus mutants 24 h.p.i.; β-tubulin is shown as a loading control. (c) Relative Q-PCR for E1a mRNA expression at 24 h.p.i. in cells infected with various adenovirus mutants.

To further evaluate the role of E2F sites present in the E1a enhancer element and their impact on E1a expression, we generated single and double mutation of E2F sites and studied the impact of these mutations on E1a expression. Adenovirus enhancer element contains two binding sites for E2F transcription factor at −225, and −287 (FIG. 11A). Individual E2F binding site as well as both sites together were mutated and reconstructed in HAd-5 genome by homologous recombination. E1a protein expression was studied in MRC-5 cells infected with mutant viruses at 24 h.p.i. (FIG. 11B). These mutant viruses did not show any significant difference in E1a gene expression in comparison with Wt HAd-5, suggesting that E2F does not play a significant role in E1a gene expression in growth arrested MRC-5 cells. Q-PCR analysis performed at 24 h.p.i. showed 20 to 30 percent reduction with dl212 as well as dl212+275 mutant viruses whereas mutant virus dl275 did not show any reduction in E1a gene expression in comparison with Wt HAd-5 (FIG. 11C). Studies performed with these mutant viruses in transformed cell line (A549) did not result in any significant impact on E1a expression (data not shown).

Figure 12:
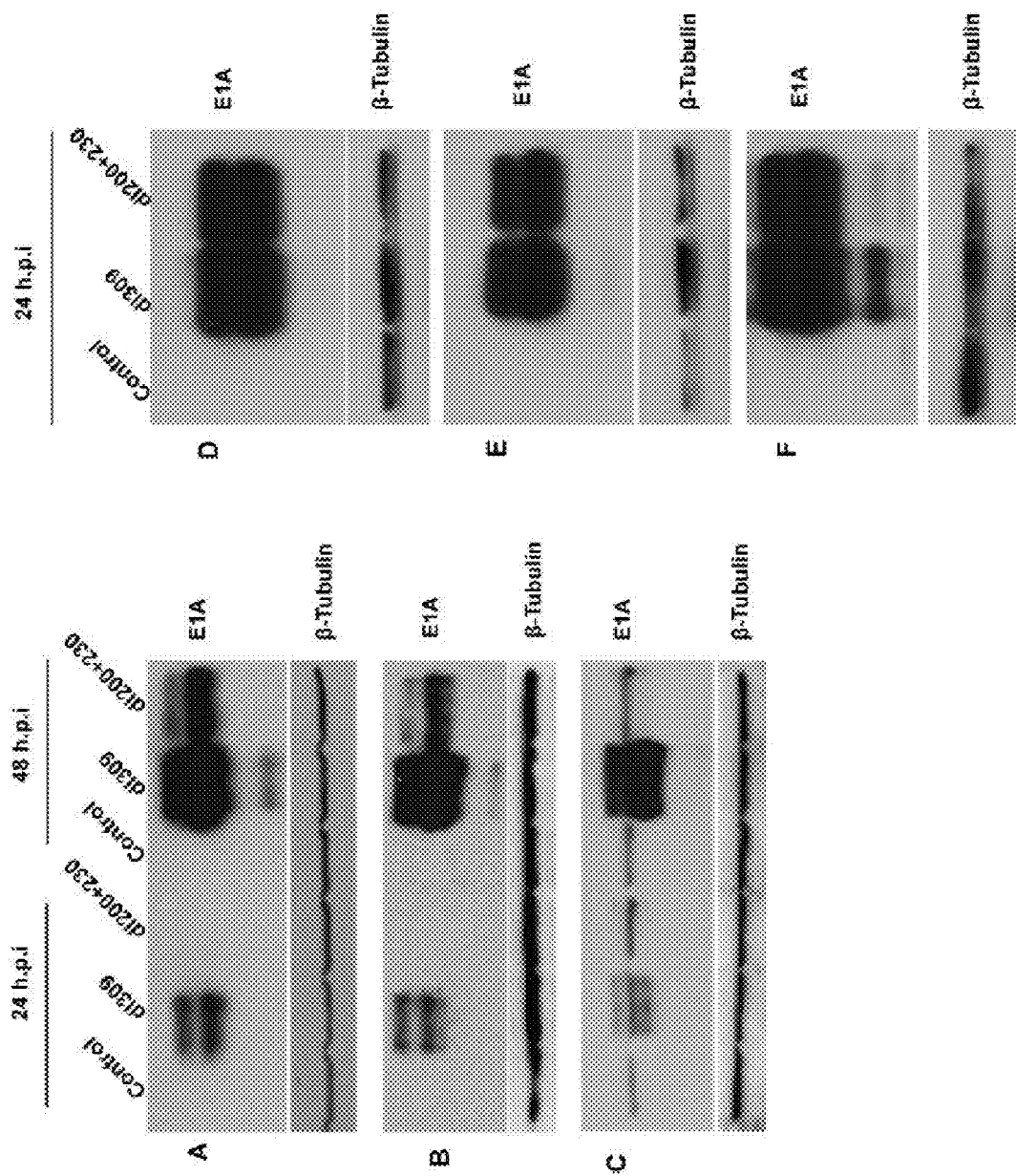
FIG. 12. Expression of E1a protein in various non-transformed and transformed cell lines infected with adenoviruses. (a) Non-transformed cell lines; (a) MRC-5, (b) IMR-90, and (c) WI-38 and (B) transformed cell lines; (e) HeLa, (f) Panc-1, and (g) Calu-6 were infected with dl309/dl200+230 and protein was harvested at the indicated post hour infection and analyzed by western blot for E1a expression.
Figure 13:
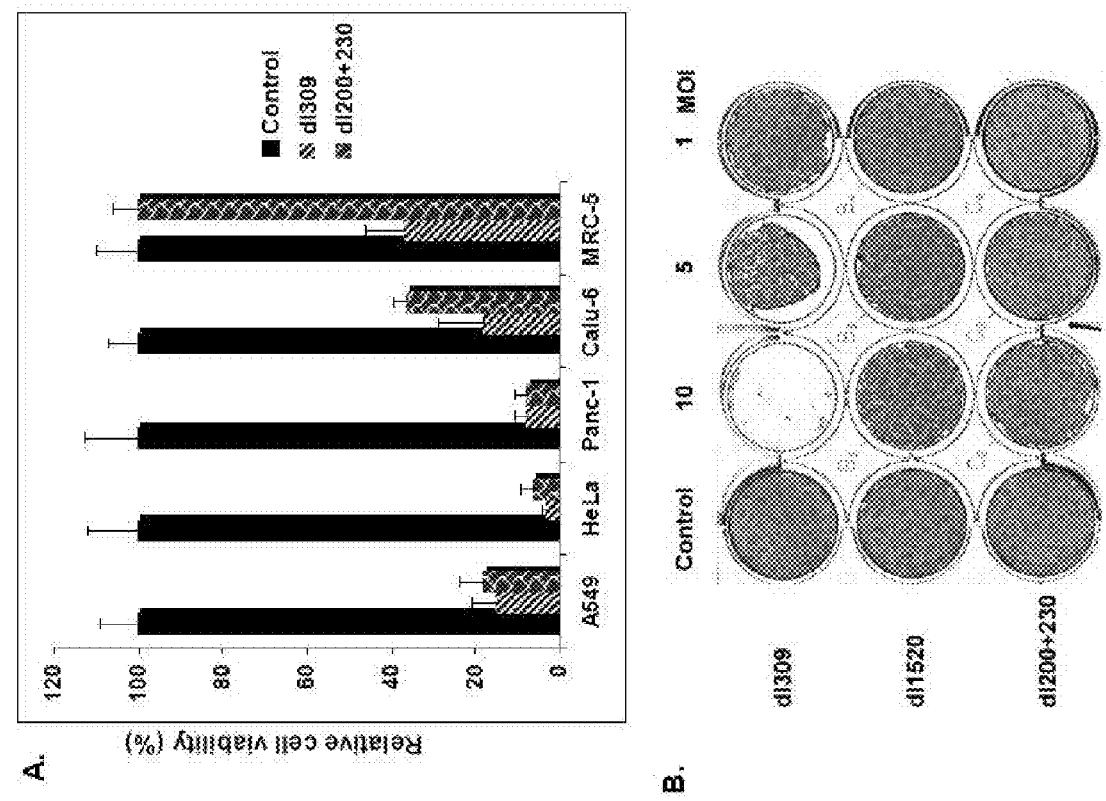
FIG. 13. Oncolytic activity in vitro. (a) Transformed cell lines (A549, HeLa, Panc-1 and Calu-6) and Non-transformed cell line (MRC-5) were infected with viruses; Wt HAd-5, and dl200+230 adenoviruses and assayed for their viability using CCK-8 kit after 4 days and 5 days post infection, respectively. (b) Cytopathic effect of various adenoviruses were analyzed by crystal violet assay in MRC-5 cells infected at indicated MOI and stained after 5 days post infection.

We analyzed E1a expression and cytotoxicity exhibited by mutant virus dl200+230 in various transformed and non-transformed cells. Mutant virus dl200+230, which showed the highest reduction in E1a expression in MRC-5 cell line without any significant reduction in A549 cell lines 24 h.p.i. were tested in various non-transformed cell lines to evaluate the impact of Pea3 binding sites II & III deletion. Studies performed in IMR-90 and WI-38 cell lines showed similar result as obtained from MRC-5 cells suggesting that the reduction of E1a expression was not limited to MRC-5 cells but was similar in other non-transformed pulmonary cell lines. In non-transformed cell line, dl200+230 virus did not show detectable level of E1A protein expression by 24 h.p.i. After 48 h.p.i., mutant virus did show low levels of E1a gene expression in MRC-5 and IMR-90 cells but not in WI-38 cells. In contrast to mutant virus, Wt HAd-5 E1a expression could be detected at 24 h.p.i. and significantly exceeded the expression of E1a from the mutant viruses at 48 h.p.i. (FIG. 12a). We also tested the expression of mutant virus in various transformed cell lines (HeLa, Panc-1 and Calu-6) and found no significant difference in E1a protein expression between dl200+230 and Wt HAd-5 at 24 h.p.i. (FIG. 12b). We compared the cytotoxicity impact of Wt HAd-5, ONYX-015 and dl200+230 viruses in various transformed cell lines (HeLa, Panc-1, Calu-6, and A549) 4 days post infection and in non-transformed cell lines (MRC-5) after 5 days post infection. Mutant virus, dl200+230, showed similar level of cytotoxicity compared to Wt HAd-5 and showed higher efficacy compared to ONYX-015 in A549 and Calu-6 cell lines. In non-transformed cell lines, dl200+230 showed very low cytotoxicity compared to HAd-5 and exhibited very similar level of safety in compared to ONYX-015 (FIGS. 13 A&B).

HAd-5 E1a transcription control region contains binding sites for several transcription factors that are aberrantly expressed in tumor cells including two binding sites for E2F and five binding sites for Pea3 [19, 20]. Previous studies have sought to define the enhancer domain for E1a; however, these studies were performed in malignant cells rather than in non-transformed cells, the natural host for adenoviral infections. To more precisely define the E1a enhancer, deletion mutants of E2F and Pea3 were generated and their impact on E1a expression was evaluated in non-transformed cells.

Pea3 is a transcription factor commonly over-expressed in many tumor cell lines and is associated with an invasive, metastatic phenotype (de Launoit, Y., et al. (2000). The PEA3 group of ETS-related transcription factors. Role in breast cancer metastasis. Adv Exp Med Biol 480: 107-116). Deletion mutants, TAV-255, which removes Pea3 binding sites II & III as well as the distal E2F site demonstrated a 33-fold reduction in E1a mRNA expression at 24 hours post infection. In contrast, deletion mutant, dl200+230, which eliminates Pea3 binding sites II and III but retains the distal E2F site, demonstrated a 50-fold reduction in E1a mRNA expression in non-transformed cells at 24 hours post infection, These findings demonstrate that Pea3 transcription factor binding sites number II and III have a major role in modulating E1a expression in non-transformed cells. E1a protein expression at 24 hours paralleled the findings for E1a mRNA. Interestingly dl200+230, which has deletions of Pea3 binding sites number II and III but retains the E2F site, showed highest reduction in E1a expression. These results suggest that the E2F site has minimal on E1a expression and suggests the possibility that the E2f site may act as a repressor during the early period of E1a expression. Indeed, in transfection assays, we have found that inactivating point mutations of E2F sites resulted in increased E1a expression favoring a repressor function for E2F rather than a transcriptional activation of E1a by E2F (data not shown). The possibility of E2F functioning as a transcriptional repressor under specific conditions has been suggested previously (Weintraub, S. J., Prater, C. A., and Dean, D. C. (1992). Retinoblastoma protein switches the E2F site from positive to negative element. Nature 358: 259-261).

We evaluated the relative importance of each of the Pea3 sites on the transcription of E1a in non-transformed and transformed cells. Deletion of Pea3 site I (dl87) has minimal impact on E1a expression in non-transformed cells. In contrast, deletion of Pea3 sites II and III resulted in approximately a 10 and 20-fold decrease in E1a mRNA expression in non-transformed cells respectively. Deletion of both Pea3 sites II and III resulted in a 50-fold reduction in E1a mRNA expression in non-transformed cells. In addition to diminished E1a mRNA expression, the expression of E1a protein is also significantly decreased due to deletion of these Pea3 binding sites. E1a protein is below the level of detection in a panel of 3 non-transformed cell lines at 24 hours post-infection and is detectable but severely diminished at 48 hours post infection. These results suggest that these Pea3 sites are of critical importance to efficient expression of E1a in non-transformed cells. However, these Pea3 sites are not the exclusive determinants of E1a expression since late expression of low levels of E1a can occur in non-transformed cells. Our findings further indicate that deletion of both Pea3 sites II and III have minimal impact on E1a expression in a panel of tumor cell lines at 24 hours post infection. Our results in the tumor cell lines are consistent with previous studies demonstrating that deletion of Pea3 site number I or III alone reduces the E1a gene transcription by only 2-3 fold at 5 h post-infection (Hearing, P., and Shenk, T. (1983). The adenovirus type 5 E1A transcriptional control region contains a duplicated enhancer element. *Cell* 33: 695-703). In these previous studies, the E1a protein expression at later time points was not determined.

E2F is a transcription factor that is commonly over-expressed in tumor cells due to deregulation of the Rb pathway. Phosphorylation of Rb by cyclin-dependent kinases results in the release of E2F, which then binds to transcriptional regulatory units and induces genes that mediate entry into S-phase. Our results demonstrate that deletion of either or both E2F binding sites located upstream of the E1a cap site had minimal impact on E1a expression in non-transformed cell lines. Specifically, deletion of the E2F site most proximal to the cap site, −218 to −225, had no impact on E1a mRNA or protein expression. Deletion of the E2F site most distal to the cap site, −281 to −287 resulted in a 30% reduction in mRNA expression but no significant impact on E1a protein expression as determined by western blot analysis. Deletion of both sites resulted in a 20% reduction in E1a mRNA expression but no detectable difference in E1a protein levels compared to control. These results demonstrate that deletion of the two E2F transcription factor binding sites located upstream of the E1a cap site have only a minor role in E1a expression in non-transformed cells. Consistent with previous studies, we find that deletion of both E2F sites demonstrated minimal impact on E1a expression in a panel of tumor cell lines (data not shown) (Bruder, J. T., and Hearing, P. (1989). Nuclear factor EF-1A binds to the adenovirus E1A core enhancer element and to other transcriptional control regions. Mol Cell Biol 9: 5143-5153).

E1a regulates early adenoviral gene expression and is essential for efficient viral multiplication (Hearing, P., and Shenk, T. (1983). The adenovirus type 5 E1A transcriptional control region contains a duplicated enhancer element. *Cell* 33: 695-703). Since deletion of Pea3 sites II and III results in severely attenuated expression of E1a in a panel of non-transformed cells but has little impact on the expression of E1a in a panel of tumor cells, these enhancer deletion mutants may be useful as oncolytic viruses. We evaluated the cytolytic activity of dl200+300 (double deletion of Pea3 sites II and III) in tumor and non-transformed cells. The cytolytic activity of dl200+300 is similar to the control virus in a panel of tumor cell lines while demonstrating minimal cytotoxicity in the non-transformed cells (FIGS. 13a and b). Previous studies have demonstrated that dl1520 (ONYX-015) is significantly attenuated when compared to wild-type virus in a variety of tumor cell lines. The diminished capacity for dl1520 to replicate in tumor cells has been linked to the fact that E1b-55k is a multifunctional protein. In addition to binding and inactivating p53, E1b-55k is involved in mRNA transport across the nuclear membrane. In the absence of efficient mRNA transport, dl150 replicates inefficiently in a variety of tumor cell lines. Clinical studies among patients with a variety of cancer, primarily head and neck and colorectal cancer, have demonstrated significant clinical responses in a minority of patients and the clinical development of ONYX-015 was halted. The lack of potency of the virus due to deletion of a critical multifunctional protein may have limited the clinical effectiveness of that oncolytic virus. We have approached the development of an oncolytic virus by determining the specific transcription factor bindings sites that are critical for efficient expression of E1a and replication of HadS in non-transformed respiratory cells. Deletion of the Pea3 sites from the endogenous E1a enhancer has several advantages when developing an oncolytic virus. First, no heterologous DNA sequences have been introduced to achieve tumor-selective expression of E1a. Second, E1a is the first gene expressed following infection of cells with adenovirus and this gene, which regulates subsequent early virus gene expression, is expressed at approximately the levels observed for control adenoviral infections. Third, the multifunctional E1b-55k gene is left intact.

Figure 14:
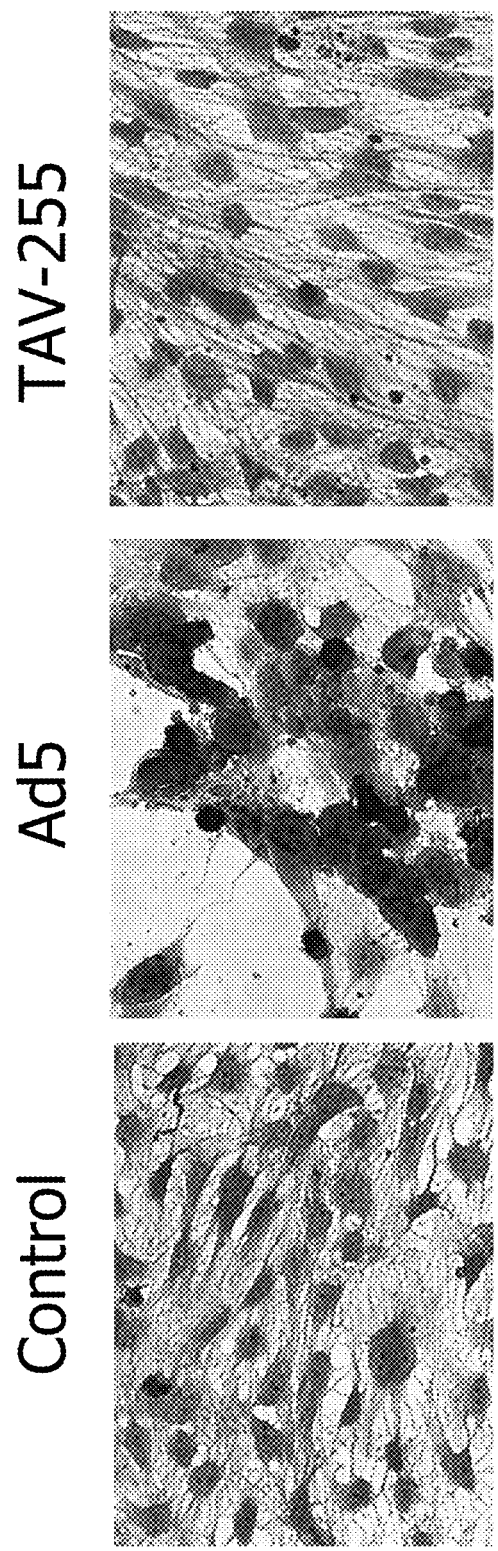
FIG. 14. Non-transformed, WI-38 cells were grown to confluence and then infected with Ad5 or TAV-255 at an MOI of 10. Uninfected control cells and infected cells were fixed at 7 days post-infection, stained with crystal violet and photographed at 40× magnification. The images demonstrate a uniform monolayer of cells without evidence of viral cytolysis in the control cells and cells treated with TAV-255. In contrast, extensive cytolysis is observed for the cells treated with Ad5.
Figure 15:
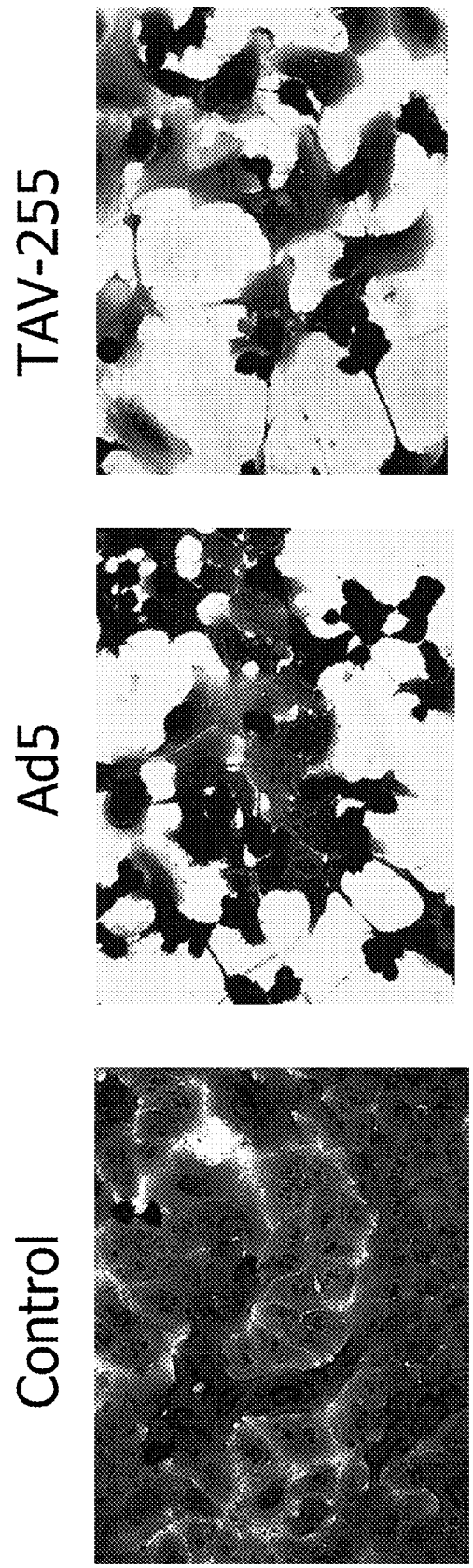
FIG. 15. Transformed A549 cells were grown to confluence and then infected with Ad5 or TAV-255 at an MOI of 10. Uninfected control cells and infected cells were fixed at 3 days post-infection, stained with crystal violet and photographed at 40× magnification. The images demonstrate a uniform monolayer of cells without evidence of viral cytolysis in the control cells. In contrast, extensive cytolysis is observed for the cells treated with Ad5 and with TAV-255.
Selective Expression of E1a Isoforms 12S and 13S FIG. 16. Time course of E1a expression following infection with wild-type Ad5 (WT) and PM975 adenoviruses in (a) WI-38 and (b) MRC-5 cells (M0I=5).

FIGS. 14 and 15 show photomicrographs of normal cells (WI-38) and tumor cells (A549) cells infected with Ad5 or with the promoter deletion virus (TAV-255). In normal cells, there is no evidence of viral mediated cytolytic effects for up to 7 days following infection with TAV-255. In contrast, extensive cell death is observed for normal cells infected with Ad5. In the tumor cells (A549), extensive tumor cell death is seen with both Ad5 and TAV-255 at 3 days post infection. Thus, TAV-255 is selective for lysis of tumor cells, sparing normal cells.

In summary, we have determined that the mechanism of E1a transcription is distinctly different between non-transformed and transformed cells. In addition, we demonstrate that, when studies in non-transformed cells, the E1a enhancer spans a larger region and is more complex than previously recognized. These results demonstrate that Pea3 transcription factor binding sites II and III, but not the E2f binding sites, are critical for efficient expression of E1a in a panel of non-transformed cells but not transformed cells. These results suggest that viruses with selective deletions of the Pea3 transcription factor binding domains II and III may have potent oncolytic activity.

IV. Modified Regulatory Sequence

In one embodiment, the E1a regulatory sequence is modified. The "modified regulatory sequence" has a deletion, substitution, or addition of one or more nucleotides compared to the wild-type sequence. In one embodiment, the sequence of a transcription factor binding site may be modified to reduce affinity for the transcription factor, for example, by deleting a portion thereof, or by inserting a single point mutation into the binding site. Deletion mutants may exhibit enhanced stability over other mutant forms. Preferably, the modified regulatory sequence permits expression in neoplastic cells, but attenuates expression in normal cells. Such modified regulatory sequences may be employed within a viral vector or transformed cell as described further below.

A. Deletion Mutants

In one embodiment, the modified E1a regulatory sequence (E1a Transcriptional Control Region) is a deletion mutant. That is, one or more nucleotides have been deleted compared to the wild type regulatory sequence.

Deleted nucleotides can be contiguous, thereby forming a single deleted region. In this case, the total deletion is the same as the deleted region. In another embodiment, the deletion is non-contiguous. In one embodiment, the total deletion comprises one, two, three, four, or more deleted regions. In one embodiment, the total deletion comprises three deleted regions. In another embodiment, the total deletion comprises two deleted regions. Unless otherwise noted, the generic term "deletion" is used to describe characteristics of the "total deletion" and/or any one or more "deleted regions."

In one embodiment, the deletion (the total deletion and/or any deleted region) is about 1 to about 400, about 1 to about 300, about 1 to about 200, about 1 to about 100, about 50 to about 100, about 25 to about 75, about 5 to about 50, about 5 to about 25, or about 5 to about 10 nucleotides. In another embodiment, the deletion is about 100, about 90, about 50, about 30, about 10, or about 5 nucleotides. In another embodiment, the deletion is 250 or fewer, 150 or fewer, 100 or fewer, 90 or fewer, 50 or fewer, 30 or fewer, 20 or fewer, 15 or fewer, 12 or fewer, 11 or fewer, 10 or fewer, 9 or fewer, 8 or fewer, 7 or fewer, 6 or fewer, or 5 or fewer nucleotides.

In one embodiment, at least one nucleotide is deleted in the region of −255 to −393, −304 to −393, −255 to −305, −265 to −270, or −293 to −299 of the E1a regulatory sequence.

In one embodiment, at least one nucleotide in the enhancer region (−141 to −305) is retained (i.e., not deleted). In another embodiment, at least one nucleotide proximal to the Pea3 II site (−1 to −255) is retained. In yet another embodiment, at least one nucleotide distal to the Pea3 V site (−395 to −498) is retained. In another embodiment, at least one nucleotide is retained in one of the following ranges: −1 to −255, −141 to −305, and −395 to −498.

As described above, Pea3 and E2F are transcription factors that bind the promoter sequence. The E1a regulatory sequence contains five Pea3 binding sites, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains two E2F binding sites, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In one embodiment, at least one of these seven binding sites, or a functional portion thereof, is deleted. A "functional portion" is a portion of the binding site that, when deleted, decreases the functionality, e.g. binding affinity, of the binding site to its respective transcription factor (Pea3 or E2F). In one embodiment, one or more entire binding sites are deleted. In another embodiment, a functional portion of one or more binding sites is deleted. A "deleted binding site" encompasses both the deletion of an entire binding site and the deletion of a functional portion. When two or more binding site are deleted, any combination of entire binding site deletion and functional portion deletion may be used.

On the other hand, in some embodiments, at least one of the binding sites, or a functional portion thereof, is retained in (e.g., not deleted from) the E1a regulatory sequence. By retaining at least a functional portion of the binding site, binding affinity to the respective transcription factor is substantially maintained. A "retained binding site" encompasses retaining an entire binding site and retaining a functional portion thereof. When two or more binding site are retained, any combination of retaining entire binding sites and retaining functional portions may be used.

In one embodiment, at least one Pea3 binding site, or a functional portion thereof, is deleted. The deleted Pea3 binding site can be Pea3 I, Pea3 II, Pea3 III, Pea3 IV, and/or Pea3 V. In one embodiment, the deleted Pea3 binding site is Pea3 II, Pea3 III, Pea3 IV, and/or Pea3 V. In another embodiment, the deleted Pea3 binding site is Pea3 IV and/or Pea3 V. In another embodiment, the deleted Pea3 binding site is Pea3 II and/or Pea3 III. In another embodiment, the deleted Pea3 binding site is both Pea3 II and Pea3 III.

In another embodiment, the Pea3 I binding site, or a functional portion thereof, is retained.

In one embodiment, at least one E2F binding site, or a functional portion thereof, is deleted.

In another embodiment, at least one E2F binding site, or a functional portion thereof, is retained. In one embodiment, the retained E2F binding site is E2F I and/or E2F II. In another embodiment, the retained E2F binding site is E2F II.

In another embodiment, the total deletion consists essentially of one or more of Pea3 II, Pea3 III, Pea3 IV, and/or Pea3 V, or functional portions thereof. In other words, other binding sites—the remaining Pea3 sites and both E2F binding sites—are retained.

In one embodiment, the deletion mutant is dl309-6, dl340-12, TAV-255, dl87, dl55, dl275, dl200, dl212, dl220, dl230, dl200+230, or dl212+275. In one embodiment, the deletion mutant is dl309-6, TAV-255, dl55, dl200, dl230, or dl200+230. In another embodiment, the deletion mutant is TAV-255, dl55, dl200, dl230, or dl200+230. In one embodiment, the deletion mutant is TAV-255.

V. Selective Expression of E1a Isoforms 12S and 13S

As described above, deletions of the adenovirus enhancer that remove the region from −305 to −255 (TAV-255) result in tumor selective expression of E1a and preferential replication of this virus in tumor cells. Previous studies have demonstrated that E1a has pro-apoptotic activity (Flinterman, Gaken et al. 2003) raising the possibility that tumor-selective expression of E1a could enhance tumor cell killing. The adenoviral E1a protein is a complex of proteins modified by RNA splicing resulting in primarily 13s, 12s, and 9s mRNA.

We evaluated the expression, viral replication, and lytic activity of adenovirus modified to selectively express the E1a-13s gene product in non-transformed and transformed cells when expressed from the native E1a promoter and from vectors harboring the enhancer deletion (TAV-255), which facilitates preferential expression of E1a in tumor cells. We demonstrate that viruses selectively expressing the 13s gene product efficiently express the 289R protein in a panel of tumor cells and that viral replication and lytic activity of this virus is similar to wild-type Ad5. In contrast, we find that E1a 13s expression is markedly delayed and diminished in growth arrested non-transformed cells compared to tumor cells. The oncolytic activity of the 13s restricted virus was compared to dl1520 (Onyx-015). The 13s restricted virus was as attenuated as dl1520 in the non-transformed cells and was markedly more potent than dl1520 in some tumor cell lines tested. These results demonstrate that oncolytic viral vectors based on tumor-selective expression of 13s restricted viruses are feasible and can provide efficient viral replication in tumor cells while severely restricting viral replication in non-transformed cells.

Figure 16:
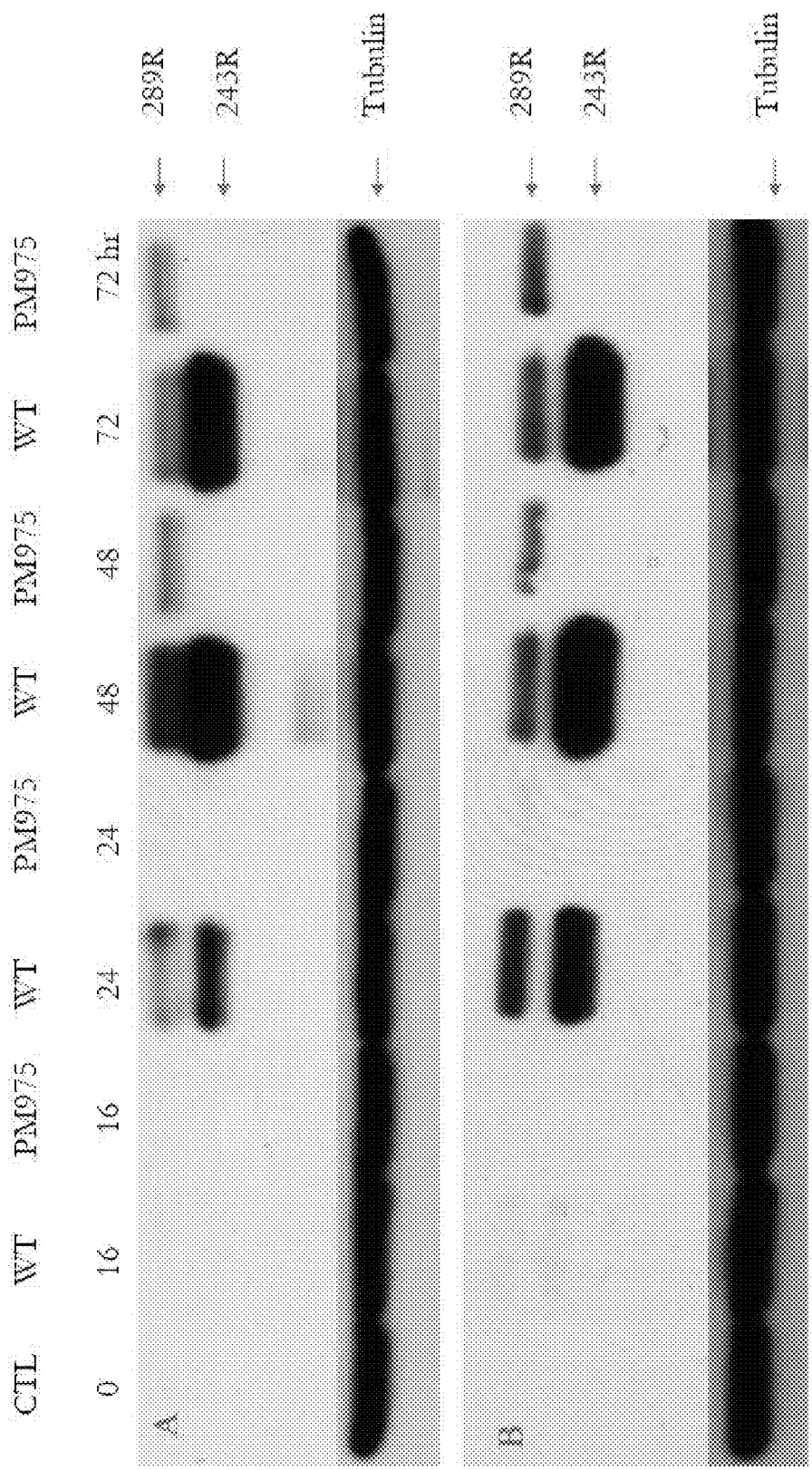

The expression of the E1a proteins was evaluated in growth arrested WI-38 cells which are non-transformed, diploid lung fibroblasts (Hayflick and Moorhead 1961). The results, shown in FIG. 16a-b, demonstrate that infection with wild-type adenovirus results in expression of two proteins. The 289 amino acid protein is derived from the 13s mRNA while the 243 amino acid protein is derived from the 12s mRNA. The 12s mRNA is an mRNA splicing product that differs from the 13s mRNA due to removal of an internal domain that functions to transactivate other early viral genes. In WI-38 cells, the 243 amino acid protein is the dominant species. The abundance of both species increases between 24 and 48 hours, followed by a significant decrease in the relative abundance of the 289 amino acid product by 72 hours post infection. In contrast to the wild-type virus, the PM975 virus, which is restricted to expression of the 289 amino acid form of E1a, demonstrates a marked delay in the onset of E1a expression and is not observed until 48 hours post infection. In addition, the abundance of the 289R isoform of E1a, is substantially decreased compared to the wild-type virus at 24 and 28 hours post infection. By 72 hours post infection, the abundance of the 289R isoform is similar between wild-type virus and PM975; however, total expression of E1a protein is significantly reduced in PM975 since no 243R, which is the dominant species, is produced. Similar results are observed for another non-transformed cell line, MRC-5, FIG. 16b.

Figure 17:
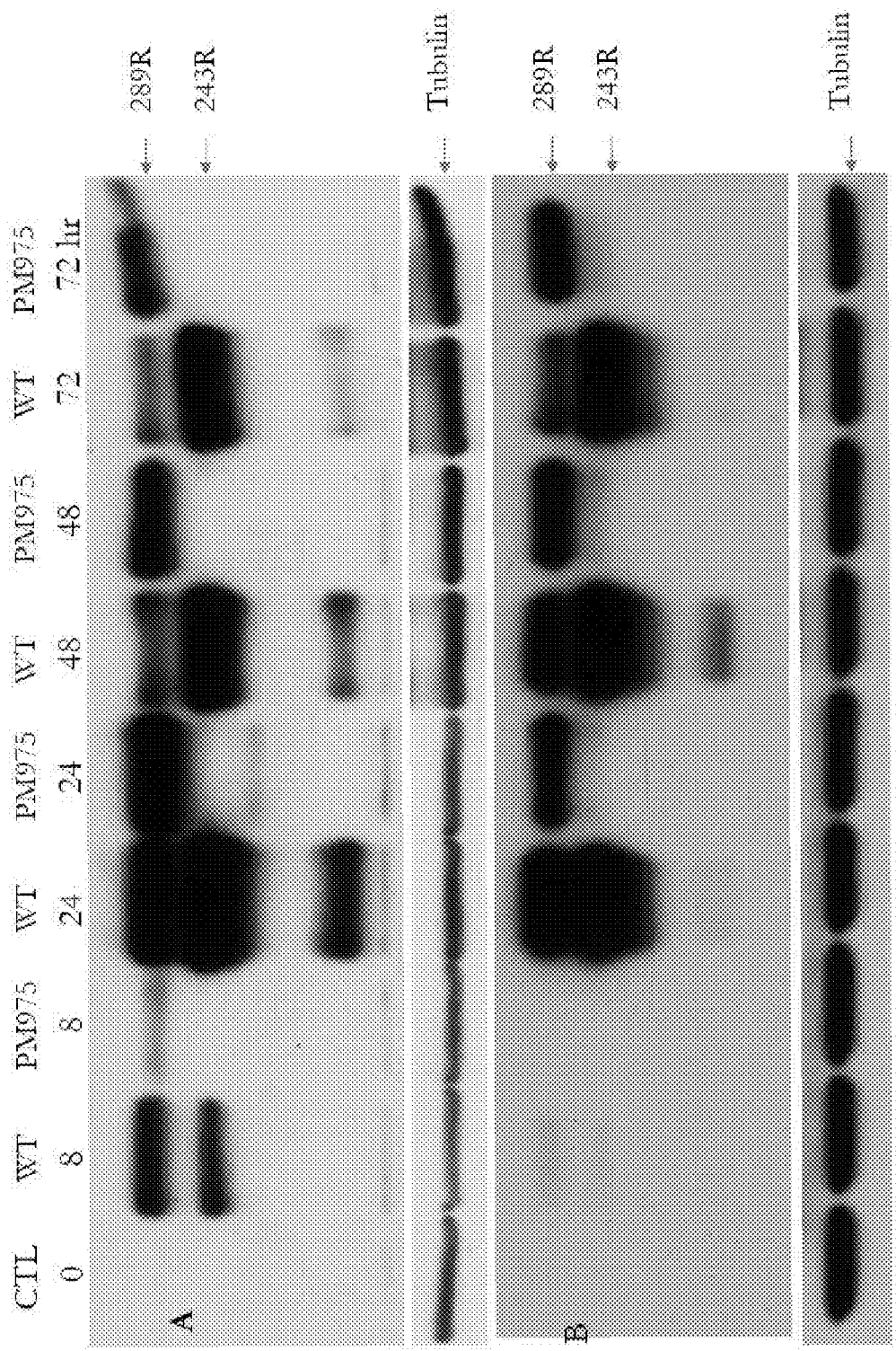
FIG. 17. E1a expression in (a) A549 and (b) Panc 1.

The onset of expression of E1a from wild-type adenovirus and PM975 was evaluated in two tumor cell lines A549 (lung) and Panc-1 (pancreas), and the results are shown in FIG. 17a-b. In contrast to the non-transformed cells where detectable expression of the large form of E1a was not observed until 48 hours post infection, expression of 289R was detectable in the tumor cell lines by 8 to 24 hours post infection in the tumor cell lines. While the 243R species of E1a was the most abundant form in WI-38 cells, even at the earliest time points, the abundance of the 289R and the 243R species was similar at the early time points in the tumor cells, with expression of primarily the 289R isoform exceeding the 243R isoform at the earliest times post-infection. Over the course of the infection, preferential accumulation of the 243R species was observed by 48 to 72 hours post-infection in the tumor cells lines. The expression of the 289R form of E1a from PM975 paralleled the expression observed for the wild-type virus in each cell line, with peak expression occurring at approximately 24 hours post infection, but with continued abundant expression at 48 and 72 hours post infection. The abundance of the 289R species from PM975 at 72 hours post-infection and equaled or exceeded the abundance of 289R expressed in cells infected with wild-type virus.

Figure 18A:
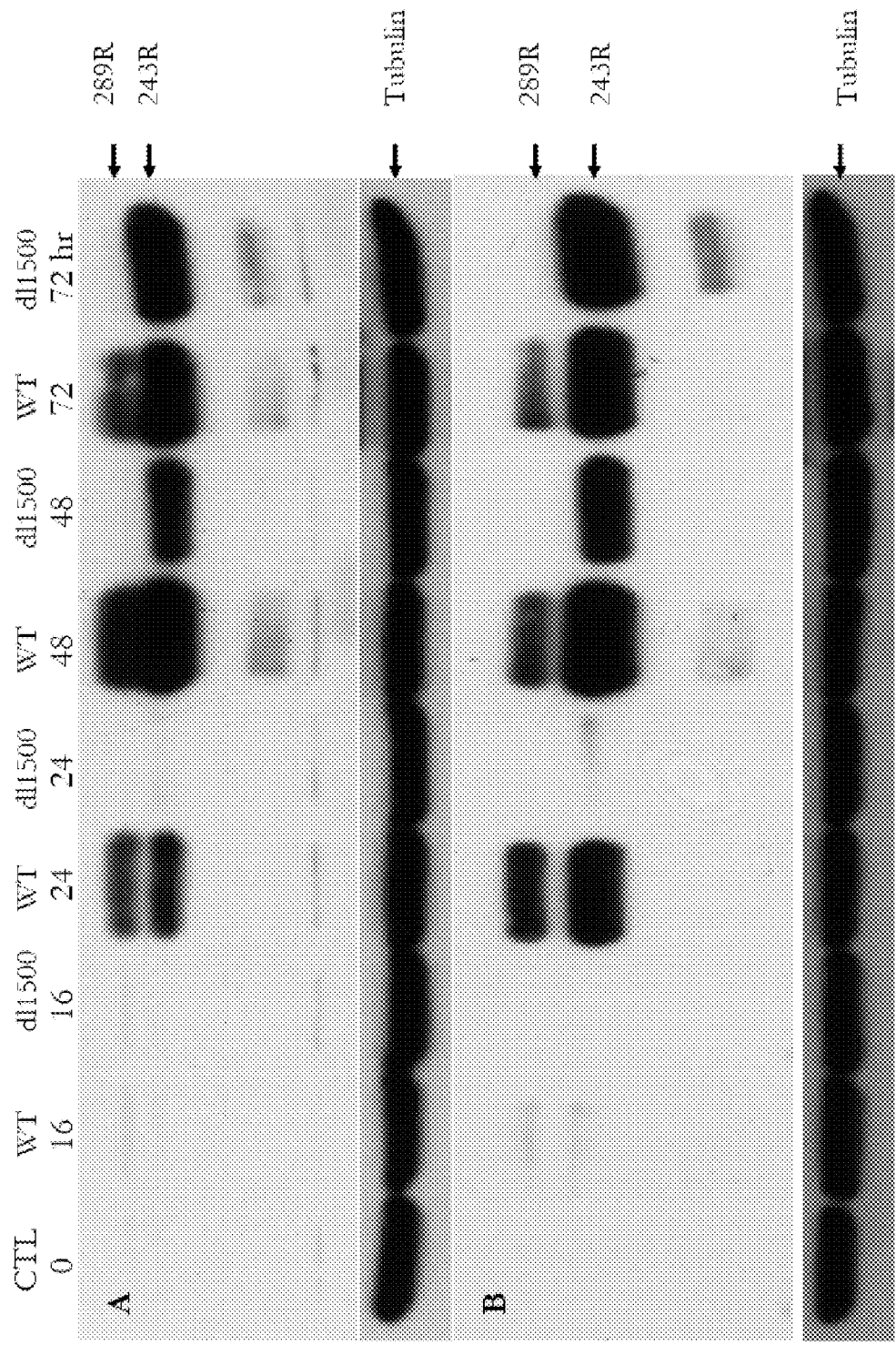
FIG. 18. a) Time course of E1A expression in a) WI-38 cells and b) MRC-5 cells (MOI=5). b) Time course of E1A expression in c) A549 cells and d) Panc-1 cells (MOI=5).
Figure 18B:
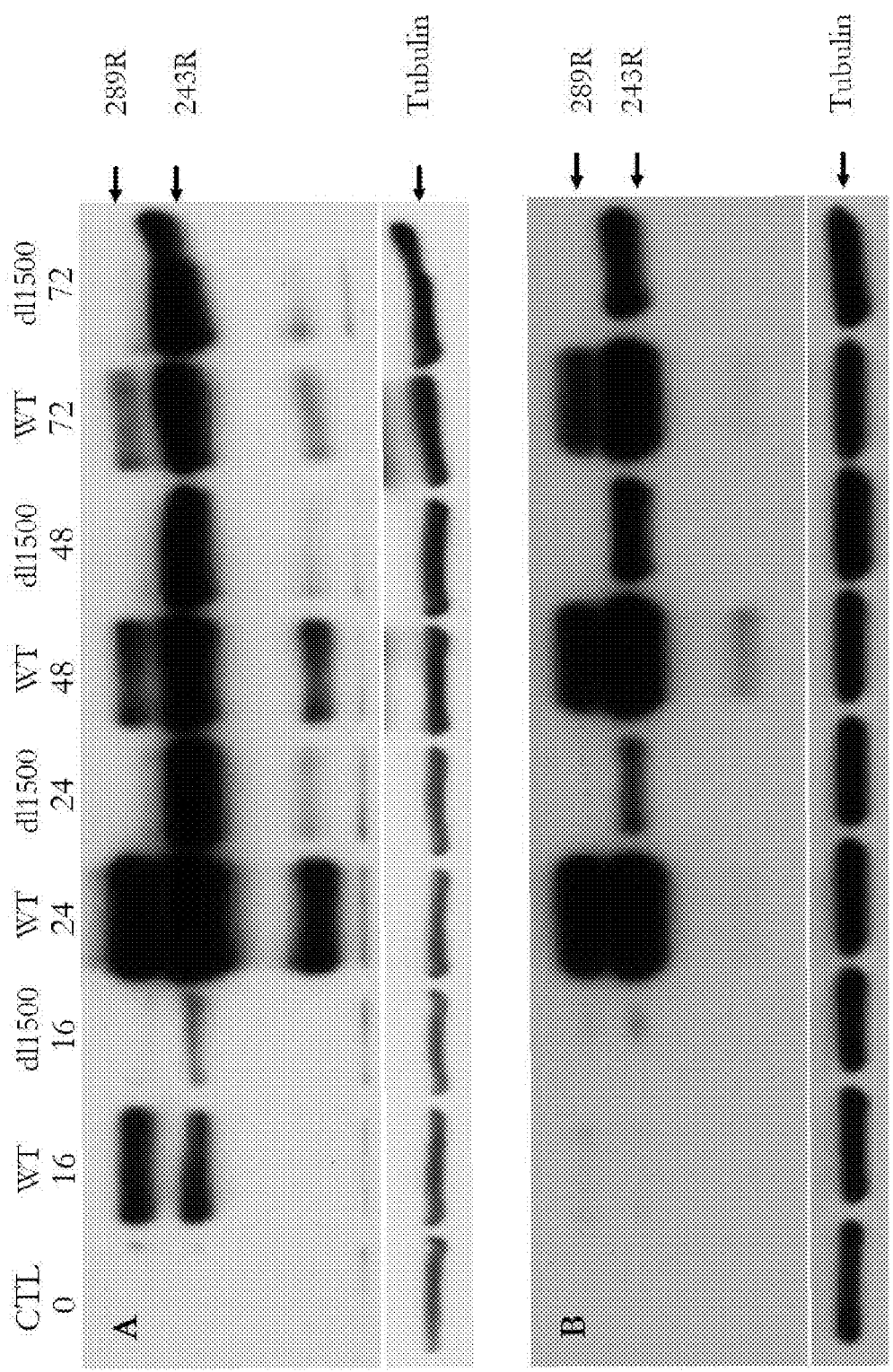
Figure 19:
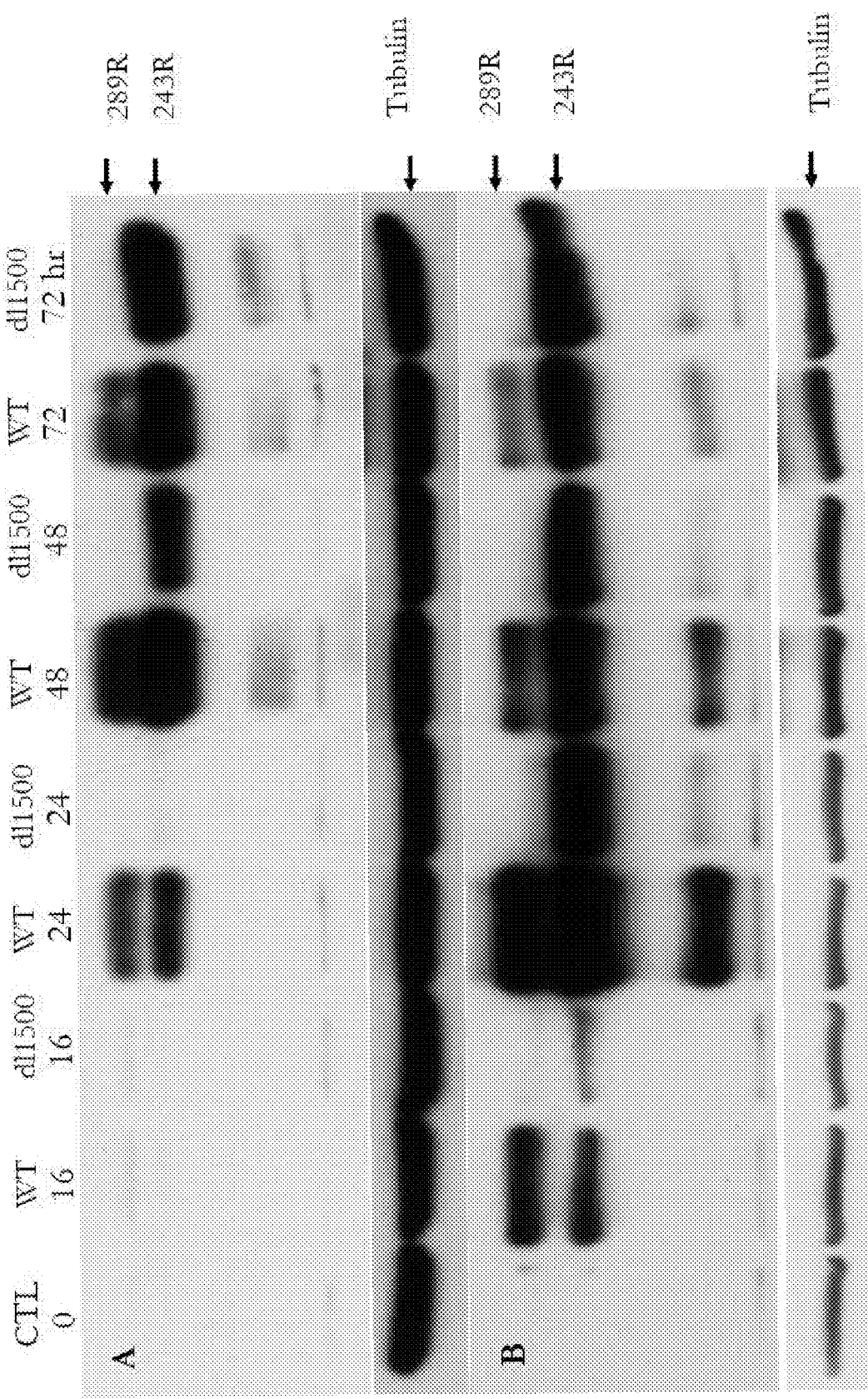
FIG. 19. Time course of E1A expression in a) WI-38 cells and b) A549 cells (MOI=5).

We evaluated the onset of expression of the 243R isoform of E1a from dl1500, a virus that expresses exclusively the 243R isoform of E1a in growth-arrested non-transformed (WI-38 and MRC-5) cells and in tumor (A549 and Panc1) cells. Expression of the 243R isoform is delayed in cells infected with dl1500 when compared to cells infected with the wild-type virus. The delay in expression of the 243R isoform was observed for both non-transformed cell lines (WI-38 and MRC-5) FIG. 18a (panels a and b). Expression of the 243R isoform is clearly evident by 24 hours post infection with wild-type virus; however, 243R is at or below the level of detection at 24 hours post-infection with dl1500. Expression of the 243R isoform is evident by 48 hours following infection with dl1500 in both cell lines and by 72 hours post-infection is approximately equal to the abundance observed following infection with wild-type virus. In contrast to the non-transformed cell lines, expression of the 243R isoform is clearly evident by 16 to 24 hours post-infection with dl1500 in the tumor cells lines FIG. 18b (panels a and b). For comparative purposes, the expression of the E1a is shown over time in WI-38 and A549 cells (FIG. 19 panels A and B respectively). The onset of E1a expression from WI-38 infected cells is clearly delayed, particularly in the cells infected with dl1500.

We have previously demonstrated delayed onset of E1a expression from viruses with a deletion of the E1a promoter that removes two Pea3 sites and one E2f site (TAV-255). We have introduced this 50 bp deletion into a vector that selectively expresses the 289R form of E1a and compared the onset of E1a expression in WI-38 and A549 cells.

Figure 20:
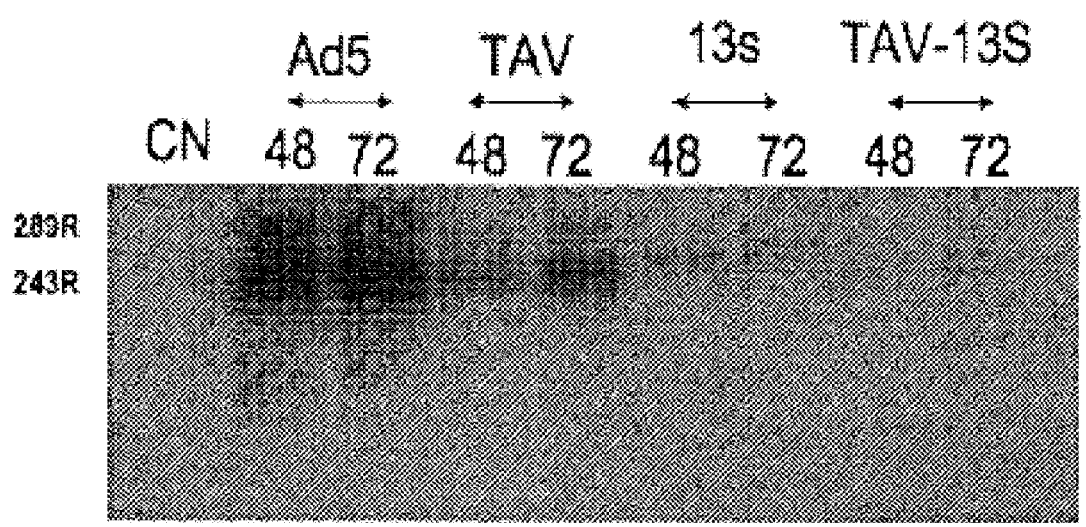
FIG. 20. E1a expression in growth arrested WI-38 cells infected with Ad5, TAV, and TAV-13s for E1a at 48 and 72 hours (MOI=5).

We evaluated the onset of E1a expression in growth arrested WI-38 cells infected with 1) Ad5, PM975 and TAV-13s for E1a at 24, 48 and 72 hours (MOI=5). These results demonstrate that expression of E1a is at or below the level of detection for TAV-13S up to 72 hours post infection. (See FIG. 20.)

A Western blot of A549 cells infected with 1) Ad5, PM975, TAV-13s for E1a at 24, 48 and 72 hours (MOI=5) shows no significant delay in expression of E1a from the TAV-13s compared to wild-type virus or PM975 in A549 cells.

Figure 21:
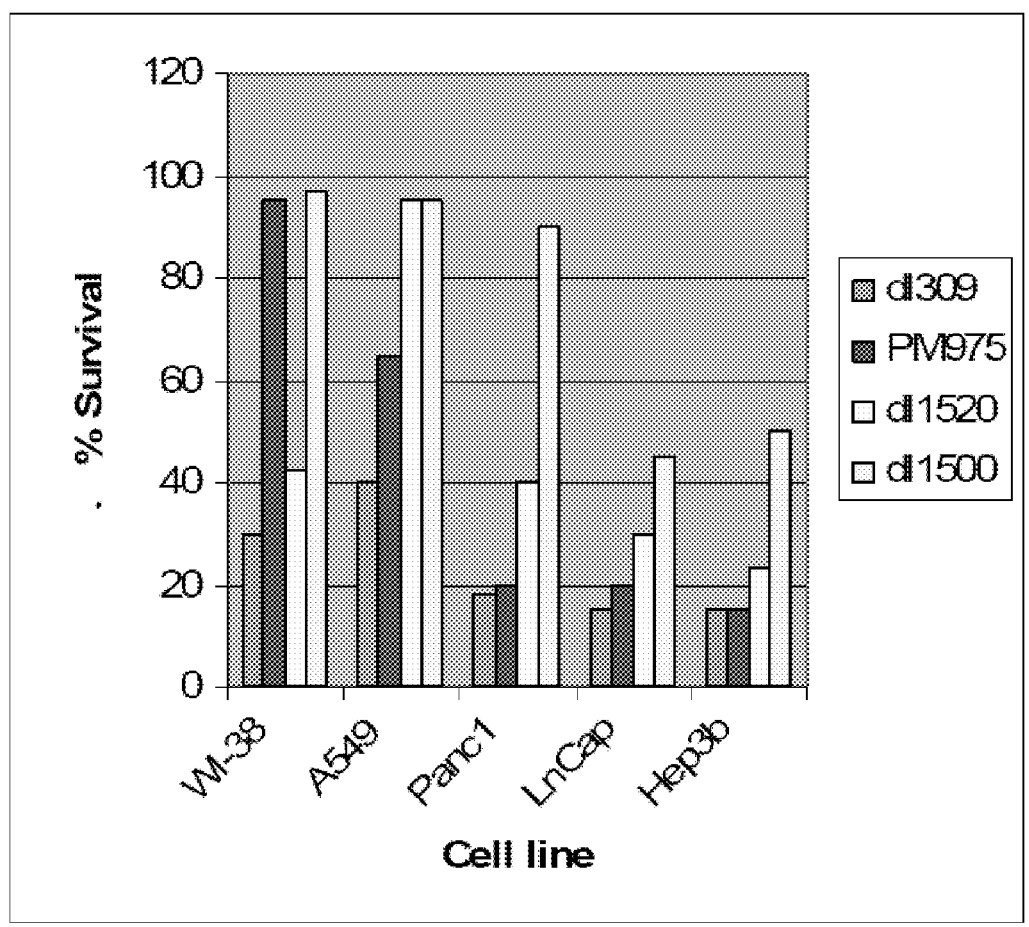
FIG. 21. Viability of cells following infection with dl309, PM975, dl1520 or dl1520 in WI-38 cells at 7 days post-infection at MOI of 30 and A549, Panc-1, LnCap and Hep3b at 5 days post-infection at MOI of 3.
Figure 22:
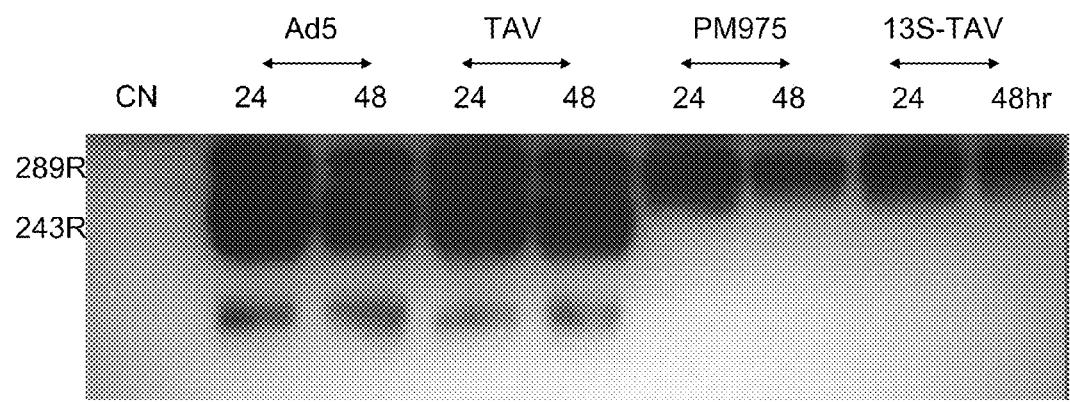
FIG. 22. E1a Expression in A549 at MOI of 2: A549 cells were infected with Ad5, TAV, PM975 (13s) or 13sTAV at an MOI of 2. Protein was isolated from infected cells at 24 and 48 hours post-infection and analyzed for expression of E1a by western blot. The expression of 13S E1a mRNA (289R) is seen in all lanes at approximately equal abundance and is the only form observed in the virus restricted to expression of 13S (PM975) and 13S-TAV. This demonstrates that the introduction of the enhancer deletion as shown (TAV and 13s-TAV) results in no significant decrement in expression of E1a-289R.
Figure 23:
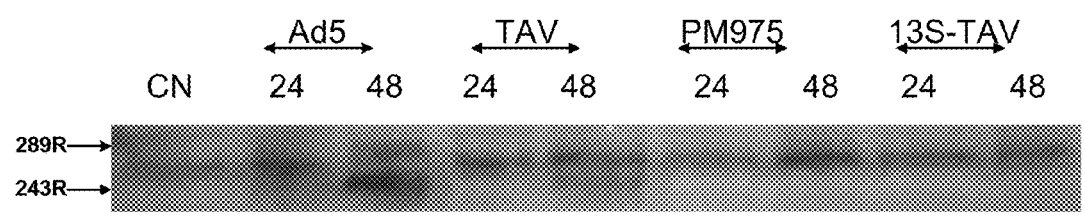
FIG. 23. E1a Expression in WI138 at MOI of 2: Growth arrested WI-38 cells were infected with Ad5, TAV-255 (TAV), PM975 (13S expression only), and 13S-TAV (TAV-255 promoter deletion and restriction of expression to 13S). Protein was extracted from cells at 24 and 48 hours post-infection and analyzed for expression of E1a by western blot. Expression of the 289R and 243R forms of E1a are observed at 48 hours post infection in the cells infected with Ad5 and to a lesser extent (TAV). No detectable expression of E1a is seen cells infected with PM975 or 13S-TAV.
E1b 19K Clone Insert FIG. 24. Organization of the E1 region of adenovirus type 5. E1b-19k and E1b-55k are derived from overlapping sequences by mRNA splicing variants. The first 202 nucleotides from E1b-19k were deleted after the E1b start site and DNA inserts were cloned into this site in frame without disruption of the E1b-55k start site.

FIG. 21 shows the viability of cells following infection with dl309, PM975, dl1520 or dl1520 in WI-38 cells at 7 days post-infection at MOI of 30 and A549, Panc-1, LnCap, and Hep3b at 5 days post-infection at MOI of 3. These results demonstrate that the viruses expressing exclusively the 289R isoform of E1a (PM975) and the 243R isoform of E1a (dl1500) have minimal impact on cell survival out to 7 days post-infection even at very at high MOIs (30). The cell toxicity for these two E1a restricted viruses was significantly less than either wild-type virus (dl309) or the E1b-55k deleted virus (dl1520). The tumor cell lines were evaluated for cell survival 5 days post-infection with and MOI of 3 (1 log lower than the input virus for the experiment with WI-38 cells). These results demonstrate that infection of these tumor cells lines with the virus expressing the 289R form of E1a (PM975) have increased cytolytic activity compared to either dl1520 or dl1500 and that the level of cytolytic activity for PM975 is similar to wild-type virus in these cell lines.

The E1a gene of Ad5 is processed by mRNA splicing to yield five distinct isoforms; 13S, 12S, 11S, 10S and 9S. The major forms 13S and 12S code for two E1a proteins, 289R and 243R respectively, regulate transcription of both viral and cellular genes in adenovirus-infected cells and are essential for adenoviral replication. The 289R form includes a critical transactivation domain that activates transcription of the early adenoviral genes: E2, E3, and E4 (Berk, Lee et al. 1979; Jones and Shenk 1979). This domain is spliced out to generate the 243R isoform of E1a and viruses expressing only the 243R form are unable to transactivate expression from the early viral genes (Montell, Courtois et al. 1984). E1a induces expression of cellular genes including c-Fos, c-Jun, and c-Myc and represses the transcription of c-erbB2 and epidermal growth factor receptor. E1a proteins can drive quiescent cells into cell division by interaction with critical cellular cell cycle proteins including pRB, p27, cyclin A, cyclin E, CtBP, and p300/CBP.

Previous studies have demonstrated that adenovirus engineered to selectively express the 289R form of E1a have approximately normal expression of early and late viral proteins, but have diminished viral DNA synthesis in growth arrested WI-38 cells (Spindler, Eng et al. 1985). Growth arrested WI-38 cells were used as a model of a natural viral infection, and these authors demonstrated that viral DNA synthesis is reduced to 20-30% of control levels at 24 to 36 hours post-infection in growth arrested cells but not in proliferating (subconfluent) WI-38 cells or HeLa cells. While diminished viral DNA synthesis was observed in cells infected with the virus restricted to expression of the 289R form of E1a, they found no significant differences in early viral mRNA expression and no differences in either early or late viral protein synthesis. However, early viral protein expression was determined by analysis of E1b and E2 proteins rather than by analysis of E1a expression. In contrast to the previously published work, we demonstrate that the onset of expression of E1a is significantly delayed, and the abundance is diminished in growth-arrested non-transformed (WI-38 and MRC-5) cells when infected with adenovirus restricted to expression of only the 289R isoform for E1a (PM975) when compared to the same cells infected with wild-type virus (dl309). In the non-transformed cells, expression of 289R was not observed until 48 hours post-infection while expression of E1a from the wild-type Ad5 is observed within 24 hours in the non-transformed cells. Even when observed, the abundance of E1a is considerably lower than control levels. We extend the prior studies and demonstrate that the expression of the 243R form of E1a is delayed in growth arrested WI-38 cells when infected with dl1500 compared to wild-type virus. These results demonstrate that in the absence of normal processing of E1a, the expression of both the 289R and the 243R form of E1a is delayed and reduced in abundance in growth-arrested non-transformed cells.

The requirement for processing of E1a to alternate splicing forms for efficient expression of the 289R form in these non-transformed cells is less stringent in tumor cells. We evaluated the expression of E1a from tumor cells infected with PM975 and dl309. The results of these studies demonstrate that tumor cell lines express the 289R form of E1a as early as 8 hours post-infection and that processing of E1a to alternate splicing forms is not required to achieve efficient expression of the 289R form in tumor cell lines. In contrast to the non-transformed cell lines, the abundance of 289R expressed in tumor cell lines infected with the virus restricted to expression of 289R (PM975) can equal or even exceed the abundance of 289R expressed from cells infected with wild-type virus (dl309).

The viability of cells infected with wild-type virus (dl309), virus with a deletion in the E1b-55k gene (dl1520/Onyx-015), and viruses selectively expressing the 298R (PM975) and the 243R (dl1500) form of E1a was determined. No significant decrement in cell viability was observed in growth-arrested WI-38 cells out to 7 days post-infection with either PM975 or dl1500 up to MOIs as high as 30. These results demonstrate that restriction of E1a splice products to either E1a isoform can severely reduce the lytic activity of these viruses in non-transformed, growth-arrested cells. In contrast, PM975 has potent lytic activity, approximately at the level of wild-type virus, in the tumor cell-lines tested. In addition, this analysis shows that PM975 has lytic activity when compared to dl1520 (Onyx-015) in the cell lines tested. Since E1a is the first protein produced by adenovirus, selective restriction of this protein to the 289R form has significant potential as an oncolytic virus.

To further restrict expression of E1a to tumor cells and limit expression of E1a in non-transformed cells, we introduced the deletion of a short-region of the E1a promoter that encompasses the two Pea3 sites and one E2F site (TAV-255) into a virus selectively expressing the 298R form of E1a. We demonstrate that this virus has markedly diminished expression of E1a in growth-arrested WI-38 cells but that the expression of 289R in A549 cells is similar to wild-type virus in A549 cells. Introduction of this promoter deletion can minimize expression of E1a in non-transformed cells.

Multiple differentially expressed mRNAs from the same coding sequence enable complex adenoviral gene expression from a compact genome and distinct mRNAs accumulate at different points during infection. The E1a pre-mRNA is differentially spliced into 13S, 12S, and 9S mRNAs with 13S mRNA predominating during the early phase of infection and 12S/9S predominating during later points of infection. These mRNAs are generated by using different 5' spice sites linked to a common 3' splice site (Imperiale, Akusjnarvi et al. 1995). The process of viral mRNA splicing is dependent on cellular spicing factors and the switch from 13S to 12S and 9S mRNA expression is thought to be due to a titration of specific splicing factors during the course of viral infection (Gattoni, Chebli et al. 1991; Larsson, Kreivi et al. 1991; Himmelspach, Cavaloc et al. 1995). Disruption of normal E1a splicing by over-expression of splice control factors for E1a 13s can reduce accumulation of late mRNA and lower viral yield (Molin and Akusjarvi 2000). We demonstrate that restricted splicing of E1a to the 289R form diminished and expression of 289R in non-transformed cells but has only modest impact on the onset of 289R expression in tumor cells and can results in accumulation of 289R to levels that are higher than achieved during infection with wild-type virus. On potential explanation for this effect is that the onset of viral DNA synthesis is delayed in WI-38 cells infected with PM975 (Spindler, Eng et al. 1985). Since new viral DNA synthesis can impact mRNA processing (Larsson, Kreivi et al. 1991), the delay in synthesis of new viral DNA may impact E1a processing in growth arrested WI-38 cells. In contrast, since tumor cells have dysregulated proliferation, the onset of viral DNA synthesis may not be delayed and may facilitate expression of 289R even in the absence of expression of 243R.

In summary, tumor-selective replication of viruses and preferential viral mediated lysis of tumor cells is the basis for the concept of oncolytic viruses. The prototype of an oncolytic virus is Onyx-015 (dl1520). This virus has a deletion of the E1b-55k gene that was postulated to confer tumor-selective replication of the virus and consequently selective lysis of the tumor while sparing normal cells. We compared oncolytic activity of the virus restricted to expression of E1a-289R to dl1520 in a panel of non-transformed and transformed cells. We demonstrate that restriction of E1a expression to the 289R form of E1a results in a virus that his more attenuated than dl1520 in both non-transformed cell lines tested. Furthermore, we demonstrate that restriction of E1a expression to the 289R form results in a highly potent oncolytic virus in the tumor cell lines tested. The 289R restricted virus was more potent than dl1520 in the cell lines tested and approached the level of cytolytic activity observed for wild-type Ad5 in these tumor cell lines. Restricted E1a expression, possibly coupled with the E1a promoter deletion described, may yield an oncolytic viral vector with near wild-type lytic activity in tumor cells while having very limited lytic activity in non-transformed cells.

Accordingly, in one embodiment, a recombinant virus is provided that selectively expresses at least one E1a isoform. The "selective expression" of an isoform means that the selected isoform is expressed more than one or more of the other isoforms (as measured by mRNA expression). In one embodiment, one isoform is expressed at levels that approximate wild-type expression, while the expression of one or more other isoforms is attenuated. In one embodiment, expression of the selected isoform is at least 75%, at least 80%, at least 90%, at least 95%, or at least 99% of wild-type expression. In another embodiment, expression of the one or more other isoforms is attenuated to no more than 25%, no more than 15%, no more than 10%, no more than 5%, no more than 3%, or no more than 1% of wild-type expression.

In some embodiments, the recombinant virus substantially excludes expression of at least one isoform. In this case, expression an isoform is attenuated to no more than 25%, no more than 15%, no more than 10%, no more than 5%, no more than 3%, or no more than 1% of wild-type expression.

In one embodiment, the recombinant virus selectively expresses E1a-12S. In one embodiment, the recombinant virus selectively expresses E1a-12S compared to E1a-13S. In yet another embodiment, the recombinant virus selectively expresses E1a-12S and substantially excludes expression E1a-13S.

In one embodiment, the recombinant virus selectively expresses E1a-13S. In one embodiment, the recombinant virus selectively expresses E1a-13S compared to E1a-12S. In yet another embodiment, the recombinant virus selectively expresses E1a-13S and substantially excludes expression of E1a-12S.

VI. E1b 19K Clone Insert

Modification of the E1 promoter results in preferential expression of E1a and E1b proteins in a panel of tumor cell lines. While early and abundant expression of E1 proteins occurs in tumors cells infected with the E1 promoter modification, low levels of protein expression occur at later time points in non-transformed cells. However, this low level of protein expression was not sufficient to result in significant cell lysis for up to seven days post infection in the non-transformed cells tested. In contrast, abundant E1a and E1b expression is observed in tumor cells as early as 8 to 12 hours post-infection in tumor cells and extensive cell death is observed among a panel of tumor cell lines at 3 days post infection. These finding indicate that the E1a promoter deletion vector could be used as an effective platform for the expression of proteins preferentially in tumor cells. In addition, this vector could be used to deliver low-levels of proteins to normal cells as well. Consequently, the E1a promoter deletion vector could be an effective dual-function expression vector with 1) potent oncolytic activity when infecting tumor cells and 2) potent immune activation or vaccine properties when infecting non-transformed cells. We describe this vector as an oncolytic vaccine. We further describe the novel use of the E1b-19k region as a site to clone DNA sequence of interest. Using E1b-19k as a cloning site permits the preservation of intact E1a and E1b-55k viral proteins. Preservation of these critical viral proteins permits viral replication approaching wild-type viral levels in a panel of tumor cell lines.

As described above, tumor-selective expression of E1a can be achieved by modifying the endogenous E1 promoter. Consequently, selective expression of transgenes can be achieved using the modified E1a enhancer. Previously, cloning of genes into adenovirus commonly involved genetic deletion of the entire E1a cassette with replacement of the transgene of interest, typically under the control of a strong promoter such as the CMV promoter. However, this approach does not permit tumor-selective expression of these transgenes. We describe the use of E1b-19k as a cloning site in adenovirus. There are no previous publications using this region as a cloning site. The E1 unit is composes of two major genes, E1a and E1b, both with multiple splice products that generate various proteins. The major E1a proteins are designated 289R and 243R, and the major E1b proteins are designated E1b-19k and E1b-55k.

The E1b 19k locus can be used as a cloning site for several reasons. First, E1a is essential for efficient viral replication and disruption of this gene can severely restrict efficient viral replication. Consequently, this was not an ideal site for cloning of transgenes. Second, the E1b-55k gene is a multifunctional protein that is involved in binding and inactivation of p53 as well as the transport of mRNA across the nuclear membrane. Deletion of E1b-55k gene was the basis of the proposed selectivity of Onyx-015 for tumors with mutations in p53. However, deletion of E1b-55k also disrupts the efficient transport of mRNA from the nucleus to the cytoplasm. Consequently, deletion of the viral E1b-55k gene, resulting in a crippled virus that replicates poorly in many cancer cell lines. Consequently, this was not an ideal site for cloning of transgenes. And third, the E1b-19k gene functions primarily as an anti-apoptotic gene and is a homolog of the cellular anti-apoptitic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Since many tumor cells have acquired the capacity to overcome apoptotic signals, for example by over expression of BCL-2, E1b-19k is potentially redundant in tumor and could be disrupted to provide a site to insert genes and DNA sequences. However, since E1b-19k is a splice product of the E1b-55 gene, cloning into the E1b-19k region, without disrupting E1b-55k is technically challenging. There are no publications describing the use of the E1b-19k region for cloning of genes. We demonstrate that selective cloning of genes into the E1b-19k gene can be achieved without disruption of the E1b-55k gene.

We demonstrate that exogenous genes including TNF and mutated kras peptides can be cloned into the E1b-19k region, and that these genes are efficiently expressed. We further demonstrate a potent antitumor effect for viruses with expression of transgenes from E1b-19k and from viruses with the E1a promoter deletion combined with insertion of genes into the E1b-19k region.

Figures 1, 24:
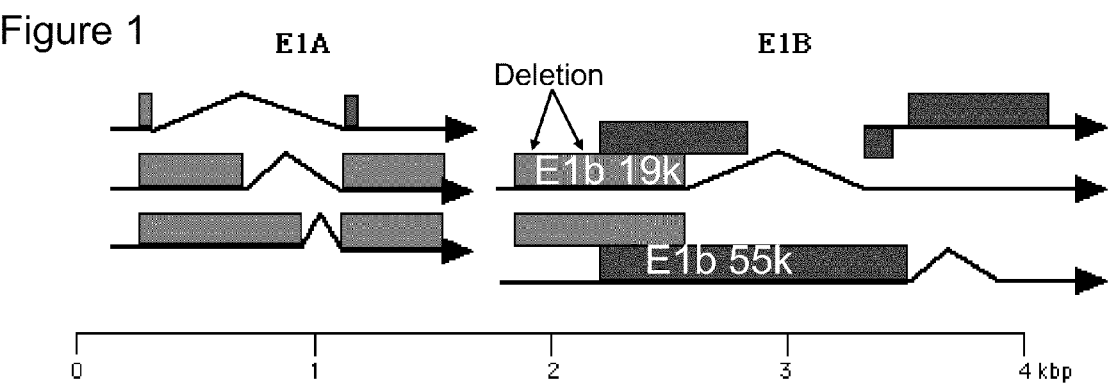
Figure 25:
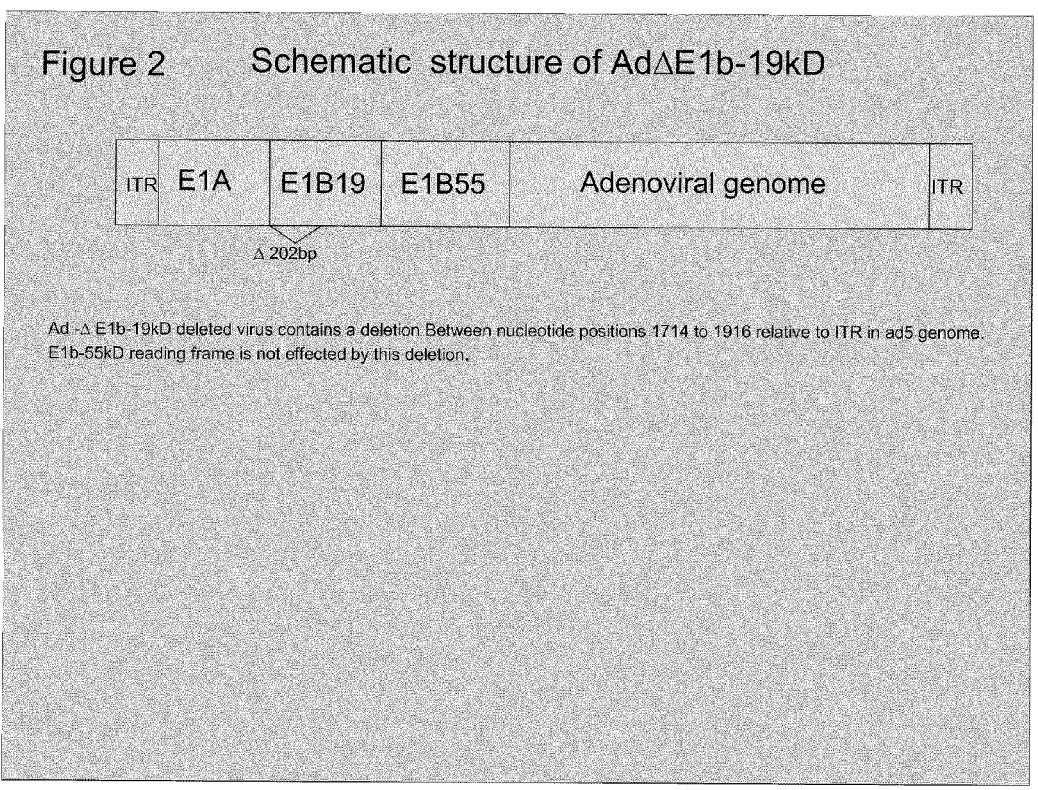
FIG. 25. Schematic of the E1a and E1b regions with the E1b-19k insertion site shown.

As shown in FIG. 24, the E1b region encodes several proteins that are defined by distinct mRNA start sites and splicing productions. E1b-19 and E1b-55k have overlapping sequences but different mRNA start sites. A 202 base pair region following the start site for E1b-19k was deleted to provide a cloning site within the E1b-19k region. The E1b-55k start site was not disrupted so that expression of E1b-55k could be retained.

Figure 28:
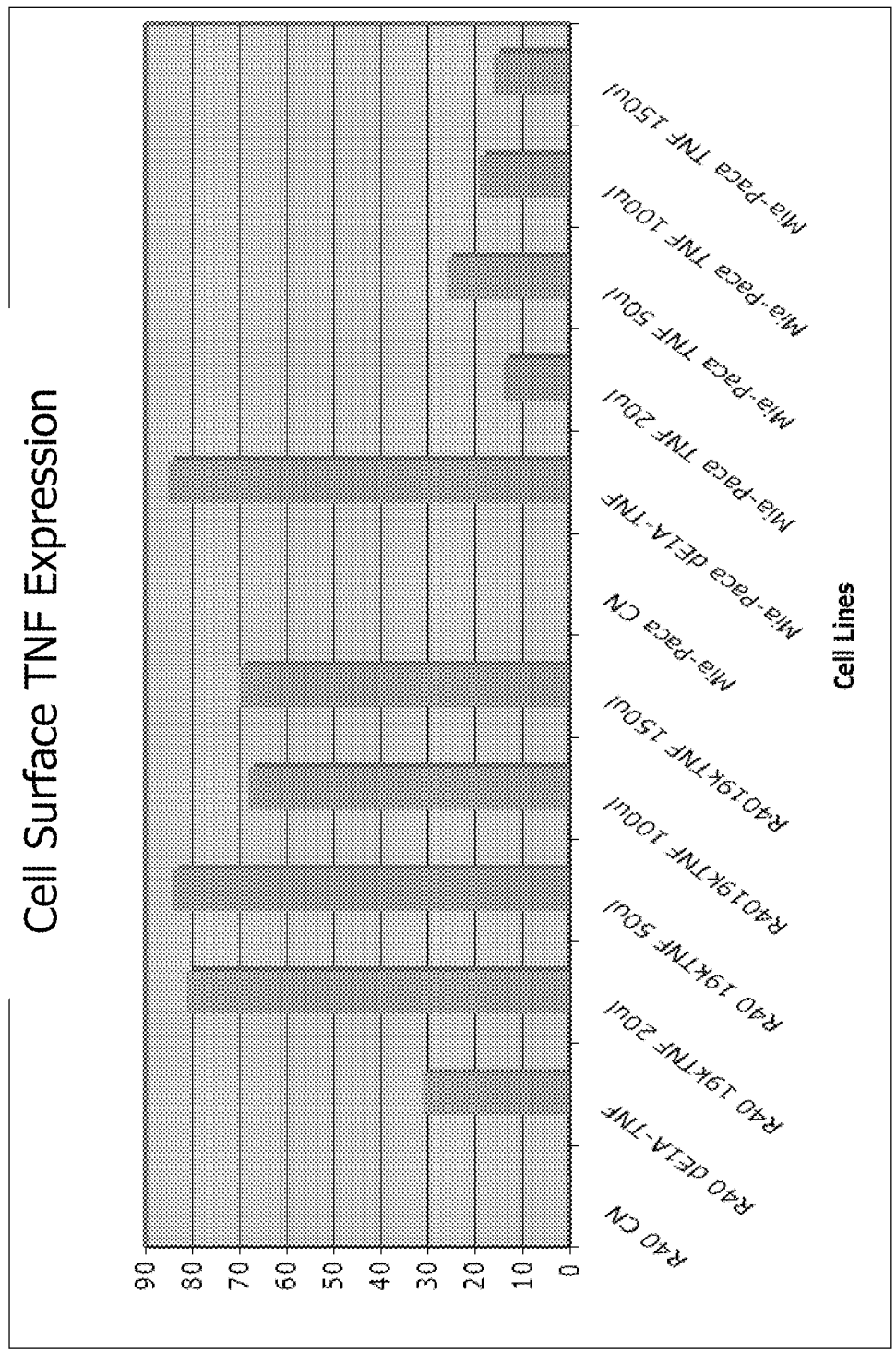
FIG. 28. Expression of TNF on tumor cell surface following infection with AD19kTNF.

Analysis of surface expression of TNF expressed from E1b-19k by flow cytometry is shown in FIG. 28. This results demonstrate abundant expression of TNF from Ad19k TNF in a) R-40 Mouse pancreatic cancer and b) MiaPaca pancreatic cancer cell lines. As a control, TNF was inserted into a commonly used adenoviral expression vector with deletion of the E1 region of the viruses and insertion of TNF. Expression of TNF is under the control of the CMV promoter, a strong promoter commonly used in adenoviral expression vectors. This vector is designated as dE1a-TNF. We have previously demonstrated that very high titers of this vector are needed to achieve detectable expression of TNF in a range of tumor cell types. In this study, dE1a-TNF is used at 750 plaque-forming units (pfu) per cell. Using 750 pfu per cell, approximately 30% of the R40 cells and 85% of the Mia-PaCa cells had detectable surface expression of TNF. Cell lysates of the Ad19kTNF vector were added to cells to determine the expression of TNF on the surface of cells. The precise concentration of viral particles was not determined in this experiment; however, is subsequent studies we have demonstrated that Ad19kTNF use at 2 pfu/cell has as much or more expression of TNF as the dE1a-TNF vector used at 750 pfu/cell. The results of the current study demonstrate that 70-80% of R-40 cells express TNF on their surface following infection with the Ad19kTNF vector compared to only about 30% of cells when infected with the dE1a-TNF vector. In Mia-PaCa cells, infection with the dE1a-TNF vector used at 750 pfu/cell results in detectable expression of TNF on about 80% of the cells while infection with lysates with the Ad19kTNF vector express TNF on about 15-25% of the cells. The detailed analysis showing the flow-cytometry data is shown in FIGS. 5b and 5c. In summary, this data shows that expression of biologically active TNF can be achieved from the Ad19kTNF vector.

Figure 29A:
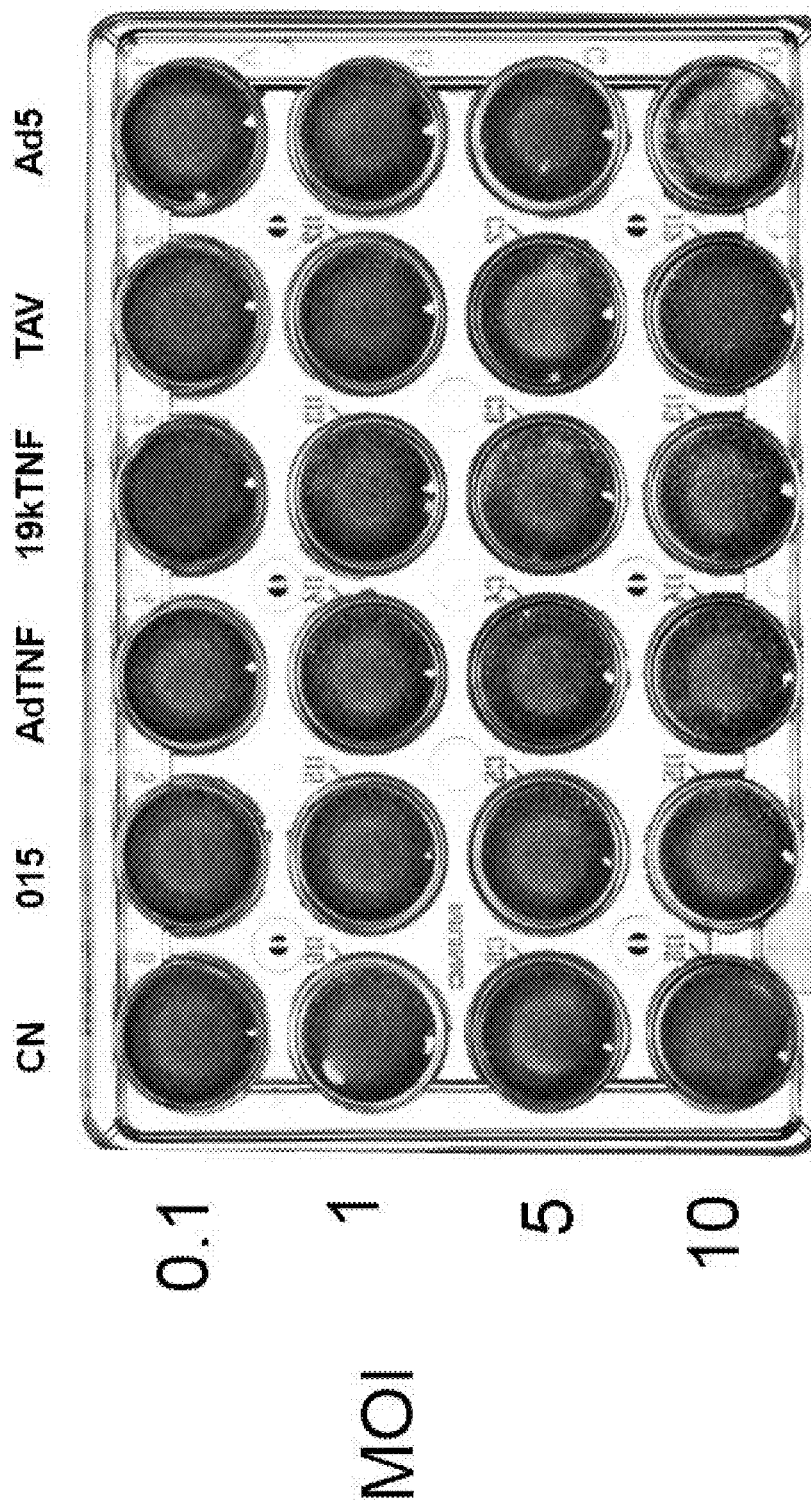
FIG. 29. Cytotoxicity assay in MRC5 (a) 3 days post infection and (b) 5 days post infection.
Figure 29B:

Cell viability assays were performed in non-transformed cells at 3 and 5 days post-infection (FIG. 29). These results demonstrate minimal cell death with all viruses tested with the exception of moderate cell death with Ad5 at the highest MOI. Significant cell death for Ad5 and Ad19k TNF viruses is observed at 5 days post infection. Notably, there is no detectable cell death with the promoter deletion virus, TAV-255, at the highest MOI out to 5 days post infection. The non-replicating virus expressing TNF demonstrates no cell death at the highest MOI out to 5 days post infection.

Figure 30A:
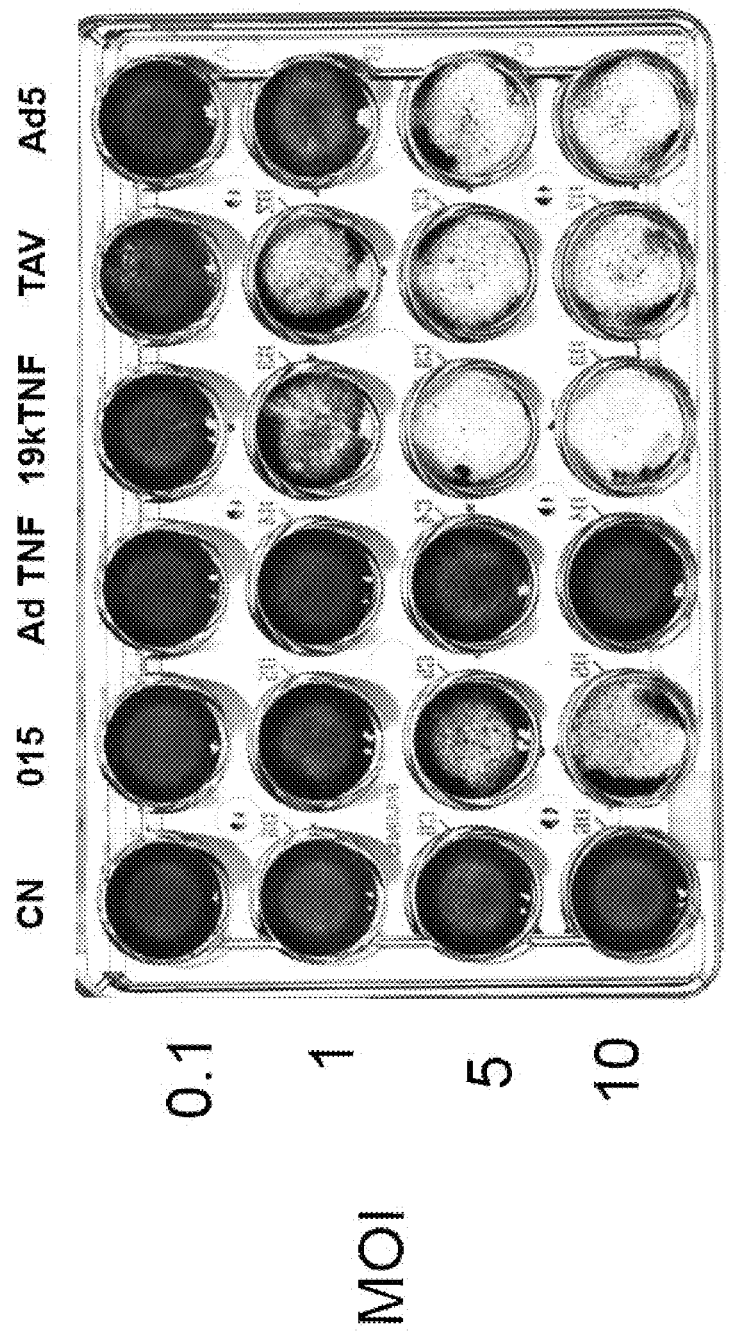
FIG. 30. Cytotoxicity assay in A549 (a) 3 days post infection and (b) 5 days post infection.
Figure 30B:
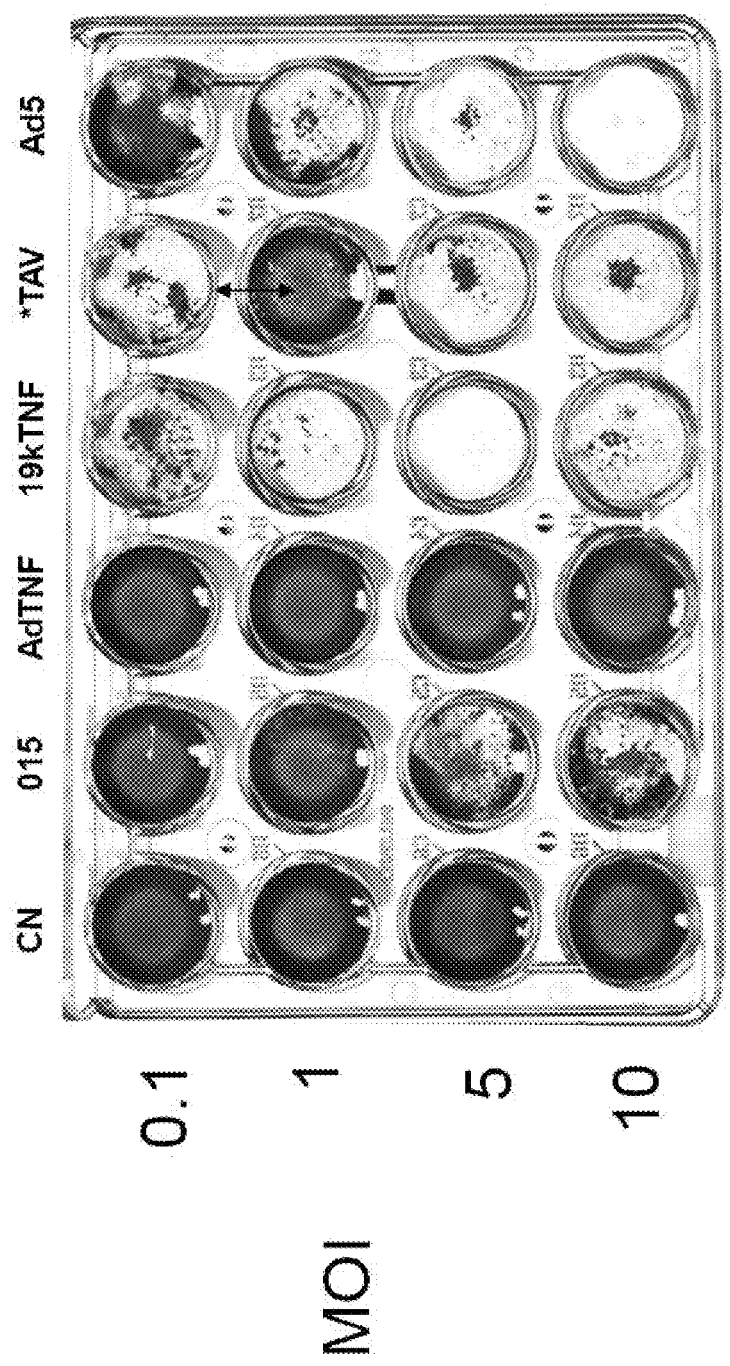

Cell viability assays were performed in transformed cells (A549) at 3 and 5 days post-infection (FIG. 30). These results demonstrate extensive cell death with Ad5, TAV and Ad19k TNF viruses at low MOIs and moderate cell death with dl1520 at the highest MOI. By 5 days post infection, significant cell death for Ad19k TNF virus at an MOI of 0.1, significantly better than observed for Ad5 alone. The non-replicating virus expressing TNF demonstrates no cell death at the highest MOI out to 5 days post infection and modest activity is noted for dl1520 at the highest MOI.

Figure 31A:
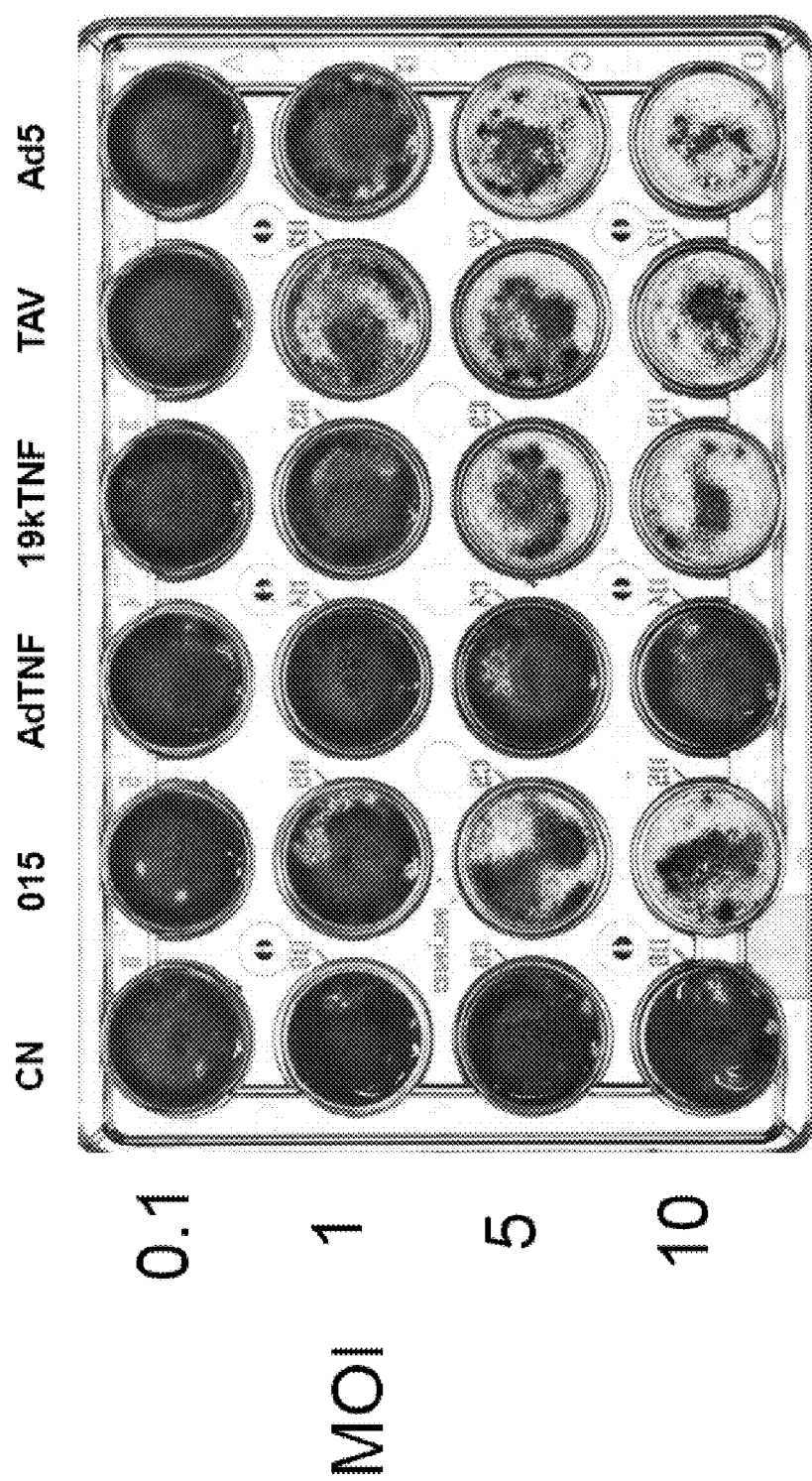
FIG. 31. Cytotoxicity assay in Panc1 (a) 3 days post infection and (b) 5 days post infection.
Figure 31B:
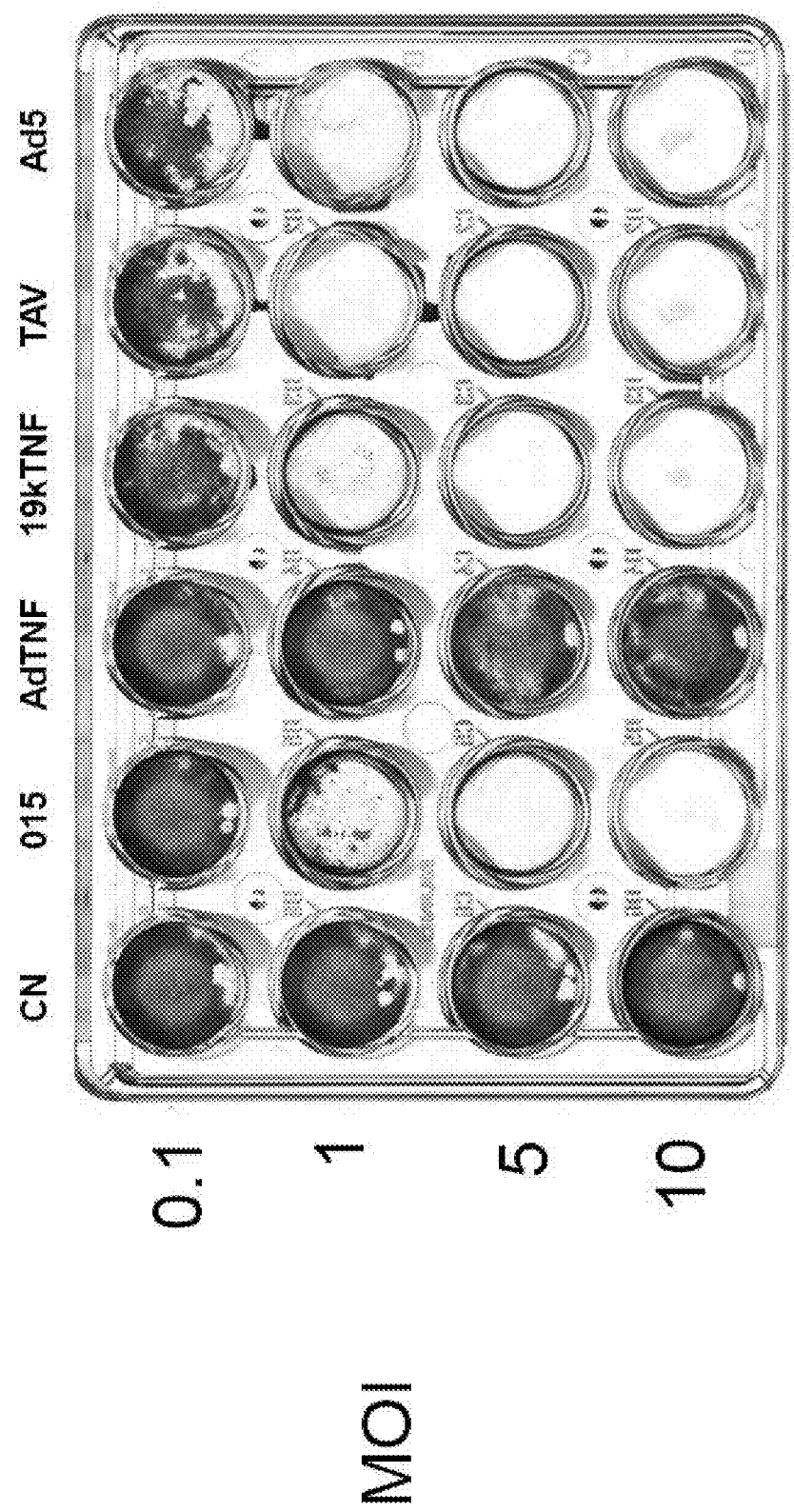

Cell viability assays were performed in transformed cells (Panc1) at 3 and 5 days post-infection (FIG. 31). These results demonstrate extensive cell death with Ad5, TAV and Ad19k TNF viruses at low MOIs and moderate cell death with dl1520 at the highest MOI. By 5 days post infection, significant cell death for Ad5, TAV and Ad19k TNF virus at an MOI of 0.1, significantly better than observed the non-replicating virus expressing TNF which demonstrates no cell death at the highest MOI out to 5 days post infection. Cytolytic activity is noted for dl1520 but higher MOIs are needed than for TAV and Ad19k TNF for similar cytolytic activity.

Figure 32A:
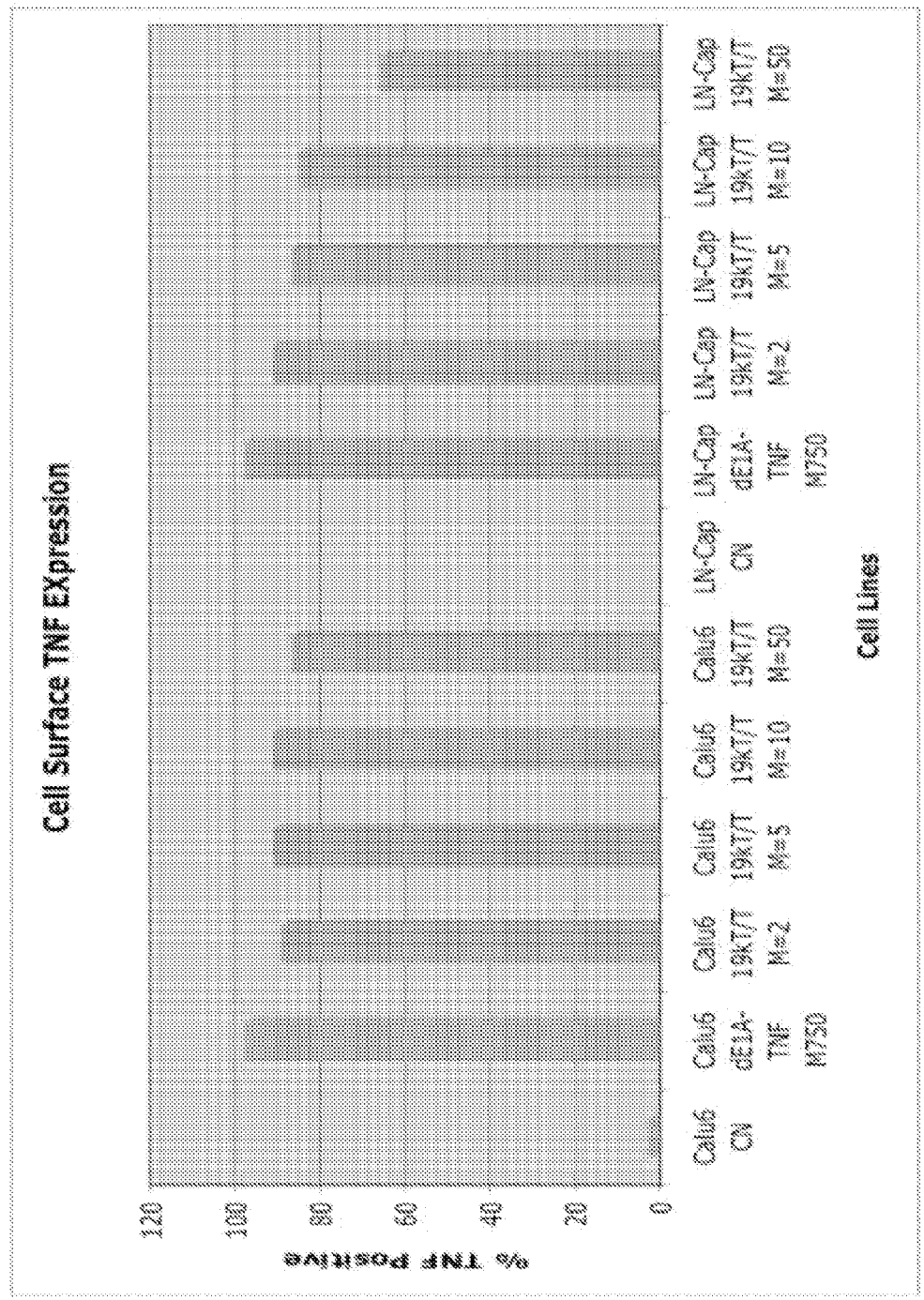
FIG. 32a-b. Analysis of surface expression of TNF by AdTAV19 kmmTNF using flow cytometry.
Figure 32B:
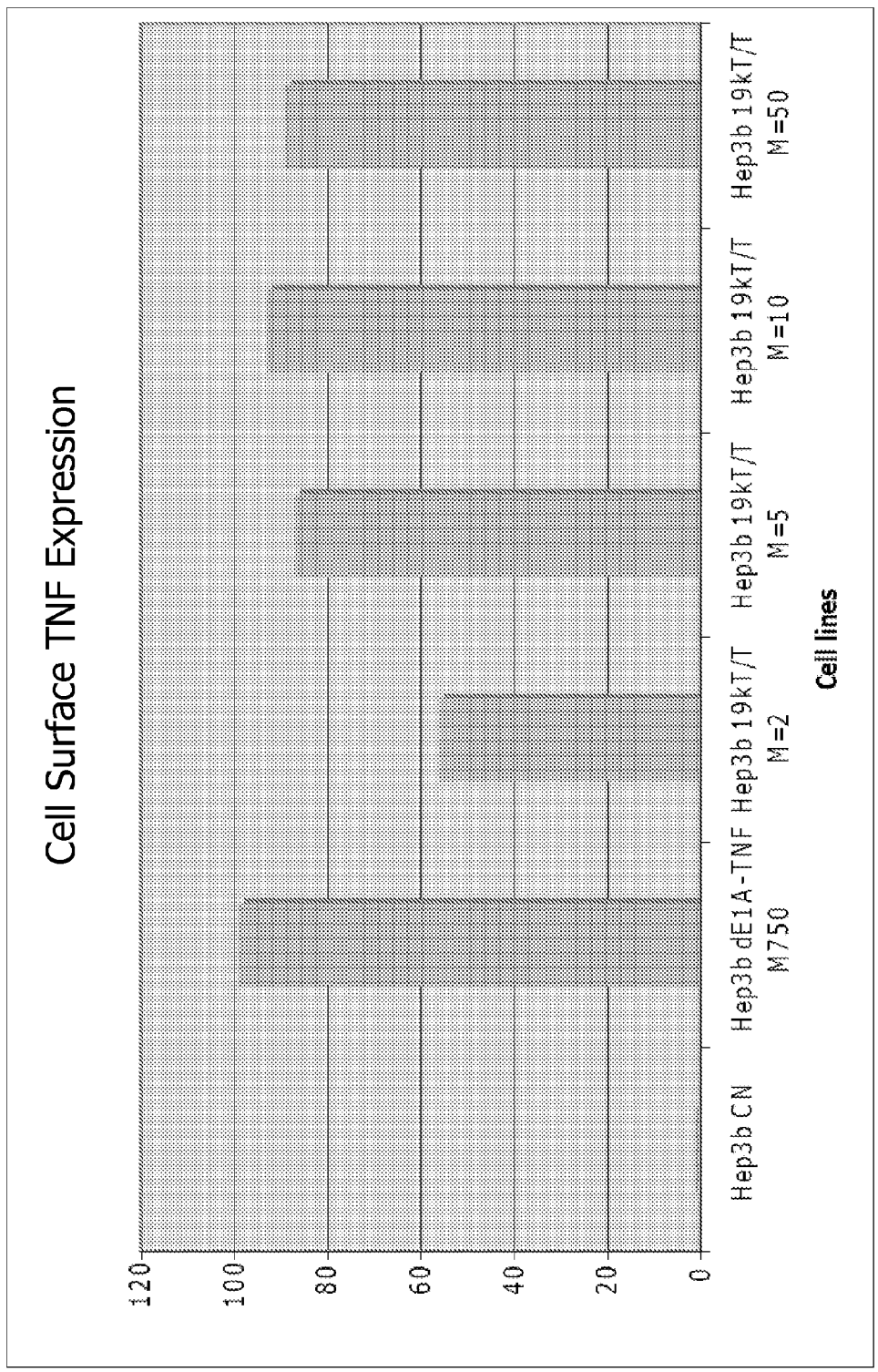
Figure 32C:
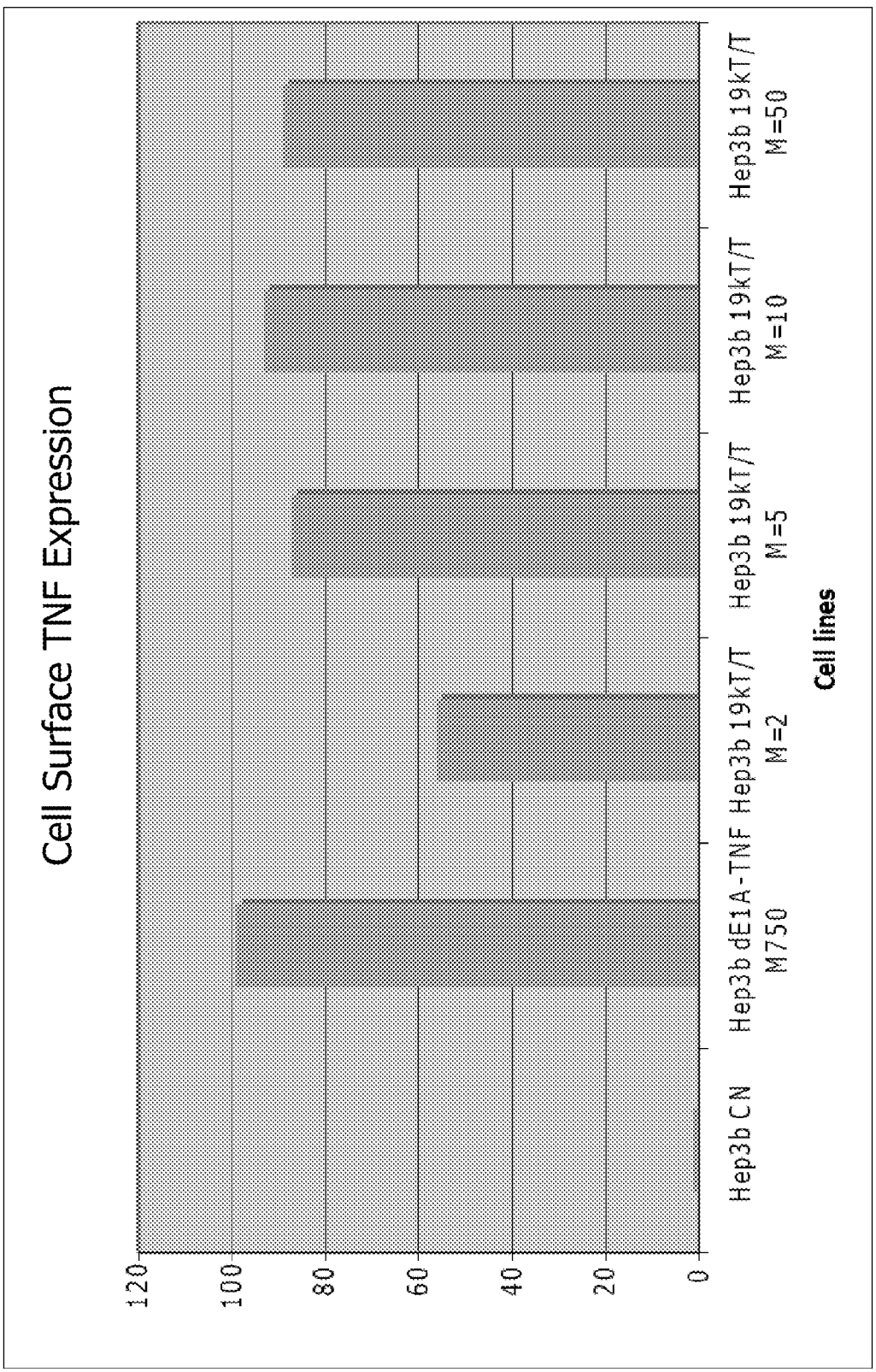

Analysis of surface expression of TNF by AdTAV19 kmmTNF using flow cytometry (FIG. 32): This analysis demonstrates abundant expression of TNF Expression from AdTAV19kTNF in a) CaLu-6, b) LnCap and c) Hep3b cancer cell lines. Abundant expression of TNF, approaching 100% of the tumor cells, is achieved with a multiplicity of infection (MOI) of 2, equaling 2 pfu/cell. As a control, dE1a-TNF and an MOI of 750 is shown. At this high MOI, over 90% of the cells in these cells lines have detectable expression of TNF. In contrast, Ad19kTNF used at 2-5 pfu/cell has detectable expression of TNF in 80-00% of cells. The detailed analysis showing the flow-cytometry data is shown in FIGS. 9c-e. In summary, this data shows that expression of biologically active TNF can be achieved from the Ad19kTNF vector at MOIs of 2 to 5, similar to the results achieved with the dE1a-TNF vector at an MOI of 750. These results further demonstrate that effective expression of TNF can be achieved with the 50 base-pair TAV-255 deletion in the E1a promoter. We have demonstrated that this promoter deletion restricts the expression of E1a and E1b in non-transformed cells while retaining expression of E1a and e1b in tumor cell lines. These results confirm efficient expression of TNF from the vector containing the TAV-255 deletion and with TNF cloned into the E1b-19k region of the virus.

Figure 33:
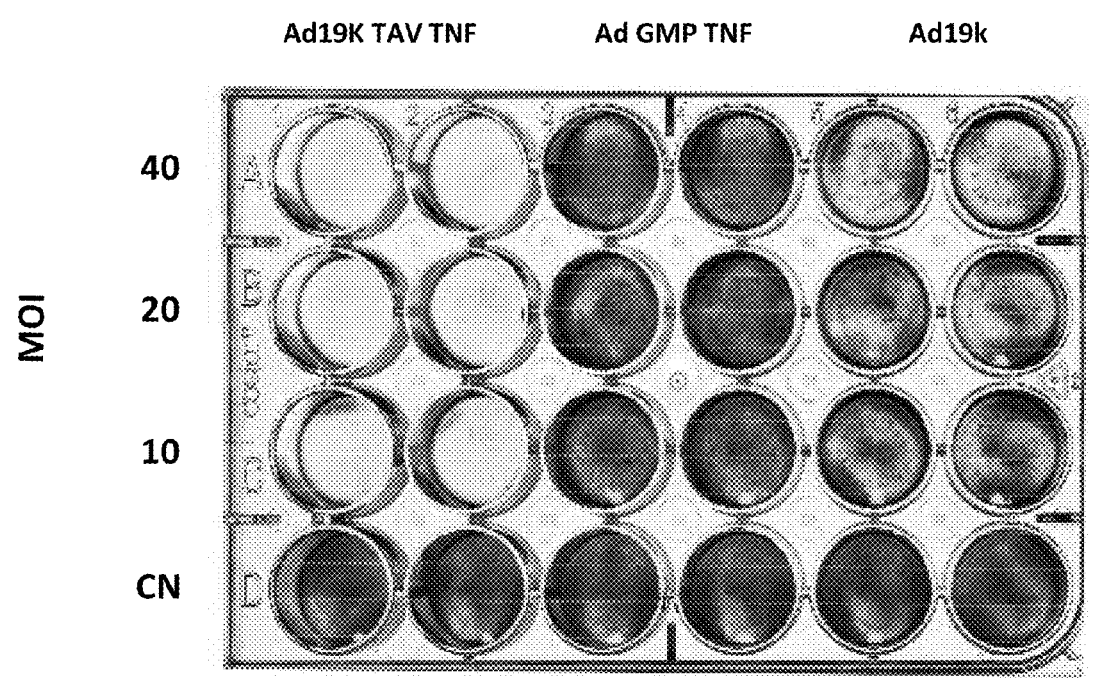
FIG. 33. Crystal Violet Assay in SK-Mel-28 (melanoma) three days post infection.

The survival of SK-Mel-28 (melanoma tumor cell) was evaluated following infection with infected with AdTAV19TNF, dE1a-TNF and Ad19k (FIG. 33). The SK-Mel-28 cell line is refractory to killing by adenoviral vectors. No significant cytotoxicity is observed with dE1a-TNF at the highest MOI and only modest cytotoxicity is observed with Ad19k. In contrast, complete cytotoxicity is observed with AdTAV19TNF at an MOI of 10, the lowest MOI tested.

Figure 34:
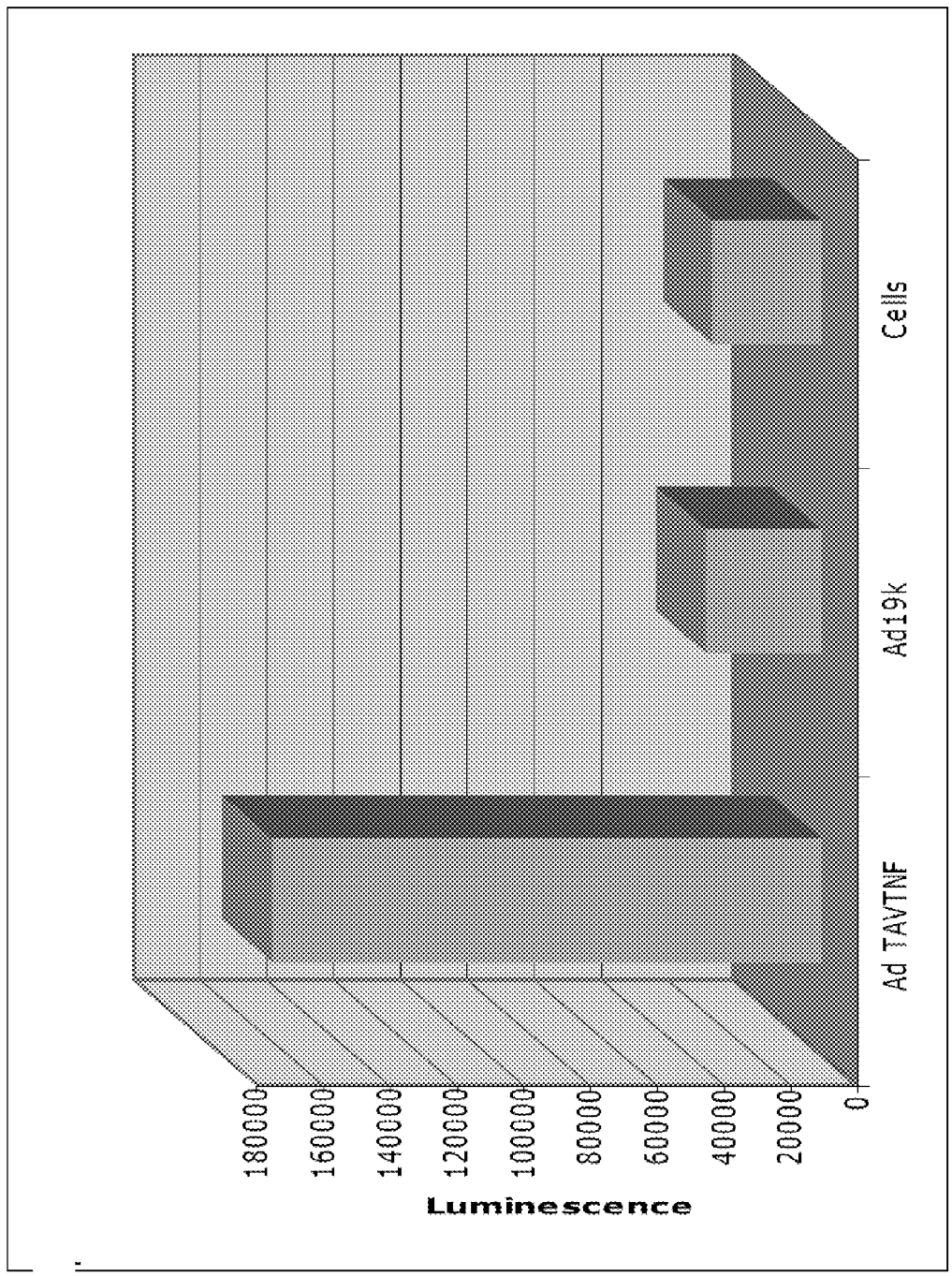
FIG. 34. Activation of caspase-3 in Hep3b cells infected with Ad19k or AdTAV19TNF at an MOI of 5, 48 hours post infection.

TNF induces cell death through induction of caspases (see FIG. 34). Activation of the TNF receptor by binding TNF results in the recruitment of death domain proteins and subsequent activation of caspase-8 and then activation of caspase-3 triggering the induction of apoptotic cell death. We determined the activation of caspase-3 in Hep3b cells infected with Ad19k or AdTAV19TNF at an MOI of 5. The results demonstrate marked induction of caspase-3 in cells infected with AdTAV19TNF. No significant increase in caspase-3 activity was observed in cells infected with Ad19k.

Figure 35:
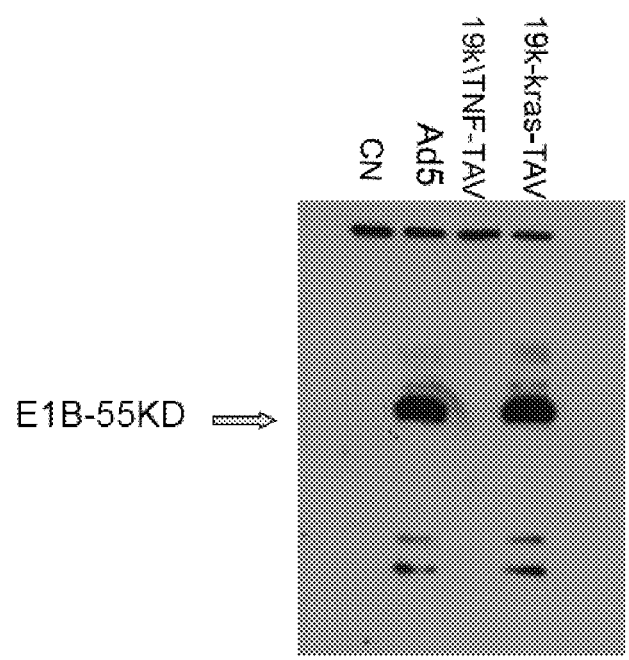
FIG. 35. E1b-55 kD expression in AD-Δ19 kD-kras/TAV at MOI of 2, 48 hours post infection.

Determination of expression of E1b-55k in vectors with E1b-19k deletions (FIG. 35): The insertion site in the E1b-19k deleted vectors was designed so that the start site of E1b-55k would not be disrupted. To determine if E1b-55k gene expression was retained, the expression of E1b-55k was evaluated in vectors with TNF or Kras inserted into the E1b-19k region. The results demonstrate normal expression of E1b-55k for the virus with Kras inserted into E1b-19k. The level of expression of E1b-55k is equivalent to the level of expression of E1b-55k observed in cells infected with wild-type Ad5. This confirms that expression of E1b-55k can be retained despite insertions of DNA into the E1b-19k region. Interestingly, there is no detectable expression of E1b-55k from the vector expressing TNF. At this point, we do not know the cause of this effect. TNF may directly inhibit the expression of E1b-55 or the nature of the insertion may diminish expression from E1b-55k. This is being evaluated.

Figure 36:
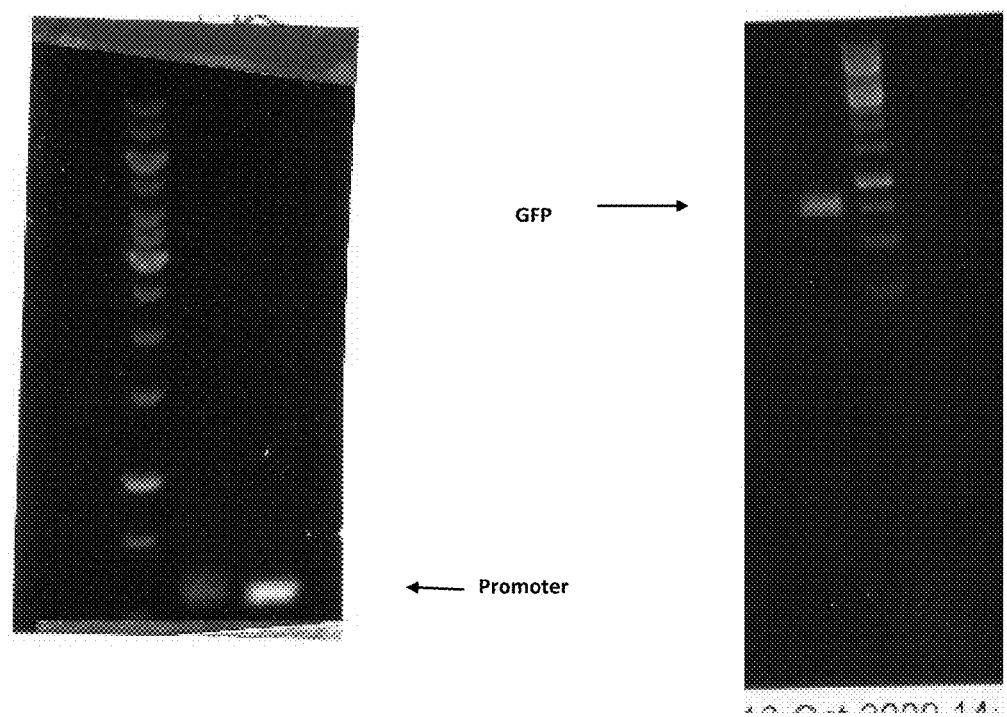
FIG. 36. PCR Amplification of GFP and E1A Promoter from Ad19kTAVhrGFP Transfection lysate FIG. 37. GFP Expression in A549 Infected at MOI of 2 With Ad19kTAVGFP.

Determination of GFP insertion into E1b-19k. Insertion of GFP into E1b-19k was demonstrated by PCR (FIG. 36).

Figure 37:
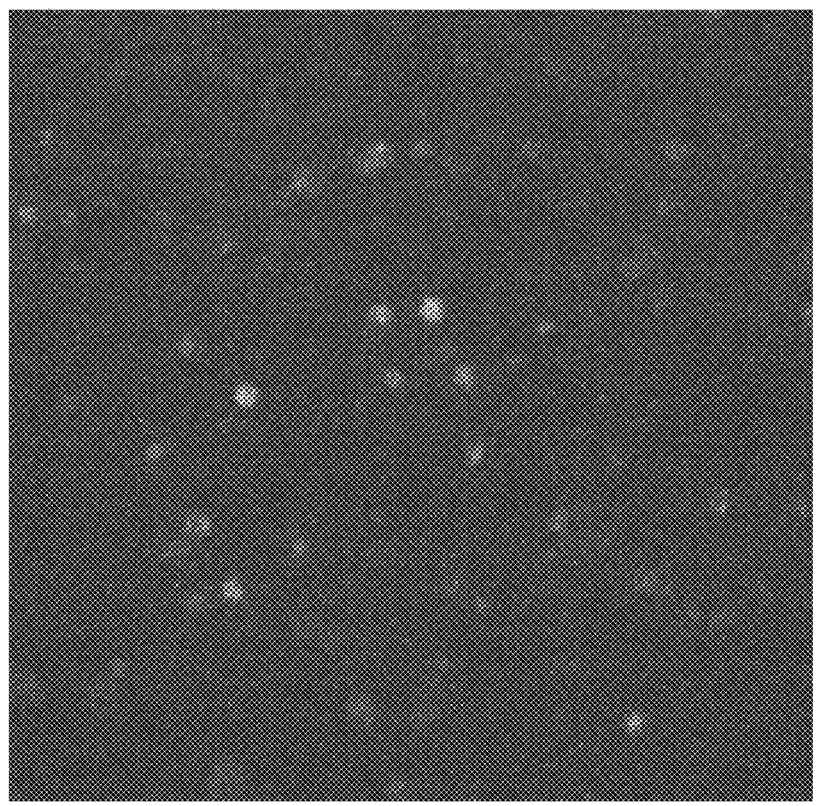

Tumor cells express GFP following infection with Ad19kTAVhrGFP (FIG. 37).

The concept of a dual function vector: Modulation of E1a enhancer can results in an expression vector that expresses E1 proteins abundantly and is lytic in tumor cells. However, this virus expresses E1 proteins at low levels and has limited lytic activity in non-transformed cells. Therefore, the viral vector could be oncolytic in tumor cells but used to express therapeutic transgenes and mutated proteins (vaccine) in non-transformed cells. We have previously demonstrated abundant expression of E1 proteins in tumor cells after infection with the E1 promoter deletion vector. In contrast, expression of E1 proteins is delayed and significantly less in non-transformed cells. See FIG. 4c.

The concept of an Oncolytic Tumor Vaccine directed at mutated Kras: Kras is down-stream of the epidermal growth factor receptor (EGFR). Mutations in Kras result in constitutive activation of the Ras pathway. Since mutated Kras is constitutively active, therapies directed at the EGFR receptor such as Erbitux and Vectivix are ineffective. Kras is commonly mutated in a variety of malignancies occurring in about 50% of colon cancers and over 90% of pancreatic cancers. Various Kras point mutations have been described and it is common to sequence for Kras mutations to determine if patients will respond to EGFR directed cancer therapies. We have cloned the most commonly described Kras mutations into the 19K expression vector.

Expression vectors from E1b-19k to enhance immunity to tumor antigens: Kras mutated proteins have been cloned into the E1b-19k expression vector in three distinct ways to provide a robust platform for expression of tumor antigens. First, DNA coding for the mutated Kras sequences was inserted into the E1b-19k region. Second, the bacterial flagellin gene was cloned into the E1b-19k region. A cloning site was introduced into the flagellin DNA sequence and Kras specific sequences were introduced into the middle of the flagellin gene. Flagellin is a highly immunogenic protein and may help enhance an immune response to Kras mutated sequences. Third, TNF was deleted from the transmembrane domain of the E1b-19K CD154-TNF construct and the mutated Kras DNA sequences were ligated to CD154. This provide for abundant expression of mutated Kras peptides on the surface of the cell. Depending on the construct used, Kras could be restricted to expression on the surface of the tumor cell or be allowed to be proteolytically cleaved allowing for release of the Kras mutated peptide to immune cells and lymph nodes for immune recognition and processing.

Accordingly, in one embodiment, a recombinant virus is provided that includes a E1b-19K insertion site. The E1b-19K insertion site can be used, e.g., for the insertion of a DNA sequence. The inserted DNA sequence can encode any sequence, including, e.g., a transgene, cancer gene, or mutated DNA sequence. In one embodiment, the transgene is TNF. In another embodiment, the transgene is kras. In yet another embodiment, the transgene is a mutated p53 sequence.

In one embodiment, the sequence of E1b-55K, or a functional portion thereof, is maintained. In one embodiment, the sequence of the E1b-55K start site is maintained. In one embodiment, the insertion site comprises the deletion of about 1 to about 200, at least about 100 about 100 to about 200, about 1 to about 150, about 1 to about 50, or at least about 10 base pairs between the start site of E1b-19K and the start site of E1b 55K. In one embodiment, the insertion site comprises the deletion of 202 base pairs following the start site of E1b-19K.

VII. Viral Vectors

In one embodiment, the modified genes and sequences described herein are employed within a viral vector. The terms "viral vector" and "virus" are used interchangeably herein to refer to any of the obligate intracellular parasites having no protein-synthesizing or energy-generating mechanism. The viral genome may be RNA or DNA contained with a coated structure of protein of a lipid membrane. The viruses useful in the practice of the present invention include recombinantly modified enveloped or non-enveloped DNA and RNA viruses, preferably selected from baculoviridiae, parvoviridiae, picornoviridiae, herpesviridiae, poxyiridae, or adenoviridiae. The viruses may be naturally occurring viruses or their viral genomes may be modified by recombinant DNA techniques to include expression of exogenous transgenes and may be engineered to be replication deficient, conditionally replicating, or replication competent. Chimeric viral vectors which exploit advantageous elements of each of the parent vector properties (See e.g., Feng, et al. (1997) Nature Biotechnology 15:866-870) may also be useful in the practice of the present invention. Minimal vector systems in which the viral backbone contains only the sequences need for packaging of the viral vector and may optionally include a transgene expression cassette may also be produced according to the practice of the present invention. Although it is generally favored to employ a virus from the species to be treated, in some instances it may be advantageous to use vectors derived from different species that possess favorable pathogenic features. For example, equine herpes virus vectors for human gene therapy are described in WO98/27216. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in WO 97/06826.

Preferably, the viral vector is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are vectors derived from human adenovirus types 2 and 5.

In one embodiment, the modified regulatory sequence is operably linked to a sequence encoding a protein. In one embodiment, at least one of the E1a and E1b genes (coding regions) is operably linked to the modified regulatory sequence. In one embodiment, at least one of the E1a and E1b genes is present in the wild-type form.

In one embodiment, the E1a gene is operably linked to the modified regulatory sequence. In another embodiment, the E1a gene is the wild-type. In another embodiment, the E1a gene is modified to selectively express a E1a isoform.

In yet another embodiment, and/or a modified E1b gene is operably linked to the wild-type promoter region. In another embodiment, the modified E1a gene and/or the modified E1b gene is operably linked to a modified regulatory sequence.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic sequences may be of variable lengths, some polynucleotide elements may be operably linked but not directly flanked and may even function in trans from a different allele or chromosome.

In another embodiment, the modified regulatory sequence is operably linked to a cytotoxic transgene. The term "cytotoxic transgene" refers to a nucleotide sequence the expression of which in the target cell induces lysis or apoptosis of the cell. The term cytotoxic transgene includes, but is not limited to, tumor suppressor genes, toxin genes, cytostatic genes, pro-drug activating genes, or apoptotic genes.

In one embodiment, any of these cytotoxic transgenes may be inserted into an E1b-19K insertion site as described above.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4 gene, the BRCA-1 gene, the BRCA-2 gene, the WT-1 gene, the retinoblastoma gene (Lee, et al. (1987) Nature 329:642), the MMAC-1 gene, the adenomatous polyposis coli protein (Albertsen, et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3p21.3. (Cheng, et al. 1998. Proc. Nat. Acad. Sci. 95:3042-3047), the MTS 1 gene, the CDK4 gene, the NF-1 gene, the NF2 gene, and the VHL gene.

The term "toxin gene" refers to nucleotide sequence, the expression of which in a cell produces a toxic effect. Examples of such toxin genes include nucleotide sequences encoding pseudomonas exotoxin, ricin toxin, diptheria toxin, and the like.

The term "pro-apoptotic gene" refers to a nucleotide sequence, the expression thereof results in the programmed cell death of the cell. Examples of pro-apoptotic genes include p53, adenovirus E3-11.6K, the adenovirus E4orf4 gene, p53 pathway genes, and genes encoding the caspases.

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5-fluorouracil, a potent antitumor agent). The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "cytokine gene" refers to a nucleotide sequence, the expression of which in a cell produces a cytokine Examples of such cytokines include GM-CSF, the interleukins, especially IL-1, IL-2, EL-4, IL-12, IL-10, IL-19, EL-20, interferons of the α, β and gamma subtypes especially interferon α-2b and fusions such as interferon α-2α-1.

VIII. Transformed Cells

The vectors can be used to transform cells in vitro or in vivo. The cells may be neoplastic cells and/or normal cells.

A "neoplastic cell" is a cell displaying an aberrant growth phenotype characterized by independence of normal cellular growth controls. As neoplastic cells are not necessarily replicating at any given time point, the term neoplastic cells comprise cells that may be actively replicating or in a temporary non-replicative resting state (G1 or G0). Localized populations of neoplastic cells are referred to as neoplasms. Neoplasms may be malignant or benign. Malignant neoplasms are also referred to as cancers. Neoplastic transformation refers the conversion of a normal cell into a neoplastic cell, often a tumor cell. Cells that are not neoplastic are referred to as "normal" or "non-neoplastic."

IX. Methods of Tumor-Selective Expression

In one embodiment, the recombinant virus exhibits selective expression. In particular, the recombinant virus permits expression in neoplastic cells, but attenuates expression in normal cells.

Accordingly, in one embodiment, a method of selectively expressing a peptide (e.g., a protein) in a target cell comprises contacting a cell with a recombinant virus comprising a deletion mutant E1a regulatory sequence operably linked to a nucleotide sequence encoding a peptide. In this context, the peptide can be of any length, including proteins and portions thereof. In one embodiment, the peptide is associated with viral replication, such as E1a and/or E1b. In another embodiment, the peptide is associated with cancer.

In another embodiment, a method of selectively expressing a peptide in a target cell comprises contacting a cell with a recombinant virus that selectively expresses a single E1a isoform, e.g., E1a-12S or E1a-13S.

In yet another embodiment, a method of selectively expressing a peptide in a target cell comprises contacting a cell with a recombinant virus comprising a transgene inserted into an E1b-19K insertion site.

In one embodiment, the target cell is a neoplastic cell, such as a cancer cell. In this case, the peptide is expressed, preferably at levels that approximate wild-type expression. In one embodiment, expression (as measured by mRNA expression or Western blot) is at least 75%, at least 80%, at least 90%, at least 95%, or at least 99% of wild-type expression.

In another embodiment, the target cell is a normal cell. In this case, peptide expression is selectively attenuated compared to wild-type expression. In one embodiment, expression (as measured by mRNA expression or Western blot) is reduced to no more than 25%, no more than 15%, no more than 10%, no more than 5%, no more than 3%, or no more than 1% of wild-type expression. In one embodiment, attenuation of about 0% to about 5% is achieved.

These methods of selective expression may be practiced in vitro or in vivo.

X. Methods of Treatment

"Methods of treating a disease," as used herein, refers to methods of treating a disease state, a condition caused by a disease state, or disease symptoms. "Treating" the disease includes one or more of: addressing a physiological cause of the disease, addressing a physiological cause of a disease symptom, reducing the severity of the disease, slowing the progression of the disease, ameliorating a symptom of the disease, and shortening the duration of the disease (e.g., hastening remission).

The "subject" as used herein is a subject in need of treatment for cancer. The subject is preferably a human, but also may include laboratory, pet, domestic, or livestock animals. In one embodiment, the subject is a mammal.

In one embodiment, a method of treating cancer comprises administering a pharmaceutical formulation comprising a recombinant virus as described above. The pharmaceutical formulation may be administered systemically or locally to treat a wide variety of stages and types of cancers including, but not limited to, lung, pancreas, prostate, cervix, ovarian, liver, head and neck, bladder, breast, colon and rectal, endometrial, kidney, leukemia, skin cancers (melanoma and non-melanoma), non-Hodgkin lymphoma, and thyroid cancers.

Pharmaceutical formulations comprising the vectors are also provided. The vectors can be formulated for administration by methods known in the art. Particular delivery systems may be formulated for intramuscular, intravenous, intraarterial, or intratumoral injection.

The formulations may contain pharmaceutically acceptable auxiliary substances as required to approximate physiological conditions, such as pH-adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the active agent in the pharmaceutical formulations can vary widely, e.g., from less than about 0.1%, usually at or at least about 2% to as much as 20% to 50% or more by weight, and will be selected primarily by fluid volumes, viscosities, etc., in accordance with the particular mode of administration selected.

The formulations and methods described herein may be practiced alone or in combination with conventional chemotherapeutic agents or treatment regimens.

XI. Examples

The following examples are meant to illustrate certain embodiments of the invention and not to limit the scope of the invention described herein.

A. E1a Transcriptional Control Region Deletions

Cell lines, viruses, and plasmids: The HEK-293A (adenovirus E1-transformed human embryonic kidney cells), HeLa (cervical cancer), A549 (lung cancer), LNCaP (prostrate cancer), Calu-6 (lung cancer), PANC-1 (pancreatic cancer), AsPc-1 (pancreatic cancer), and MRC-5, WI-38, and IMR-90 (lung fibroblast) cells were obtained from the American Type Culture Collection (ATCC), and were grown in Dulbecco's modified Eagle's medium supplemented with 10% fetal calf serum in the presence of 5% $CO_2$. Primary cells were contact inhibited by growing them to 100 percent confluency and followed by prolong incubation in complete medium.

Reconstruction of mutation into the Ad5 genome: Wild type Ad5 (Dl309), partial deletion of E3 region, and various deletion mutants of Ad5 E1A promoter/enhancer; Dl309-6, Dl340-12, and Dl87 were kindly provided by Patrick Hearing (Stony Brook University, USA). To construct TAV-255 virus, the E1a promoter enhancer region was deleted using the adenoviral vector plasmid pXC1 (Microbix Biosystem Inc.) using QuickChange II XL site-directed mutagenesis kit (Stratagene, La Jolla, Calif.) according to its recommended manual. Primer d194_243_F 5'-AAA GTG ACG TTT TTG GTG TGC GCC GGT GTT TTG GGC GTA ACC GAG TAA GAT TTG GCC A-3' (SEQ ID NO:1) and d194_243_R 5'-TGG CCA AAT CTT ACT CGG TTA CGC CCA AAA CAC CGG CGC ACA CCA AAA ACG TCA CTT T-3' (SEQ ID NO:2) were used for this deletion. The obtained plasmids named pXC1_TAV-255 were amplified in E. coli, sequenced, and purified using HiPur Plasmid Filter Midiprep Kit (Invitrogen, Carlsbad, Calif.). To obtain adenovirus TAV-255, pXC1_TAV plasmids were co-transfected with pJM17 into HEK-293 cells (ATCC, Manassas, Va.) using the Fugene®6 Transfection Reagent (Roche, Switzerland). Cells were overlaid with 1.0% Sea Plaque Agarose in culture medium to obtain single plagues in 12 days. After two rounds of plaque purification, viruses from a single plaque were amplified in HEK-293 cells. Viral DNA was extracted from culture supernatant using AccuPrep Genomic DNA Extraction Kit (Bioneer Inc., Alameda, Calif.) and sequenced to confirm expected mutations.

Reconstruction of deletion mutation into the dl309 genome: All the deletions were made initially in pXC1 using site directed mutagenesis kit (Quick change II XL) obtained from Stratagene, Calif., according to recommendation by the manufacturer. All the primers used to make specific deletion are as follows (SEQ ID NOs:3-12, respectively): for dl212 (dl212S-CGG TGT ACA CAG GAA GTG ACA ATC GGT TTT AGG CG and dl212 As-CGC CTA AAA CCG ATT GTC ACT TCC TGT GTA CAC CG), dl220 (dl220S AGT GAC AAT TTT CGC GCA GGC GGA TGT TGT AGT A and dl220AS: AGT GAC AAT TTT CGC GCA GGC GGA TGT TGT AGT A), dl275 (dl275S: GTA ACC GAG TAA GAT TTG GCC ATG GAA AAC TGA ATA AGA GG and dl275AS: CCT CTT ATT CAG TTT TCC ATG GCC AAA TCT TAC TCG GTT AC), dl200 (dl200S: GCG CCG GTG TAC ACA GAC AAT TTT CGC GCG and dl200AS: CGC GCG AAA ATT GTC TGT GTA CAC CGG CGC), dl230 (dl230S: TTC GCG CGG TTT TAG GCT GTA GTA AAT TTG GGC G and dl230AS: CGC CCA AAT TTA CTA CAG CCT AAA ACC GCG CGA A). The mutated plasmids were first sequence to verify the desired mutation and letter amplified using HiPur Plasmid Midiprep Kit (Invitrogen, Carlsbad, Calif.). To create the desired mutation in dl309 genome, mutated pXC1 containing desired mutation were co-transfected with pJM17 into HEK-293 cells (ATCC, Manassas, Va.) using the Fugene6 Transfection Reagent (Roche, Switzerland). Cells were overlaid with 1.0% Sea Plaque Agarose in culture medium to obtain single plagues in 10 days. After plague purification twice, viruses from a single plaque were amplified in HEK-293 cells. Viral DNA was extracted from the culture cells infected with mutant virus using AccuPrep Genomic DNA Extraction Kit (Bioneer INc, Alameda, Calif.) and PCR amplified and latter sequenced to confirm expected mutations.

Virus infection, multiplication, and quantification: All the viruses were multiplied in HEK-293A cells. Cells were infected with MOI of 5 (for Ad5 genome) or 10 (for dl309 genome) and after 3 days post infection, cells were collected and re-suspended in complete medium and lysed by 3 cycles of freeze/thaw. Lysates were clarified by passing through 0.4 µm filter (Millipore, USA). Glycerol was added to the samples to a final concentration of 10% (v/v) and frozen to −80° C. To quantify the virus titer, plaque assay were performed as described by Clontech, USA.

Preparation of Cell Lysates and Immunoblot Analysis: for Western Blot Analysis, Cell extracts from various cell lines were prepared by infecting cells with adenoviruses with MOI of 5 and whole cell lysates were prepared using M-PER® mammalian protein extraction reagent (Pierce, USA) at various time points post infection. Protein was estimated using the Bradford reagent (Bio-Rad, USA), and 25 µg of protein samples were boiled for 5 min in sample buffer containing 2% SDS, 100 mM dithiothreitol, 0.05 M Tris-HCl (pH 6.8), 10% glycerol, and 0.1% bromophenol blue. Proteins were analyzed on 4 to 12% bis-Tris gels according to the manufacturer's instructions (Invitrogen, CA). The protein samples were separated by SDS-PAGE, run on a 4-12% Bis-Tris gel (for Ad5 genome), and transferred onto a polyvinylidene difluoride (PVDF) membrane, Immobilon-$P^{sq}$ (Millipore, USA) as described by manufacturer. The E1a and/or E1b proteins were detected, e.g., by using polyclonal antibody against Ad2 E1A protein (Santa Cruz, USA) and monoclonal antisera against E1b-55k protein, received from Dr. A. J. Levine (New Jersey, USA).

Real time quantitative-PCR analysis: RNA was extracted using the RNase Easy plus mini kit (Qiagen, USA) and 1.5 µg of total RNA was reverse-transcribed into cDNA using AMV Reverse Transcriptase (Invitrogen, USA). Quantitative-PCR (Q-PCR) was performed in triplicate using Power Cyber green reagent from Applied Biosystems, and the reaction was performed on an AB Prism 7900 HT sequence detection system. RNA samples without reverse transcriptions were used as a control. Data were analyzed using SDS 2.2.1 software provided by the Applied Biosystems, USA.

Plasmid construction: Adenovirus (Ad5) E1A Promoter/ Enhancer DNA sequence (+52 to −357) was PCR amplified using the primers Ad143F and Ad552R (Forward 5'GGGG-TACCAC ATG TAAG CGAC GGATG TGGC3' (SEQ ID NO:13) and Reverse 5'AAACTCGAGCCCGGTGTCGG AGCGGCT3' (SEQ ID NO:14)) having 5' BamHI and XhoI restriction sites, respectively and inserted into luciferase reporter vector pGL3-Basic, a promoter-less and enhancer-less vector (Promega, USA) and named as pE1AP/EGL3. Plasmid was sequenced (Eton Biosciences, USA) to verify the E1A promoter/enhancer accuracy.

Transient transfection and luciferase activity: For transient transfection experiments, cells were plated into 6-well plates ($5 \times 10^5$ cells/well) the day before transfection. Cells were transfected by the PolyFect® mediated gene transfer method as described in Qiagen manual. Briefly, 25 micro liter of polyFect reagent was mixed with 125 microliter of DMEM (Highclone) containing 1 microgram of luciferase reporter plasmid (pE1AEG13) or the luciferase pGL3-Control vector (Promega, Madison, USA), and 20 ng (ratio 50:1) of the *Renilla* luciferase expression vector pRLCMV (Promega) as an internal control to normalize the values obtained with the luciferase construct. Mixture was incubated for 10 min at room temperature to allow the formation of complexes. The mixture was then diluted in 1.0 ml of DMEM and added to the cell cultures. Cells were cultured for 24 to 48 h, and lysed with passive lysis buffer (Promega). Firefly and *Renilla* luciferase activity was measured by the Dual luciferase assay kit (Promega, USA), as specified by the manufacturer, in a luminometer, Veritas (Turner Biosystems, CA, USA). All experiments were performed at least three times and represent the relative luciferase activity as an average.

Cell viability assay: Cell viability assays were performed in triplicate using Cell Counting Kit-8 (Dojindo, Rockville, USA) according to the manufacturer's instructions. Briefly, cells (MRC-5, A549, PANC-1, or AsPC-1) were seeded in 96 wells cell culture dishes at a density of $1 \times 10^4$ per well. The following day, cells were infected with virus (Wt Ad5, TAV-255, ONYX-015, dl309, or dl200+230) with a MOI of 5. Subsequently, virus were aspirated, fresh medium was added to each well and incubated for 4-6 days. To each well, 10 μl of reagent was added and incubated in a $CO_2$ incubator for 4 h, and then the plate was read at 450 nm in a GENious pro (Tecan, USA), 96 well plate reader. Absorbance was recorded, and cell viability was calculated as follows:

$$\text{Cell viability} = \frac{A_{450} \text{ nm means value of infected cells}}{A_{450} \text{ nm means value of uninfected cells}} \times 100\%$$

Cytopathic effect was also visualized under the light microscope, and photographed at 100× magnification. Crystal violet experiments to quantify cell viability were also performed in some instances (Fuego, J., et al. (2003). Preclinical characterization of the antiglioma activity of a tropism-enhanced adenovirus targeted to the retinoblastoma pathway. Journal of the National Cancer Institute 95: 652-660).

B. Selective Expression of E1a Isoforms 12S and 13S

Viruses and Cells: A549 (lung carcinoma), Calu-6 (lung carcinoma), Panc-1 (pancreatic carcinoma), LnCaP (prostate adenocarcinoma), Hep-3b (hepatocellular carcinoma), and MRC-5 and WI-38 (lung fibroblast) cells were obtained from the American Type Culture Collection (ATCC), and were grown in Dulbecco's modified Eagle's medium supplemented with 10% fetal calf serum in the presence of 5% $CO_2$ except LnCap, which was maintained in RPMI supplemented with 10% fetal calf serum, 1% sodium carbonate, 1% sodium pyruvate, and 1% non-essential amino acids. MRC5 and WI-38 cultures were contact inhibited by growing them to 100% confluency followed by a 5 day incubation with contact inhibition before infection. PM975 and dl1500 viruses were provided to us by Dr. Arnold Berk at UCLA.

Western Blot Analysis: Sample whole cell lysates were prepared using M-PER mammalian protein extraction reagent (Pierce) with 1 μl/ml HALT protease inhibitor (Pierce) at various time point post infection. Protein was estimated using the Bradford reagent (Bio-Rad, USA), and 20 mg of protein samples were boiled. Samples were electrophoresed on 1.5 mm, 4-12% Bis-Tris gels (Invitrogen, CA) in NuPAGE MOPS SDS running buffer for 60 min at 190V. The samples were transferred onto a polyvinylidene difluoride (PVDF) membrane, Immobilon-Psq (Millipore, USA) for 60 min at 100V. Following transfer, the membranes were blocked for 60 min in T20 (TBS) blocking buffer (Thermo Scientific) with gentle agitation. Following blocking, the membranes were incubated in a 1:250 dilution of adenoviral E1A polyclonal antibody (#sc-430, Santa Cruz Biotechnology) diluted in blocking buffer overnight (12-18 h) at 4° C. The membranes were washed with TBST, incubated at room temperature for 30 min with horseradish peroxidase conjugated anti-rabbit IgG (#sc-2357, Santa Cruz Biotechnology) at a 1:2000 dilution in TBST, rinsed three times with TBST for 5 min, and then washed in TBS for 5 min. The membranes were blotted dry, incubated in 2 ml SuperSignal West Pico Chemiluminescent Substrate (Pierce, Rockford, Ill.), and blotted dry. The blots were placed in a developing folder and transferred into a film cassette. The membranes were exposed to film (Denville Scientific, Metuchen, N.J.). Exposures of 2 and 5 sec were obtained.

Cytotoxicity Assay: Cell viability assay were performed in triplicate using Cell Counting Kit-8 (Dojindo, Rockville, USA). Cells were seeded in 96 wells cell culture dishes at a density of 1000 per well. The plates were treated 16 hour after plating with the WT, Onyx-015, PM975, or dl1500 viruses at various MOI's with 10 μl of a viral/culture media solution. The plates were incubated for the desired length of time at 37° C. and 5% $CO_2$. After the incubation, the samples were treated with 10 μl of Dojindo CCK-8 solution to each well. Plates were read at 450 nm using a GENious pro (Tecan, USA) 96 well plate reader after 4 hours of incubation.

C. E1b 19K Clone Insert

Virus Construction: Ad TAV-255/dl19kCD154-TNF constructed as follows: Plasmid pXC1 (Microbix, Ontario, Canada) was used to delete 50 bp of E1A enhancer/promoter element from 194-254 relative to left arm of Ad 5 inverted terminal repeat by site directed mutagenesis. The resulting plasmid was modified to contain a Sal I at bp1716 and XhoI at 1916, which results in deletion of E1b-19 KD protein upon restriction of these enzymes. CD154-TNF was PCR amplified using pcDNA3CD154-TNF plasmid and cloned into Sal I and Xho I sites of described plasmid. Recombinant virus was made by homologous recombination between plasmid JM17 and pXC1 expression plasmid containing membrane stabilized TNF cassette in 293 cells. Briefly, 293 cells were grown to 60-70% confluency at the day of transfection. Cells and the supernatant were collected 10 days post-infection. After three cycles of freeze-thaw, plaque assay was performed, individual plaques were purified, and DNA from recombinant viruses was isolated and characterized for the expression of TNF molecules.

What is claimed is:

1. A recombinant adenovirus-comprising:
   (i) a DNA sequence inserted into an E1b-19K insertion site, wherein the insertion site is located between the start site of E1b-19K and the start site of E1b-55K; and
   (ii) a modified E1a regulatory sequence, wherein at least one Pea3 binding site, or a functional portion thereof, is deleted.

2. The recombinant adenovirus of claim 1, wherein the insertion site comprises a deletion of 202 base pairs following the start site of E1b-19K.

3. The recombinant adenovirus of any one of claims 1 or 2, wherein the DNA sequence is a sequence encoding tumor necrosis factor, or a functional portion thereof.

4. The recombinant adenovirus of any one of claims 1 or 2, wherein the DNA sequence is a sequence encoding kras, or a functional portion thereof.

5. The recombinant adenovirus of claim 1, wherein at least one nucleotide in the range of −305 to −141 of said E1a regulatory sequence is retained.

6. The recombinant adenovirus of claim 1, wherein at least one of Pea3 II, Pea3 III, Pea3 IV, and Pea3 V, or a functional portion thereof, is deleted.

7. The recombinant adenovirus of claim 1, comprising the nucleic acid sequence of vector dl309-6, TAV-255, dl55, dl200, dl230, or dl200+230.

8. The recombinant adenovirus of claim 7, comprising the nucleic acid sequence of vector TAV-255.

9. The recombinant adenovirus of claim 1, wherein said recombinant virus selectively expresses an E1a isoform, wherein the sequence encoding the E1a isoform is operably linked to said modified E1a regulatory sequence.

10. The recombinant adenovirus of claim 9, wherein the virus selectively expresses E1a-12S.

11. The recombinant adenovirus of claim 9, wherein the virus selectively expresses E1a-13S.

12. The recombinant adenovirus of claim 1, wherein said recombinant virus substantially excludes expression of an E1a isoform, wherein the sequence encoding the E1a isoform is operably linked to said modified E1a regulatory sequence.

13. The recombinant adenovirus of claim 12, wherein the excluded E1a isoform is E1a-12S or E1a-13S.

* * * * *

SEQUENCE LISTING

<160> NUMBER OF SEQ ID NOS: 20

<210> SEQ ID NO 1
<211> LENGTH: 58
<212> TYPE: DNA
<213> ORGANISM: Artificial sequence
<220> FEATURE:
<223> OTHER INFORMATION: Synthetic oligonucleotide primer D194_243_F

<400> SEQUENCE: 1
aaagtgacgt ttttggtgtg cgccggtgtt ttgggcgtaa ccgagtaaga tttggcca         58

<210> SEQ ID NO 2
<211> LENGTH: 58
<212> TYPE: DNA
<213> ORGANISM: Artificial sequence
<220> FEATURE:
<223> OTHER INFORMATION: Synthetic oligonucleotide primer D194_243_R

<400> SEQUENCE: 2
tggccaaatc ttactcggtt acgcccaaaa caccggcgca caccaaaaac gtcacttt         58

<210> SEQ ID NO 3
<211> LENGTH: 35
<212> TYPE: DNA
<213> ORGANISM: Artificial sequence
<220> FEATURE:
<223> OTHER INFORMATION: Synthetic oligonucleotide primer dl212S

<400> SEQUENCE: 3
cggtgtacac aggaagtgac aatcggtttt aggcg              35

<210> SEQ ID NO 4
<211> LENGTH: 35
<212> TYPE: DNA
<213> ORGANISM: Artificial sequence
<220> FEATURE:
<223> OTHER INFORMATION: Synthetic oligonucleotide primer dl 212 As

<400> SEQUENCE: 4
cgcctaaaac cgattgtcac ttcctgtgta caccg              35

<210> SEQ ID NO 5
<211> LENGTH: 34
<212> TYPE: DNA
<213> ORGANISM: Artificial sequence
<220> FEATURE:
<223> OTHER INFORMATION: Synthetic oligonucleotide primer dl220S

<400> SEQUENCE: 5
agtgacaatt ttcgcgcagg cggatgttgt agta               34

<210> SEQ ID NO 6
<211> LENGTH: 34
<212> TYPE: DNA
<213> ORGANISM: Artificial sequence
<220> FEATURE:
<223> OTHER INFORMATION: Synthetic oligonucleotide primer dl220AS

<400> SEQUENCE: 6
agtgacaatt ttcgcgcagg cggatgttgt agta               34

<210> SEQ ID NO 7
<211> LENGTH: 41
<212> TYPE: DNA
<213> ORGANISM: Artificial sequence

```
<220> FEATURE:
<223> OTHER INFORMATION: Synthetic oligonucleotide primer dl275S

<400> SEQUENCE: 7
gtaaccgagt aagatttggc catggaaaac tgaataagag g          41

<210> SEQ ID NO 8
<211> LENGTH: 41
<212> TYPE: DNA
<213> ORGANISM: Artificial sequence
<220> FEATURE:
<223> OTHER INFORMATION: Synthetic oligonucleotide primer dl275AS

<400> SEQUENCE: 8
cctcttattc agttttccat ggccaaatct tactcggtta c          41

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide primer dl200S

<400> SEQUENCE: 9
gcgccggtgt acacagacaa ttttcgcgcg                       30

<210> SEQ ID NO 10
<211> LENGTH: 30
<212> TYPE: DNA
<213> ORGANISM: Artificial sequence
<220> FEATURE:
<223> OTHER INFORMATION: Synthetic oligonucleotide primer dl200AS

<400> SEQUENCE: 10
cgcgcgaaaa ttgtctgtgt acaccggcgc                       30

<210> SEQ ID NO 11
<211> LENGTH: 34
<212> TYPE: DNA
<213> ORGANISM: Artificial sequence
<220> FEATURE:
<223> OTHER INFORMATION: Synthetic oligonucleotide primer dl203S

<400> SEQUENCE: 11
ttcgcgcggt tttaggctgt agtaaatttg ggcg                  34

<210> SEQ ID NO 12
<211> LENGTH: 34
<212> TYPE: DNA
<213> ORGANISM: Artificial sequence
<220> FEATURE:
<223> OTHER INFORMATION: Synthetic oligonucleotide primer dl203AS

<400> SEQUENCE: 12
cgcccaaatt tactacagcc taaaaccgcg cgaa                  34

<210> SEQ ID NO 13
<211> LENGTH: 30
<212> TYPE: DNA
<213> ORGANISM: Artificial sequence
<220> FEATURE:
<223> OTHER INFORMATION: Synthetic oligonucleotide primer Ad143F

<400> SEQUENCE: 13
ggggtaccac atgtaagcga cggatgtggc                       30
```

<210> SEQ ID NO 14
<211> LENGTH: 27
<212> TYPE: DNA
<213> ORGANISM: Artificial sequence
<220> FEATURE:
<223> OTHER INFORMATION: Synthetic oligonucleotide primer Ad552R

<400> SEQUENCE: 14

```
aaactcgagc ccggtgtcgg agcggct                                          27
```

<210> SEQ ID NO 15
<211> LENGTH: 767
<212> TYPE: DNA
<213> ORGANISM: Artificial sequence
<220> FEATURE:
<223> OTHER INFORMATION: Synthetic DNA construct

<400> SEQUENCE: 15

```
atgatcgaaa catacaacca aacttctccc cgatctgcgc ccactgcact gcccatcagc      60
atgaaaattt ttatgtattt acttactgtt tttcttatca cccagatgat tcggtcagca     120 cttttttcctc tctatcttca tagaaggctg acaagatag aacatgaaag caatcttcat    180
gaagattttg tattcatgaa aacgatacag atgcaaccaa cacacgacaa agatccttat    240
ccttactgaa ctgtgaggag attaaaagcc agtttgaagg ctttgtgaag gatataatgt    300
taaacaaaga gcagacgaag aaagatgagg tagcccatgt tgtagcaaac cctcaagctg    360
aggggcagct ccactcgctc aaccgccgcg ccaatgccct cctggccaat ggcctcgagc    420
tcagagataa ccagctggtg gtgccatcag agggcctgta cctcatctac tcccaggtcc    480
tcttcaaggg ccaacgctgc ccctccaccc atgtgctcct cacccacacc atcagccgca    540
tcgccgtctc ctaccagacc aaggtcaacc tcctctctgc catcaagacc ccctcccaca    600
cccacacccc agagccggct gaccccaacc cctggtatga gcccatctat ctggcacggc    660
tcttccagct cgagaaggct gaccgactca gcgctgagat caatcggccc gactatctcg    720
actttgcgca gtctgggcag gtctactttg gaatcattgc tctgtga                  767
```

<210> SEQ ID NO 16
<211> LENGTH: 764
<212> TYPE: DNA
<213> ORGANISM: Artificial sequence
<220> FEATURE:
<223> OTHER INFORMATION: Synthetic DNA construct
<220> FEATURE:
<221> NAME/KEY: misc_feature
<222> LOCATION: (761)..(762)
<223> OTHER INFORMATION: n is a, c, g, or t

<400> SEQUENCE: 16

```
tatacttgaa cccttacgac atgatcgaaa catacaacca aacttctccc cgatctgcgg      60
ccactggact gcccatcagc atgaaaattt ttatgtattt acttactgtt tttcttatca     120
cccagatgat tgggtcagca cttttttgctg tgtatcttca tagaagcctg cacaagatag    180
aagatgaaag gaatcttcat gaagattttg tattcatgaa aacgatacag atgcaaca      240 caggagaaag atcctttatcc ttactgaact gtgaggagat aaaagccag tttgaaggct    300 ttgtgaagga tataatgtta aacaaagagg agacgaagaa agatcaggta gcccatgttg    360
tagcaaaccc tcaagctgag gggcagctcc agtggctgaa ccgccgggcc aatgccctcc    420
tggccaatgg cgtggagctg agataaacc agctggtggt gccatcagag ggcctgtacc    480
tcatctactc ccaggtcctc ttcaagggcc aaggctgccc ctccacccat gtgctcctca   540
```

```
cccacaccat cagccgcatc gccgtctcct accagaccaa ggtcaacctc ctctctgcca    600
tcaagagccc ctgccagagg gagacccag aggggctga ggccaagccc tggtatgagc    660
ccatctatct gggaggggtc ttccagctgg agaagggtga ccgactcagc gctgagatca    720
atcggcccga ctatctcgac ttgcggagtc tggcagtcta nntt                   764
```

<210> SEQ ID NO 17
<211> LENGTH: 764
<212> TYPE: DNA
<213> ORGANISM: Artificial sequence
<220> FEATURE:
<223> OTHER INFORMATION: Synthetic DNA construct

<400> SEQUENCE: 17

```
atgatcgaaa catacaacca aacttctccc cgatctgcgg ccactggact gcccatcagc     60
atgaaaattt ttatgtattt acttactgtt tttcttatca cccagatgat tgggtcagca    120 cttttttgctg tgtatcttca tagaaggctg acaagatag aagatgaaag gaatcttcat    180
gaagattttg tattcatgaa acgatacag agatgcaaca caggagaaag atccttatcc    240
ttactgaact gtgaggagat taaaagccag tttgaaggct tgtgaagga tataaagtta    300 aacaaagagg agacgaagaa agatgaggta gcccatgttg tagcaaaccc tcaagctgag    360 ggcagctcc agtggctgaa ccgccgggcc aatgccctcc tggccaatgg cgtggagctg    420
agagataacc agctggtggt gccatcagag ggcctgtacc tcatctactc ccaggtcctc    480
ttcaagggcc aaggctgccc ctccacccat gtgctcctca cccacaccat cagccgcatc    540
gccgtctcct accagaccaa ggtcaacctc ctctctgcca tcaagagccc ctgccagagg    600 gagacccag aggggctga ggccaagccc tggtatgagc ccatctatct gggaggggtc    660
ttccagctgg agaagggtga ccgactcagc gctgagatca atcggcccga ctatctgact    720
ttgcggagtc tgggcaggtc tactttggaa tcattgctct gtga                   764
```

<210> SEQ ID NO 18
<211> LENGTH: 676
<212> TYPE: DNA
<213> ORGANISM: Artificial sequence
<220> FEATURE:
<223> OTHER INFORMATION: Synthetic DNA construct

<400> SEQUENCE: 18

```
ttctcccgat ctgcggccac tggactgccc atcagcatga aatttttat gtatttactt     60 actgttttttc ttatcaccca gatgattggg tcagcacttt tgctgtgta tcttcataga    120 aggctggaca agatagaaga tgaaaggaat cttcatgaag attttgtatt catgaaaacg    180
atacagagat gcaacacagg agaaagatcc ttatccttac tgaactgtga ggagattaaa    240
agccagtttg aaggctttgt gaaggatata atgttaaaca agaggagac gaagaaagat    300 gaggtagccc atgttgtagc aaaccctcaa gctgagggc agctccagtg gctgaaccgc    360
cgggccaatg ccctcctggc caatggcgtg gagctgagag ataaccagct ggtggtgcca    420
tcagagggcc tgtacctcat ctactcccag gtcctcttca agggccaagg ctgcccctcc    480
acccatgtgc tcctcaccca ccatcagc cgcatcgccg tctcctacca gaccaaggtc    540
aacctcctct ctgccatcaa gagccctgc cagagggaga cccagaggg gctgaggcc    600 aagccctggt atgagcccat ctatctggga ggggtcttcc agctggagaa gggtgaccga    660
ctcagcgctg agatca                                                  676
```

<210> SEQ ID NO 19
<211> LENGTH: 780
<212> TYPE: DNA
<213> ORGANISM: Artificial sequence
<220> FEATURE:
<223> OTHER INFORMATION: Synthetic DNA construct
<220> FEATURE:
<221> NAME/KEY: misc_feature
<222> LOCATION: (1)..(4)
<223> OTHER INFORMATION: n is a, c, g, or t

<400> SEQUENCE: 19

```
nnnntctcac tacggttgca ggcgggtgag tagtagtgtg cggaagtgt  datgttgcaa      60
gtgtggcgga acacatgtaa gcgacggatg tggcaaaagt gacgttttttg gtgtgcgccg     120
gtgtttggg cgtaaccgag taagatttgg ccattttcgc gggaaaactg aataagagga      180
agtgaaatct gaataatttt gtgttactca tagcgcgtaa tatttgtcta gggccgcggg     240
gactttgacc gtttacgtgg agactcgccc aggtgttttt ctcaggtgtt ttccgcgttc     300
cgggtcaaag ttggcgtttt attattatag tcagctgacg tgtagtgtat ttatacccgg     360
tgagttcctc aagaggccac tcttgagtgc cagcgagtag agttttctcc tccgagccgc     420
tccgacaccg ggactgaaaa tgagacatat tatctgccac ggaggtgtta ttaccgaaga     480
aatggccgcc agtcttttgg accagctgat cgaagaggta ctggctgata atcttccacc     540
tcctagccat tttgaaccac ctacccttca cgaactgtat gatttagacg tgacggcccc     600
cgaagatccc aacgaggagg cggtttcgca gattttttccc gactctgtaa tgttggcggt     660
gcaggaaggg attgacttac tcactttttcc gccggcgccc ggttctccgg agccgcctca     720
cctttcccgg cagcccgagc agccggagca gagagccttg ggtccggttt ctatgccaaa     780
```

<210> SEQ ID NO 20
<211> LENGTH: 900
<212> TYPE: DNA
<213> ORGANISM: Artificial sequence
<220> FEATURE:
<223> OTHER INFORMATION: Synthetic DNA construct

<400> SEQUENCE: 20

```
cccttccagc tctctgcccc ttttggattg aagccaatat gataatgagg ggtggagttt      60
gtgacgtggc gcggggcgtg ggaacggggc gggtgacgta gtagtgtggc ggaagtgtga     120
tgttgcaagt gtggcggaac acatgtaagc gacggatgtg gcaaaaagtg acgttttttgg    180
tgtgcgccgg tgtacacagg aagtgacaat tttcgcgcgg ttttaggcgg atgttgtagt     240
aaatttgggc gtaaccgagt aagatttggc cattttcgcg ggaaaactga ataagaggaa     300
gtgaaatctg aataattttg tgttactcat agcgcgtaat atttgtctag ggccgcgggg     360
actttgaccg tttacgtgga gactcgccca ggtgtttttc tcaggtgttt tccgcgttcc     420
gggtcaaagt tggcgtttta ttattatagt cagctgacgt atagtgtatt tatacccggt     480
gagttcctca agaggccact cttgagtgcc agcgagtaga gttttctcct ccgagccgct     540
ccgacaccgg gactgaaaat gagacatatt atctgccacg gaggtgttat taccgaagaa     600
atggccgcca gtcttttgga ccagctgatc gaagaggtac tggctgataa tcttccacct     660
cctagccatt ttgaaccacc tacccttcac gaactgtatg atttagacgt gacggccccc     720
gaagatccca acgaggaggc ggtttcgcag attttttcccg actctgtaat gttggcggtg     780
```

```
caggaaggga ttgacttact cacttttccg ccggcgcccg gttctccgga gccgcctcac    840
cttttcccgg cagcccgagc agccggagca gagagccttg ggtccggttt ctatgccaaa    900
```